(12) United States Patent
French

(10) Patent No.: US 10,729,789 B2
(45) Date of Patent: Aug. 4, 2020

(54) COMPOSITIONS AND METHODS FOR ADENO-ASSOCIATED VIRUS MEDIATED GENE EXPRESSION IN MYOFIBROBLAST-LIKE CELLS

(71) Applicant: Brent A. French, Charlottesville, VA (US)

(72) Inventor: Brent A. French, Charlottesville, VA (US)

(73) Assignee: University of Virginia Patent Foundation, Charlottesville, VI (US)

( * ) Notice: Subject to any disclaimer, the term of this patent is extended or adjusted under 35 U.S.C. 154(b) by 0 days.

(21) Appl. No.: 16/078,266

(22) PCT Filed: Mar. 1, 2017

(86) PCT No.: PCT/US2017/020113
§ 371 (c)(1),
(2) Date: Aug. 21, 2018

(87) PCT Pub. No.: WO2017/151717
PCT Pub. Date: Sep. 8, 2017

(65) Prior Publication Data
US 2019/0151471 A1 May 23, 2019

Related U.S. Application Data

(60) Provisional application No. 62/301,985, filed on Mar. 1, 2016.

(51) Int. Cl.
| | |
|---|---|
| *A61K 48/00* | (2006.01) |
| *A61K 35/34* | (2015.01) |
| *C12N 15/86* | (2006.01) |
| *A61P 9/10* | (2006.01) |

(52) U.S. Cl.
CPC .......... *A61K 48/0058* (2013.01); *A61K 35/34* (2013.01); *A61K 48/0008* (2013.01); *A61K 48/0066* (2013.01); *A61P 9/10* (2018.01); *C12N 15/86* (2013.01); *C12N 2750/14143* (2013.01); *C12N 2830/008* (2013.01)

(58) Field of Classification Search
CPC .. A01K 2207/05; C12N 15/113; C12N 15/86; A61K 48/0058
See application file for complete search history.

(56) References Cited

U.S. PATENT DOCUMENTS

| | | | | |
|---|---|---|---|---|
| 2003/0072744 A1* | 4/2003 | Engler | ............... | A61K 38/1709 424/93.21 |
| 2010/0166827 A1* | 7/2010 | Kuhn | .................. | C12N 5/0657 424/426 |

OTHER PUBLICATIONS

Aikawa et al. The Journal of Biological Chemistry vol. 277 pp. 18979-18985 (Year: 2002).*
Piras et al. Gene Therapy 23, 469-478 (Year: 2016).*
Lindsley et al. Dev Biol 307: 304-355 (Year: 2007).*
Souders et al. Circ Res. 105: 1164-1176 (Year: 2009).*
Frangogiannis Current Medicinal Chemistry 13, 1877-1893 (Year: 2006).*
Ellis et al., A survey of ex vivo/in vitro transduction efficiency of mammalian primary cells and cell lines with Nine natural adeno-associated virus (AAV1-9) and one engineered adeno-associated virus serotype Virol J. Mar. 6, 2013;10:74.
Frangogiannis NG, Michael LH, Entman ML. Myofibroblasts in reperfused myocardial infarcts express the embryonic form of smooth muscle myosin heavy chain (S Memb ). Cardiovasc Res 2000; 48: 89-100.
Furtado MB, Costa MW, Pranoto EA, Salimova E, Pinto AR, Lam NT et al. Cardiogenic Genes Expressed in Cardiac Fibroblasts Contribute to Heart Development and Repair. Circ Res 2014; 114: 1422-1434.
Ieda M, Fu J-D, Delgado-Olguin P, Vedantham V, Hayashi Y, Bruneau BG et al. Direct Reprogramming of Fibroblasts into Functional Cardiomyocytes by Defined Factors. Cell 2010; 142: 375-386.
Inagaki K, Fuess S, Storm TA, Gibson GA, Mctiernan CF, KayMA eta/. Robust Systemic Transduction with AAV9 Vectors in Mice: Efficient Global Cardiac GeneTransfer Superior to That of AAV8. Mol Ther 2006; 14:45-53.
Inagawa K, Miyamoto K, Yamakawa H, Muraoka N, Sadahiro T, Umei T et al. Induction of Cardiomyocyte-like Cells in Infarct Hearts by Gene Transfer of Gata4, Mef2c, and Tbx5. Circ Res. Oct. 12, 2012;111(9):1147-56.
International Preliminary Report on Patentability corresponding to U.S. International Application No. PCT/US2017/020113 dated Sep. 4, 2018.
International Search Report corresponding to U.S. International Application No. PCT/US2017/020113 dated Jun. 2, 2017.
Jayawardena TM, Egemnazarov B, Finch EA, Zhang L, Payne JA, Pandya Ketal. MicroRNA-Mediated In Vitro and In Vivo Direct Reprogramming of Cardiac Fibroblasts to Cardiomyocytes. Circ Res 2012; 110: 1465-1473.
Kuhn B, del Monte F, Hajjar RJ, Chang Y-S, Lebeche D, Arab S et al. Periostin induces proliferation of differentiated cardiomyocytes and promotes cardiac repair.

(Continued)

*Primary Examiner* — Brian Whiteman
(74) *Attorney, Agent, or Firm* — Jenkins, Wilson, Taylor & Hunt, P.A.

(57) ABSTRACT

The present application discloses a recombinant AAV vector comprising a promoter that targets gene expression to myofibroblast-like lineage of cells in the heart. The present application, also discloses the preparation and use of AAV expression cassettes using a modified periostin promoter that successfully drives gene expression in cardiac myofibroblast-like cells. The present invention encompasses compositions and methods useful for treating myocardial infarction. Further comprising compositions and methods for preparing and using AAV vectors for targeting cells and inducing gene expression. The compositions and methods of the invention are useful for efficiently targeting cardiac myofibroblasts following a cardiac injury, disease, or disorder. Further comprising a kit for effecting alleviation of the various diseases or disorders recited herein.

20 Claims, 8 Drawing Sheets
(7 of 8 Drawing Sheet(s) Filed in Color)
Specification includes a Sequence Listing.

(56) References Cited

OTHER PUBLICATIONS

Konkalmatt PR, Beyers RJ, O'Connor DM, Xu Y, Seaman ME, French BA. Cardiac-Selective Expression of Extracellular Superoxide Dismutase After Systemic Injection of Adeno-Associated Virus 9 Protects the Heart Against Post-Myocardial Infarction Left Ventricular Remodeling. Circ Cardiovasc Imaging 2013; 6: 478-486.
Konkalmatt PR, Wang F, Piras BA, Xu Y, O'Connor DM, Beyers RJ et al. Adeno-associated virus serotype 9 administered systemically after reperfusion preferentially targets cardiomyocytes in the infarct border zone with pharmacodynamics suitable for the attenuation of left ventricular remodeling. J Gene A1ed 2012; 14: 609-620.
Lovric J, Mano M, Zentilin L, Eulalia A, Zacchigna S, Giacca M. Terminal Differentiation of Cardiac and Skeletal Myocytes Induces Permissivity to AAV Transduction by Relieving Inhibition Imposed by DNA Damage Response Proteins. Mol Ther 2012; 20: 2087-2097.
Oka T, Xu J, Kaiser RA, Melendez J, Hambleton M, Sargent MA et al. Genetic Manipulation of Periostin Expression Reveals a Role in Cardiac Hypertrophy and Ventricular Remodeling. Circ Res 2007; 101: 313-321.
Piras et al. "Systemic injection of AAV9 carrying periostin promoter targets gene expression to a myofibroblast-like lineage in mouse hearts after reperfused myocardial infarction," Gene Therapy, Feb. 29, 2016, vol. 23, pp. 469-478.
Prasad K-MR, Smith RS, Xu Y, French BA. A single direct injection into the left ventricular wall of an adeno-associated virus 9 (AAV9) vector expressing extracellular superoxide dismutase from the cardiac troponin-T promoter protects mice against myocardial infarction. J Gene Med 2011; vol. 13, pp. 333-341.
Prasad KMR, Xu Y, Yang Z, Acton ST, French BA. Robust cardiomyocyte-specific gene expression following systemic injection of AAV: in vivo gene delivery follows a Poisson distribution. Gene Ther 2011; 18: 43-52.
Qian L, Huang Y, Spencer CI, Foley A, Vedantham V, Liu L et al. In vivo reprogramming of murine cardiac fibroblasts into induced cardiomyocytes. Nature 2012; 485: 593-598.
Santiago J-J, Dangerfield AL, Rattan SG, Bathe KL, Cunnington RH, Raizman JE et al. Cardiac fibroblast to myofibroblast differentiation in vivo and in vitro: Expression of focal adhesion components in neonatal and adult rat ventricular myofibroblasts. Dev Dyn 2010; 239: 1573-1584.
Sharma A, Ghosh A, Hansen ET, Newman JM, Mohan RR. Transduction efficiency of AAV 2/6, 2/8 and 2/9 vectors for delivering genes in human corneal fibroblasts. Brain Res Bull 2010; 81: 273-278.
Shimazaki M, Nakamura K, Kii I, Kashima T, Amizuka N, LiM et al. Periostin is essential for cardiac healing after acute myocardial infarction. J Exp Med 2008; 205: 295-303.
Snider P, Standley KN, Wang J, Azhar M, Doetschman T, Conway SJ. Origin of Cardiac Fibroblasts and the Role of Periostin. Circ Res 2009; 105: 934-947.
Takeda N, Manabe I, Uchino Y, Eguchi K, Matsumoto S, Nishimura S et al. Cardiac fibroblasts are essential for the adaptive response of the murine heart to pressure overload. J Clin Invest 2010; 120: 254-265.
Van Wijk B, Gunst QD, Moorman AF, Van den Hoff MJ. Cardiac regeneration from activated epicardium. PLoS One 2012; 7: e44692.
Written Opinion corresponding to U.S. International Application No. PCT/US2017/020113 dated Jun. 2, 2017.
Wu Z, Asokan A, Samulski R. Adeno-associated Virus Serotypes: Vector Toolkit for Human Gene Therapy. Mol Ther 2006; vol. 14, pp. 316-327.
Zincarelli C, Soltys S, Rengo G, Rabinowitz JE. Analysis of AAV Serotypes 1-9 Mediated Gene Expression and Tropism in: Mice After Systemic Injection. Mol Ther 2008; vol. 16, pp. 1073-1080.

* cited by examiner

FIG. 4A
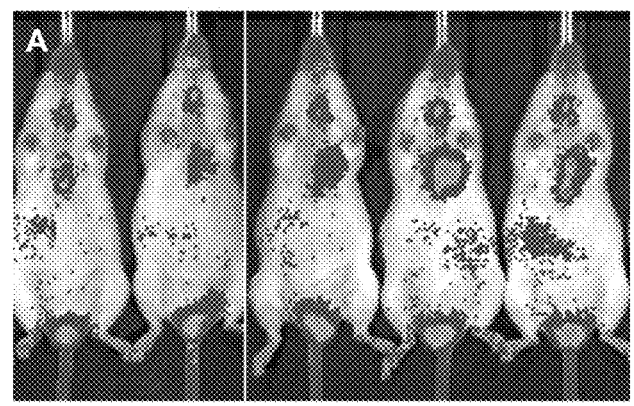
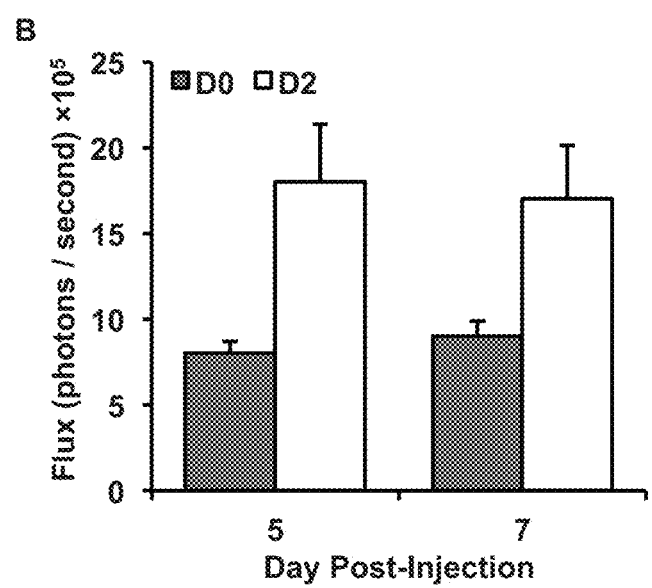
FIG. 4B

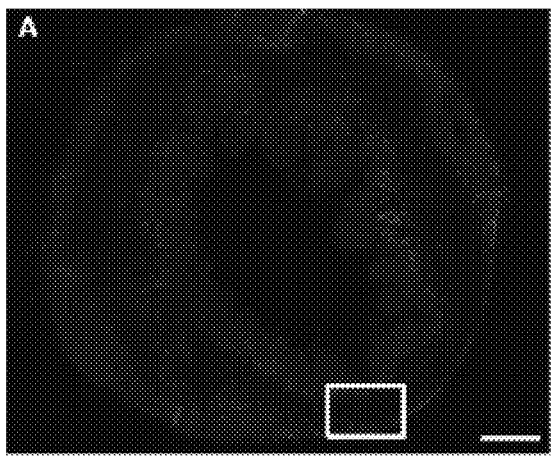
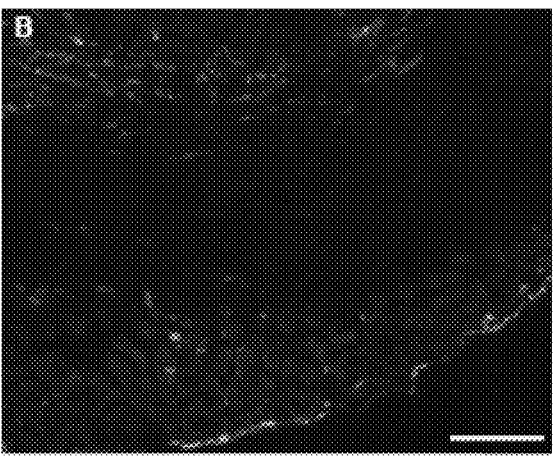
FIG. 5A　　　　　　　　FIG. 5B
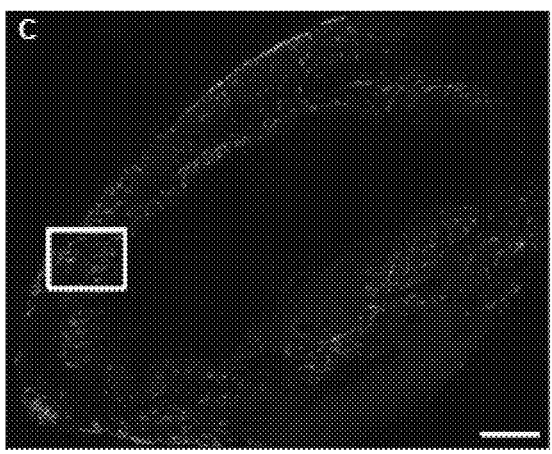
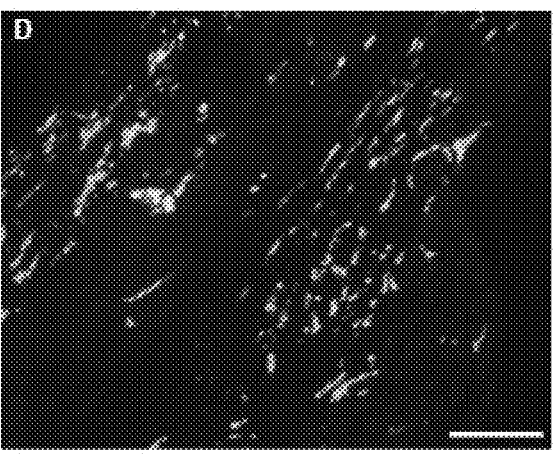
FIG. 5C　　　　　　　　FIG. 5D
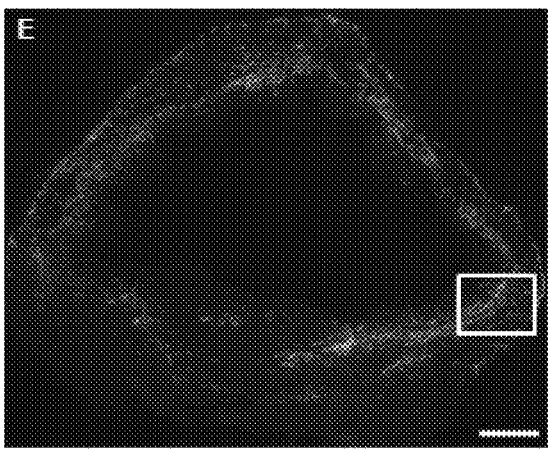
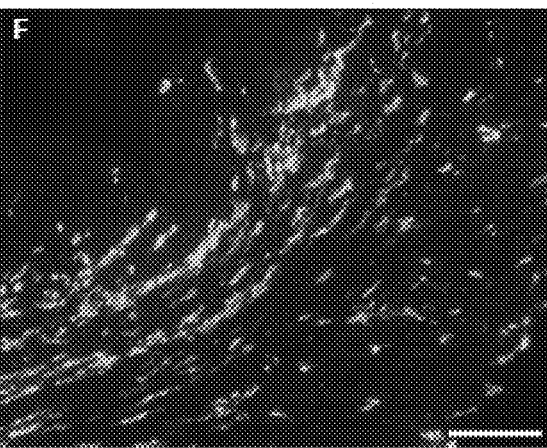
FIG. 5E　　　　　　　　FIG. 5F

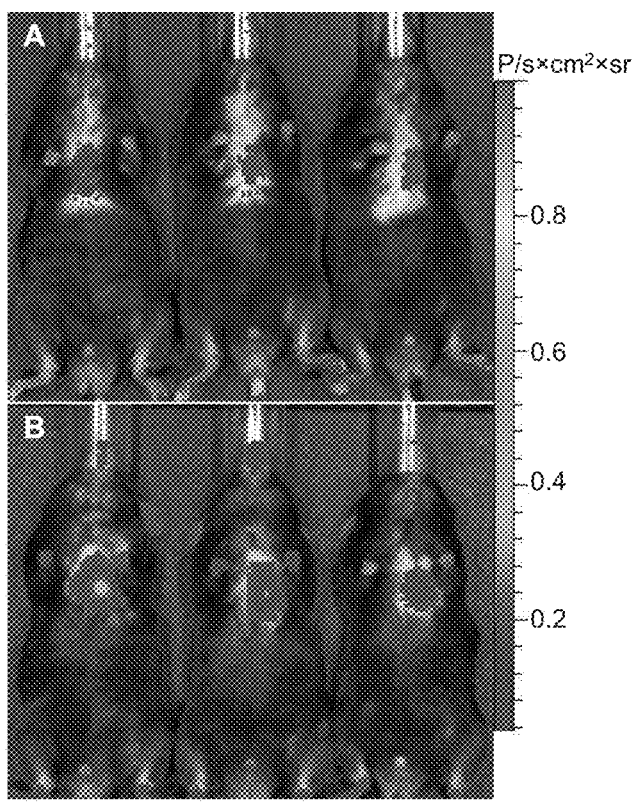
FIG. 6A
FIG. 6B
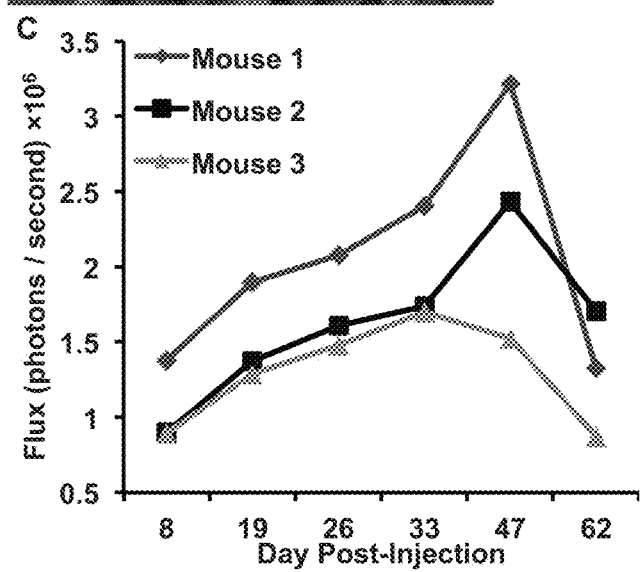
FIG. 6C

SEQUENCE LISTING

```
<160> NUMBER OF SEQ ID NOS: 9

<210> SEQ ID NO 1
<211> LENGTH: 4385
<212> TYPE: DNA
<213> ORGANISM: adeno-associated virus 9

<400> SEQUENCE: 1
cagagaggga gtggccaact ccatcactag gggtaatcgc gaagcgcctc ccacgctgcc      60
gcgtcagcgc tgacgtagat tacgtcatag gggagtggtc ctgtattagc tgtcacgtga     120
gtgcttttgc gacattttgc gacaccacat ggccatttga ggtatatatg gccgagtgag     180
cgagcaggat ctccattttg accgcgaaat ttgaacgagc agcagccatg ccgggcttct     240
acgagattgt gatcaaggtg ccgagcgacc tggacgagca cctgccgggc atttctgact     300
cttttgtgaa ctgggtggcc gagaaggaat gggagctgcc cccggattct gacatggatc     360
ggaatctgat cgagcaggca ccctgaccg tggccgagaa gctgcagcgc gacttcctgg     420
tccaatggcg ccgcgtgagt aaggccccgg aggccctctt ctttgttcag ttcgagaagg     480
gcgagagcta ctttcacctg cacgttctgg tcgagaccac gggggtcaag tccatggtgc     540
taggccgctt cctgagtcag attcgggaga agctggtcca gaccatctac cgcgggatcg     600
agccgaccct gcccaactgg ttcgcggtga ccaagacgcg taatggcgcc ggcggggga     660 acaaggtggt ggacagtgc tacatcccca actacctcct gcccaagact cagcccgagc     720
tgcagtgggc gtggactaac atggaggagt atataagcgc gtgcttgaac ctggccgagc     780
gcaaacggct cgtggcgcag cacctgaccc acgtcagcca gacgcaggag cagaacaagg     840
agaatctgaa ccccaattct gacgcgcccg tgatcaggtc aaaaacctcc gcgcgctaca     900
tggagctggt cgggtggctg gtggaccggg gcatcacctc cgagaagcag tggatccagg     960
aggaccaggc ctcgtacatc tccttcaacg ccgcctccaa ctcgcggtcc cagatcaagg    1020
```

| | |
|---|---|
| ccgcgctgga caatgccggc aagatcatgg cgctgaccaa atccgcgccc gactacctgg | 1080 |
| taggcccttc acttccggtg gacattacgc agaaccgcat ctaccgcatc ctgcagctca | 1140 |
| acggctacga ccctgcctac gccggctccg tctttctcgg ctgggcacaa aagaagttcg | 1200 |
| ggaaacgcaa caccatctgg ctgtttgggc cggccaccac gggaaagacc aacatcgcag | 1260 |
| aagccattgc ccacgccgtg cccttctacg gctgcgtcaa ctggaccaat gagaactttc | 1320 |
| ccttcaacga ttgcgtcgac aagatggtga tctggtggga ggagggcaag atgacggcca | 1380 |
| aggtcgtgga gtccgccaag gccattctcg gcggcagcaa ggtgcgcgtg gaccaaaagt | 1440 |
| gcaagtcgtc cgcccagatc gaccccactc ccgtgatcgt cacctccaac accaacatgt | 1500 |
| gcgccgtgat tgacgggaac agcaccacct tcgagcacca gcagcctctc caggaccgga | 1560 |
| tgtttaagtt cgaactcacc cgccgtctgg agcacgactt tggcaaggtg acaaagcagg | 1620 |
| aagtcaaaga gttcttccgc tgggccagtg atcacgtgac cgaggtggcg catgagtttt | 1680 |
| acgtcagaaa gggcggagcc agcaaaaagac ccgcccccga tgacgcggat aaaagcgagc | 1740 |
| ccaagcgggc ctgcccctca gtcgcggatc catcgacgtc agacgcggaa ggagctccgg | 1800 |
| tggactttgc cgacaggtac caaaacaaat gttctcgtca cgcgggcatg cttcagatgc | 1860 |
| tgcttccctg caaaacgtgc gagagaatga atcagaattt caacatttgc ttcacacacg | 1920 |
| gggtcagaga ctgctcagag tgttccccg gcgtgtcaga atctcaaccg gtcgtcagaa | 1980 |
| agaggacgta tcggaaactc tgtgcgattc atcatctgct ggggcgggct ccgagattg | 2040 |
| cttgctcggc ctgcgatctg gtcaacgtgg acctggatga ctgtgtttct gagcaataaa | 2100 |
| tgacttaaac caggtatggc tgccgatggt tatcttccag attggctcga ggacaacctc | 2160 |
| tctgagggca ttcgcgagtg gtgggcgctg aaacctggag ccccgaagcc caaagccaac | 2220 |
| cagcaaaagc aggacgacgg ccggggtctg gtgcttcctg gctacaagta cctcggaccc | 2280 |
| ttcaacggac tcgacaaggg ggagcccgtc aacgcggcgg acgcagcggc cctcgagcac | 2340 |
| ggcaaggcct acgaccagca gctgcaggcg ggtgacaatc cgtacctgcg gtataaccac | 2400 |
| gccgacgccg agtttcagga gcgtctgcaa gaagatacgt cttttgggg caacctcggg | 2460 |
| cgagcagtct tccaggccaa gaagcgggtt ctcgaacctc tcggtctggt tgaggaaggc | 2520 |
| gctaagacgg ctcctggaaa gaagagaccg gtagagccat caccccagcg ttctccagac | 2580 |
| tcctctacgg gcatcggcaa gaaaggccaa cagcccgcca gaaaaagact caattttggt | 2640 |
| cagactggcg actcagagtc agttccagac cctcaacctc tcggagaacc tccagcagcg | 2700 |
| ccctctggtg tgggacctaa tacaatggct gcaggcggtg gcgcaccaat ggcagacaat | 2760 |
| aacgaaggcg ccgacggagt gggtaattcc tcgggaaatt ggcattgcga ttccacatgg | 2820 |
| ctggggaca gagtcatcac caccagcacc cgaacctggg cattgcccac ctacaacaac | 2880 |
| cacctctaca agcaaatctc caatggaaca tcgggaggaa gcaccaacga caacacctac | 2940 |
| tttggctaca gcacccccctg ggggtatttt gacttcaaca gattccactg ccacttctca | 3000 |
| ccacgtgact ggcagcgact catcaacaac aactggggat tccggccaaa gagactcaac | 3060 |
| ttcaagctgt tcaacatcca ggtcaaggag gttacgacga acgaaggcac caagaccatc | 3120 |
| gccaataacc ttaccagcac cgtccaggtc tttacggact cggagtacca gctaccgtac | 3180 |
| gtcctaggct ctgcccacca aggatgcctg ccaccgtttc ctgcagacgt cttcatggtt | 3240 |
| cctcagtacg gctacctgac gctcaacaat ggaagtcaag cgttaggacg ttcttctttc | 3300 |
| tactgtctgg aatactttcc cttctcagatg ctgagaccg gcaacaactt tcagttcagc | 3360 |
| tacacttcg aggacgtgcc tttccacagc agctacgcac acagccagag tctagatcga | 3420 |

```
ctgatgaacc ccctcatcga ccagtaccta tactacctgg tcagaacaca gacaactgga    3480
actgggggaa ctcaaacttt ggcattcagc caagcaggcc ctagctcaat ggccaatcag    3540
gctagaaact gggtacccgg gccttgctac cgtcagcagc gcgtctccac aaccaccaac    3600
caaaataaca acagcaactt tgcgtggacg ggagctgcta aattcaagct gaacgggaga    3660
gactcgctaa tgaatcctgg cgtggctatg catcgcaca aagacgacga ggaccgcttc    3720
tttccatcaa gtggcgttct catatttggc aagcaaggag ccgggaacga tggagtcgac    3780
tacagccagg tgctgattac agatgaggaa gaaattaaag ccaccaaccc tgtagccaca    3840
gaggaatacg gagcagtggc catcaacaac caggccgcta acacgcaggc gcaaactgga    3900
cttgtgcata accagggagt tattcctggt atggtctggc agaaccggga cgtgtacctg    3960
cagggcccta tttgggctaa aatacctcac acagatggca actttcaccc gtctcctctg    4020
atgggtggat ttggactgaa acacccacct ccacagattc taattaaaaa tacaccagtg    4080
ccggcagatc ctcctcttac cttcaatcaa gccaagctga actctttcat cacgcagtac    4140
agcacgggac aagtcagcgt ggaaatcgag tgggagctgc agaaagaaaa cagcaagcgc    4200
tggaatccag agatccagta tacttcaaac tactacaaat ctacaaatgt ggactttgct    4260
gtcaatacca aaggtgttta ctctgagcct cgccccattg gtactcgtta cctcacccgt    4320
aatttgtaat tgcctgttaa tcaataaacc ggttaattcg tttcagttga actttggtct    4380
ctgcg                                                                4385

<210> SEQ ID NO 2
<211> LENGTH: 4393
<212> TYPE: DNA
<213> ORGANISM: adeno-associated virus 8

<400> SEQUENCE: 2
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccagtgagc     180 gagcaggatc tccattttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatgcgcg cgcgtgagta aggcccccga ggccctcttc tttgttcagt tcgagaaggg     480
cgagagctac tttcacctgc acgttctggt cgagaccacg ggggtcaagt ccatggtgct     540
aggccgcttc ctgagtcaga ttcgggaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca gactcagcc     720 cgagctgcag tgggcgtgga ctaacatgga ggagtatata agcgcgtgct tgaacctggc     780
cgagcgcaaa cggctcgtgg cgcagcacct gacccgtgtc agccagacgc aggagcagaa     840
caaggagaat ctgaacccca ttctgacgc gcccgtgatc aggtcaaaaa cctccgcgcg     900
ctatatggag ctggtcgggt ggctggtgga ccggggcatc acctccgaga agcagtggat     960
ccaggaggac caggcctcgt acatctcctt caacgccgcc tccaactcgc ggtcccgat    1020 caaggccgcg ctggacaatg ccggcaagat catggcgctg accaaatccg cgcccgacta    1080
```

```
cctggtgggg ccctcgctgc ccgcggacat tacccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgccctt ctacggctgc gtcaactgga ccaatgagaa   1320
ctttcccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc caccccgtg atcgtcacct ccaacaccaa    1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct tccgctgggc cagtgatcac gtgaccgagg tggcgcatga   1680
gttttacgtc agaaagggcg gagccagcaa aagacccgcc cccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc cgtcaacgc ggcggacgca gcggccctcg    2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagaccctca acctctcgga gaacctccag   2700
cagcgccctc tggtgtggga cctaatacaa tggctgcagg cggtggcgca ccaatggcag   2760
acaataacga aggcgccgac ggagtgggta gttcctcggg aaattggcat tgcgattcca   2820
catggctggg cgacagagtc atcaccacca gcacccgaac ctgggccctg cccacctaca   2880
acaaccacct ctacaagcaa atctccaacg ggacatcggg aggagccacc aacgacaaca   2940
cctacttcgg ctacagcacc ccctgggggt attttgactt taacagattc cactgccact   3000
tttcaccacg tgactggcag cgactcatca caacaactg gggattccgg cccaagagac    3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc caccagggct gcctgcctcc gttcccggcg gacgtgttca   3240
tgattcccca gtacggctac ctaacactca acaacggtag tcaggccgtg gaacgctcct   3300
ccttctactg cctggaatac tttccttcgc agatgctgag aaccggcaac aacttccagt   3360
ttacttacac cttcgaggac gtgcctttcc acagcagcta cgcccacagc cagagcttgg   3420
accggctgat gaatcctctg attgaccagt acctgtacta cttgtctcgg actcaaacaa   3480
```

```
caggaggcac ggcaaatacg cagactctgg gcttcagcca aggtgggcct aatacaatgg    3540
ccaatcaggc aaagaactgg ctgccaggac cctgttaccg ccaacaacgc gtctcaacga    3600
caaccgggca aaacaacaat agcaactttg cctggactgc tgggaccaaa taccatctga    3660
atggaagaaa ttcattggct aatcctggca tcgctatggc aacacacaaa gacgacgagg    3720
agcgtttttt tcccagtaac gggatcctga ttttggcaa acaaaatgct gccagagaca    3780
atgcggatta cagcgatgtc atgctcacca gcgaggaaga aatcaaaacc actaaccctg    3840
tggctacaga ggaatacggt atcgtggcag ataacttgca gcagcaaaac acggctcctc    3900
aaattggaac tgtcaacagc cagggggcct acccggtat ggtctggcag aaccgggacg    3960
tgtacctgca gggtcccatc tgggccaaga ttcctcacac ggacggcaac ttccacccgt    4020
ctccgctgat gggcggcttt ggcctgaaac atcctccgcc tcagatcctg atcaagaaca    4080
cgcctgtacc tgcggatcct ccgaccacct tcaaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcacccgtaa tctgtaattg cctgttaatc aataaaccgg ttgattcgtt tcagttgaac    4380
tttggtctct gcg                                                      4393

<210> SEQ ID NO 3
<211> LENGTH: 6354
<212> TYPE: DNA
<213> ORGANISM: Artificial Sequence
<220> FEATURE:
<223> OTHER INFORMATION: plasmid with luciferase and mouse periostin
      promoter

<400> SEQUENCE: 3
gaactcgatc gagcagctgc gcgctcgctc gctcactgag gccgcccggg caaagcccgg      60
gcgtcgggcg acctttggtc gcccggcctc agtgagcgag cgagcgcgca gagagggagt     120
ggccaactcc atcactaggg gttccttgta gttaatgatt aacccgccat gctacttatc     180
tacgtagcca tgctctagag acctctgtag gctggctggt gatactcaat tttatttcat     240
gtatacacaa cattttaaag atggaaatta gtacatgatt cttgatttaa attctttcaa     300
gctaacaatc ttttttttt tttaaagtg gcctcagtca aagacactaa agatcaccga     360
gtcttgcata gagtttccat ttacaggact agagaaagct agtggagaca cagatcgggt     420
gcggaggtag tgagaagcac ttttcctaag aaggtgcagg gttgactcca aggcttggct     480
gggttataag agttacatgt attatttatt ctatatgtaa gcaacttttg agctcatgtg     540
ccatggcaac ctatggaccg catgttaata tagaagcatt ttaaaattag tgatacaatc     600
aagaccaagg gcatcctgct tatggttttgt gtgcacaggc ttacagagtg cagagtccgc     660
gaggagtccc agggactgct ggagtttgag gttggtttca cagtggtgag taagcgtggc     720
agtgtaatga cctcatggtc tcccgaggcc agataacaga gaactgccta taaatcagca     780
tgccgcggct agagagaaac ggccctgttt ctcagacaca ctatctctct tcagctacat     840
aatgaaccat ttctttctca gtaatgactt acatctctgg gtcagacttt gcagccctgg     900
aaagtcggac ttcatttca tgatttccgt catcttcccg actggtagga aaattgcagg     960
ggtcagtagt gtcagcatag tttcacagag ctgaagagaa agggccctgt gtggagagcg    1020
acttttgatg agagccccgg aagagagtgt gcccttccgg ggattttttt cccagtctct    1080
```

```
tctacaactt cagctagcca attgaggggc atgtgtctct tccacataag ctgtggaaat    1140
cacactttaa atgcattgta catctatcca ggatttgggt taaatgcccc tgtgatttct    1200
cttctccgtg ttctgctgtg gagtgattta agtgcaatca gatcaaacca ggaaagtaac    1260
tgagctcaga gacacagagt gtggtggcag agacagaagg cagagagatc cctaaactca    1320
gaatcagctc ttttcgcaat gtaaacctat agaagtgaaa aacgggctca ccatgattga    1380
aaacaaatag gagacagagt tcagattgct cagaacccag gagatttcca gggacagccc    1440
agggctgctg gtgcttctgt aaggccatcg caagcttcag gttggcccag cgccccctcc    1500
cacagccttg ctccctccca cagcccgagg ctatataaac tcagctctcc agagcacagg    1560
ccagatctct tcctggacgg agctcagggc tgaaggaatt ggatggggac cgaaccatgg    1620
aagacgccaa aaacataaag aaaggcccgg cgccattcta ccgctggaa gatgaaccg     1680 ctggagagca actgcataag gctatgaaga gatacgccct ggttcctgga caattgctt    1740 ttacagatgc acatatcgag gtggacatca cttacgctga gtacttcgaa atgtccgttc    1800
ggttggcaga agctatgaaa cgatatgggc tgaatacaaa tcacagaatc gtcgtatgca    1860
gtgaaaactc tcttcaattc tttatgccgg tgttgggcgc gttatttatc ggagttgcag    1920
ttgcgcccgc gaacgacatt tataatgaac gtgaattgct caacagtatg ggcatttcgc    1980
agcctaccgt ggtgttcgtt tccaaaaagg ggttgcaaaa aatttttgaac gtgcaaaaaa    2040 agctcccaat catccaaaaa attattatca tggattctaa aacggattac cagggatttc    2100
agtcgatgta cacgttcgtc acatctcatc tacctcccgg ttttaatgaa tacgattttg    2160
tgccagagtc cttcgatagg gacaagacaa ttgcactgat catgaactcc tctggatcta    2220
ctggtctgcc taaggtgtc gctctgcctc atagaactgc ctgcgtgaga ttctcgcatg    2280
ccagagatcc tattttggc aatcaaatca ttccggatac tgcgatttta agtgttgttc    2340
cattccatca cggttttgga atgtttacta cactcggata tttgatatgt ggatttcgag    2400
tcgtcttaat gtatagattt gaagaagagc tgtttctgag gagccttcag gattacaaga    2460
ttcaaagtgc gctgctggtg ccaaccctat tctccttctt cgccaaaagc actctgattg    2520
acaaatacga tttatctaat ttacacgaaa ttgcttctgg tggcgctccc ctctctaagg    2580
aagtcgggga gcggttgcc aagaggttcc atctgccagg tatcaggcaa ggatatgggc    2640
tcactgagac tacatcagct attctgatta cacccgaggg ggatgataaa ccgggcgcgg    2700
tcggtaaagt tgttccattt tttgaagcga aggttgtgga tctggatacc gggaaaacgc    2760
tgggcgttaa tcaaagaggc gaactgtgtg tgagaggtcc tatgattatg tccggttatg    2820
taaacaatcc ggaagcgacc aacgccttga ttgacaagga tggatggcta cattctggag    2880
acatagctta ctgggacgaa gacgaacact tcttcatcgt tgaccgcctg aagtctctga    2940
ttaagtacaa aggctatcag gtggctcccg ctgaattgga atccatcttg ctccaacacc    3000
ccaacatctt cgacgcaggt gtcgcaggtc ttcccgacga tgacgccggt gaacttcccg    3060
ccgccgttgt tgttttggag cacggaaaga cgatgacgga aaaagagatc gtggattacg    3120
tcgccagtca agtaacaacc gcgaaaaagt tgcgcggagg agttgtgttt gtggacgaag    3180
taccgaaagg tcttaccgga aaactcgacg caagaaaaat cagagagatc ctcataaagg    3240
ccaagaaggg cggaaagatc gccgtgtaat tctagcggcc gctcgaggcc ggcaaggccg    3300 gatcacaaa caccattgtc acactccagt atacacaaac accattgtca cactccagat    3360
atcacaaaca ccattgtcac actccagaat tcggatccag acatgataag atacattgat    3420
```

```
gagtttggac aaaccacaac tagaatgcag tgaaaaaaat gctttatttg tgaaatttgt   3480
gatgctattg ctttatttgt aaccattata agctgcaata aacaagttaa caacaacaat   3540
tgcattcatt ttatgtttca ggttcagggg gaggtgtggg aggttttta aagcaagtaa    3600 aacctctaca aatgtggtat ggctgattat gatccggctg cctcgcgcgt ttcggtgatg   3660
acggtgaaaa cctctgacac atgcagctcc cggagacggt cacagcttgt ctgtaagcgg   3720
atgccgggag cagacaagcc cgtcaggcg cgtcagcggg tgttggcggg tgtcggggcg    3780
cagccatgag gtcgaccgta gataagtagc atggcgggtt aatcattaac tacaaggaac   3840
ccctagtgat ggagttggcc actccctctc tgcgcgctcg ctcgctcact gaggccgggc   3900
gaccaaaggt cgcccgacgc ccgggctttg cccgggcggc ctcagtgagc gagcgagcgc   3960
gccagctgaa gctatcagat ctgccggtct ccctatagtg agtcgtatta atttcgataa   4020
gccaggttaa cctgcattaa tgaatcggcc aacgcgcggg gagaggcggt ttgcgtattg   4080
ggcgctcttc cgcttcctcg ctcactgact cgctgcgctc ggtcgttcgg ctgcggcgag   4140
cggtatcagc tcactcaaag gcggtaatac ggttatccac agaatcaggg gataacgcag   4200
gaaagaacat gtgagcaaaa ggccagcaaa aggccaggaa ccgtaaaaag gccgcgttgc   4260
tggcgttttt ccataggctc cgcccccctg acgagcatca caaaaatcga cgctcaagtc   4320
agaggtggcg aaacccgaca ggactataaa gataccaggc gtttccccct ggaagctccc   4380
tcgtgcgctc tcctgttccg accctgccgc ttaccggata cctgtccgcc tttctccctt   4440
cgggaagcgt ggcgctttct catagctcac gctgtaggta tctcagttcg gtgtaggtcg   4500
ttcgctccaa gctgggctgt gtgcacgaac cccccgttca gcccgaccgc tgcgccttat   4560
ccggtaacta tcgtcttgag tccaacccgg taagacacga cttatcgcca ctggcagcag   4620
ccactggtaa caggattagc agagcgaggt atgtaggcgg tgctacagag ttcttgaagt   4680
ggtggcctaa ctacggctac actagaagaa cagtatttgg tatctgcgct ctgctgaagc   4740
cagttacctt cggaaaaaga gttggtagct cttgatccgg caaacaaacc accgctggta   4800
gcggtggttt ttttgtttgc aagcagcaga ttacgcgcag aaaaaaagga tctcaagaag   4860
atcctttgat cttttctacg gggtctgacg ctcagtggaa cgaaaactca cgttaaggga   4920
ttttggtcat gagattatca aaaaggatct tcacctagat ccttttaaat taaaaatgaa   4980
gttttaaatc aatctaaagt atatatgagt aaacttggtc tgacagttac caatgcttaa   5040
tcagtgaggc acctatctca gcgatctgtc tatttcgttc atccatagtt gcctgactcc   5100
ccgtcgtgta gataactacg atacgggagg gcttaccatc tggccccagt gctgcaatga   5160
taccgcgaga cccacgctca ccggctccag atttatcagc aataaaccag ccagccggaa   5220
gggccgagcg cagaagtggt cctgcaactt tatccgcctc catccagtct attaattgtt   5280
gccgggaagc tagagtaagt agttcgccag ttaatagttt cgcaacgtt gttgccattg    5340 ctacaggcat cgtggtgtca cgctcgtcgt ttggtatggc ttcattcagc tccggttccc   5400
aacgatcaag gcgagttaca tgatccccca tgttgtgcaa aaaagcggtt agctccttcg   5460
gtcctccgat cgttgtcaga agtaagttgg ccgcagtgtt atcactcatg gttatggcag   5520
cactgcataa ttctcttact gtcatgccat ccgtaagatg cttttctgtg actggtgagt   5580
actcaaccaa gtcattctga aatagtgta tgcggcgacc gagttgctct tgcccggcgt    5640
caatacggga taataccgcg ccacatagca gaactttaaa agtgctcatc attggaaaac   5700
gttcttcggg gcgaaaactc tcaaggatct taccgctgtt gagatccagt tcgatgtaac   5760
ccactcgtgc acccaactga tcttcagcat cttttacttt caccagcgtt tctgggtgag   5820
```

```
caaaaacagg aaggcaaaat gccgcaaaaa agggaataag ggcgacacgg aaatgttgaa      5880
tactcatact cttccttttt caatattatt gaagcattta tcagggttat tgtctcatga      5940
gcggatacat atttgaatgt atttagaaaa ataaacaaat aggggttccg cgcacatttc      6000
cccgaaaagt gccacctgac gtctaagaaa ccattattat catgacatta acctataaaa      6060
ataggcgtat cacgaggccc tttcgtctcg cgcgtttcgg tgatgacggt gaaaacctct      6120
gacacatgca gctcccggag acggtcacag cttgtctgta agcggatgcc gggagcagac      6180
aagcccgtca gggcgcgtca gcgggtgttg gcgggtgtcg ggctggctt  aactatgcgg      6240 catcagagca gattgtactg agagtgcacc atatggacat attgtcgtta  aacgcggct      6300 acaattaata cataaccta tgtatcatac acatacgatt taggtgacac tata           6354
```

<210> SEQ ID NO 4
<211> LENGTH: 5353
<212> TYPE: DNA
<213> ORGANISM: Artificial Sequence
<220> FEATURE:
<223> OTHER INFORMATION: plasmid with GFP and mouse periostin promoter

<400> SEQUENCE: 4

```
gaactcgatc gagcagctgc gcgctcgctc gctcactgag gccgcccggg caaagcccgg        60
gcgtcgggcg acctttggtc gcccggcctc agtgagcgag cgagcgcgca gagagggagt       120
ggccaactcc atcactaggg gttccttgta gttaatgatt aacccgccat gctacttatc       180
tacgtagcca tgctctagag acctctgtag gctggctggt gatactcaat tttatttcat       240
gtatacacaa cattttaaag atggaaatta gtacatgatt cttgatttaa attctttcaa       300
gctaacaatc tttttttttt ttttaaagtg gcctcagtca aagacactaa agatcaccga       360
gtcttgcata gagtttccat ttacaggact agagaaagct agtggagaca cagatcgggt       420
gcggaggtag tgagaagcac ttttcctaag aaggtgcagg gttgactcca aggcttggct       480
gggttataag agttacatgt attatttatt ctatatgtaa gcaacttttg agctcatgtg       540
ccatggcaac ctatggaccg catgttaata tagaagcatt ttaaaattag tgatacaatc       600
aagaccaagg gcatcctgct tatggtttgt gtgcacaggc ttacagagtg cagagtccgc       660
gaggagtccc agggactgct ggagtttgag gttggtttca cagtggtgag taagcgtggc       720
agtgtaatga cctcatggtc tcccgaggcc agataacaga gaactgccta taaatcagca       780
tgccgcggct agagagaaac ggccctgttt ctcagacaca ctatctctct tcagctacat       840
aatgaaccat ttctttctca gtaatgactt acatctctgg gtcagacttt gcagccctgg       900
aaagtcggac ttcatttttca tgatttccgt catcttcccg actggtagga aaattgcagg       960
ggtcagtagt gtcagcatag tttcacagag ctgaagagaa agggccctgt gtggagagcg      1020
acttttgatg agagccccgg aagagagtgt gcccttccgg ggattttttt cccagtctct      1080
tctacaactt cagctagcca attgaggggc atgtgtctct tccacataag ctgtggaaat      1140
cacactttaa atgcattgta catctatcca ggatttgggt taaatgcccc tgtgattttct     1200 cttctccgtg ttctgctgtg gagtgattta agtgcaatca gatcaaacca ggaaagtaac      1260
tgagctcaga gacacagagt gtggtggcag agacagaagg cagagagatc cctaaactca      1320
gaatcagctc ttttcgcaat gtaaacctat agaagtgaaa aacgggctca ccatgattga      1380
aaacaaatag gagacagagt tcagattgct cagaacccag gagatttcca gggacagccc      1440
agggctgctg gtgcttctgt aaggccatcg caagcttcag gttggcccag cgccccctcc      1500
```

```
cacagccttg ctccctccca cagcccagag ctatataaac tcagctctcc agagcacagg    1560
ccagatctct tcctggacgg agctcagggc tgaaggaatt ctgcagtcga cggtaccgcg    1620
ggcccgggat ccaccggtcg ccaccatggt gagcaagggc gaggagctgt tcaccggggt    1680
ggtgcccatc ctggtcgagc tggacggcga cgtaaacggc cacaagttca gcgtgtccgg    1740
cgagggcgag ggcgatgcca cctacggcaa gctgaccctg aagttcatct gcaccaccgg    1800
caagctgccc gtgccctggc ccaccctcgt gaccaccctg acctacggcg tgcagtgctt    1860
cagccgctac cccgaccaca tgaagcagca cgacttcttc aagtccgcca tgcccgaagg    1920
ctacgtccag gagcgcacca tcttcttcaa ggacgacggc aactacaaga cccgcgccga    1980
ggtgaagttc gagggcgaca ccctggtgaa ccgcatcgag ctgaagggca tcgacttcaa    2040
ggaggacggc aacatcctgg ggcacaagct ggagtacaac tacaacagcc acaacgtcta    2100
tatcatggcc gacaagcaga agaacggcat caaggtgaac ttcaagatcc gccacaacat    2160
cgaggacggc agcgtgcagc tcgccgacca ctaccagcag aacacccccca tcggcgacgg    2220 ccccgtgctg ctgcccgaca accactacct gagcacccag tccgccctga gcaaagaccc    2280
caacgagaag cgcgatcaca tggtcctgct ggagttcgtg accgccgccg ggatcactct    2340
cggcatggac gagctgtaca gtaaagcgg ccgctcgagg ccggcaaggc cggatccaga    2400
catgataaga tacattgatg agtttggaca accacaact agaatgcagt gaaaaaatg    2460 ctttatttgt gaaatttgtg atgctattgc tttatttgta accattataa gctgcaataa    2520
acaagttaac aacaacaatt gcattcattt tatgtttcag gttcagggg aggtgtggga    2580 ggttttttaa agcaagtaaa acctctacaa atgtggtatg ctgattatg atccggctgc    2640 ctcgcgcgtt tcggtgatga cggtgaaaac ctctgacaca tgcagctccc ggagacggtc    2700
acagcttgtc tgtaagcgga tgccgggagc agacaagccc gtcagggcgc gtcagcgggt    2760
gttggcgggt gtcggggcgc agccatgagg tcgaccgtag ataagtagca tggcgggtta    2820
atcattaact acaaggaacc cctagtgatg gagttggcca ctccctctct gcgcgctcgc    2880
tcgctcactg aggccgggcg accaaaggtc gcccgacgcc cgggctttgc ccgggcggcc    2940
tcagtgagcg agcgagcgcg ccagctgaag ctatcagatc tgccggtctc cctatagtga    3000
gtcgtattaa tttcgataag ccaggttaac ctgcattaat gaatcggcca acgcgcgggg    3060
agaggcggtt tgcgtattgg gcgctcttcc gcttcctcgc tcactgactc gctgcgctcg    3120
gtcgttcggc tgcggcgagc ggtatcagct cactcaaagg cggtaatacg ttatccaca    3180 gaatcagggg ataacgcagg aaagaacatg tgagcaaaag gccagcaaaa ggccaggaac    3240
cgtaaaaagg ccgcgttgct ggcgtttttc cataggctcc gcccccctga cgagcatcac    3300
aaaaatcgac gctcaagtca gaggtggcga aacccgacag gactataaag ataccaggcg    3360
tttccccctg gaagctccct cgtgcgctct cctgttccga ccctgccgct taccggatac    3420
ctgtccgcct ttctcccttc gggaagcgtg gcgctttctc atagctcacg ctgtaggtat    3480
ctcagttcgg tgtaggtcgt tcgctccaag ctgggctgtg tgcacgaacc ccccgttcag    3540
cccgaccgct gcgccttatc cggtaactat cgtcttgagt ccaacccggt aagacacgac    3600
ttatcgccac tggcagcagc cactggtaac aggattagca gagcgaggta tgtaggcggt    3660
gctacagagt tcttgaagtg gtggcctaac tacggctaca ctagaagaac agtatttggt    3720
atctgcgctc tgctgaagcc agttaccttc ggaaaaagag ttggtagctc ttgatccggc    3780
aaacaaacca ccgctggtag cggtggtttt tttgtttgca agcagcagat tacgcgcaga    3840
aaaaaaggat ctcaagaaga tcctttgatc ttttctacgg ggtctgacgc tcagtggaac    3900
```

```
gaaaactcac gttaagggat tttggtcatg agattatcaa aaaggatctt cacctagatc      3960
cttttaaatt aaaaatgaag ttttaaatca atctaaagta tatatgagta aacttggtct      4020
gacagttacc aatgcttaat cagtgaggca cctatctcag cgatctgtct atttcgttca      4080
tccatagttg cctgactccc cgtcgtgtag ataactacga tacgggaggg cttaccatct      4140
ggccccagtg ctgcaatgat accgcgagac ccacgctcac cggctccaga tttatcagca      4200
ataaaccagc cagccggaag ggccgagcgc agaagtggtc ctgcaacttt atccgcctcc      4260
atccagtcta ttaattgttg ccgggaagct agagtaagta gttcgccagt taatagtttg      4320
cgcaacgttg ttgccattgc tacaggcatc gtggtgtcac gctcgtcgtt tggtatggct      4380
tcattcagct ccggttccca acgatcaagg cgagttacat gatcccccat gttgtgcaaa      4440
aaagcggtta gctccttcgg tcctccgatc gttgtcagaa gtaagttggc cgcagtgtta      4500
tcactcatgg ttatggcagc actgcataat tctcttactg tcatgccatc cgtaagatgc      4560
ttttctgtga ctggtgagta ctcaaccaag tcattctgag aatagtgtat gcggcgaccg      4620
agttgctctt gcccggcgtc aatacgggat aataccgcgc cacatagcag aactttaaaa      4680
gtgctcatca ttggaaaacg ttcttcgggg cgaaaactct caaggatctt accgctgttg      4740
agatccagtt cgatgtaacc cactcgtgca cccaactgat cttcagcatc ttttactttc      4800
accagcgttt ctgggtgagc aaaaacagga aggcaaaatg ccgcaaaaaa gggaataagg      4860
gcgacacgga aatgttgaat actcatactc ttcctttttc aatattattg aagcatttat      4920
cagggttatt gtctcatgag cggatacata tttgaatgta tttagaaaaa taaacaaata      4980
ggggttccgc gcacatttcc ccgaaaagtg ccacctgacg tctaagaaac cattattatc      5040
atgacattaa cctataaaaa taggcgtatc acgaggccct ttcgtctcgc gcgtttcggt      5100
gatgacggtg aaaacctctg acacatgcag ctcccggaga cggtcacagc ttgtctgtaa      5160
gcggatgccg ggagcagaca gcccgtcag ggcgcgtcag cgggtgttgg cgggtgtcgg      5220
ggctggctta actatgcggc atcagagcag attgtactga gagtgcacca tatggacata      5280
ttgtcgttag aacgcggcta caattaatac ataaccttat gtatcataca catacgattt      5340
aggtgacact ata                                                         5353
```

<210> SEQ ID NO 5
<211> LENGTH: 5740
<212> TYPE: DNA
<213> ORGANISM: Artificial Sequence
<220> FEATURE:
<223> OTHER INFORMATION: plasmid with cre, mouse periostin promoter, and
      mammalian miR122

<400> SEQUENCE: 5

```
gaactcgatc gagcagctgc gcgctcgctc gctcactgag gccgcccggg caaagcccgg        60
gcgtcgggcg acctttggtc gcccggcctc agtgagcgag cgagcgcgca gagagggagt       120
ggccaactcc atcactaggg gttccttgta gttaatgatt aacccgccat gctacttatc       180
tacgtagcca tgctctagag acctctgtag gctggctggt gatactcaat tttatttcat       240
gtatacacaa cattttaaag atggaaatta gtacatgatt cttgatttaa attcttttcaa      300 gctaacaatc ttttttttttt ttttaaagtg gcctcagtca aagacactaa agatcaccga      360
gtcttgcata gagtttccat ttacaggact agagaaagct agtggagaca cagatcgggt      420
gcggaggtag tgagaagcac ttttcctaag aaggtgcagg gttgactcca aggcttggct      480
gggttataag agttacatgt attatttatt ctatatgtaa gcaactttgt agctcatgtg      540
```

```
ccatggcaac ctatggaccg catgttaata tagaagcatt ttaaaattag tgatacaatc    600
aagaccaagg gcatcctgct tatggttttgt gtgcacaggc ttacagagtg cagagtccgc    660
gaggagtccc agggactgct ggagtttgag gttggtttca cagtggtgag taagcgtggc    720
agtgtaatga cctcatggtc tcccgaggcc agataacaga gaactgccta taatcagca    780 tgccgcggct agagagaaac ggccctgttt ctcagacaca ctatctctct tcagctacat    840
aatgaaccat ttctttctca gtaatgactt acatctctgg gtcagacttt gcagccctgg    900
aaagtcggac ttcattttca tgatttccgt catcttcccg actggtagga aaattgcagg    960
ggtcagtagt gtcagcatag tttcacagag ctgaagagaa agggccctgt gtggagagcg   1020
acttttgatg agagccccgg aagagagtgt gcccttccgg ggattttttt cccagtctct   1080
tctacaactt cagctagcca attgaggggc atgtgtctct tccacataag ctgtggaaat   1140
cacactttaa atgcattgta catctatcca ggatttgggt taaatgcccc tgtgatttct   1200
cttctccgtg ttctgctgtg gagtgattta agtgcaatca gatcaaacca ggaaagtaac   1260
tgagctcaga gacacagagt gtggtggcag agacagaagg cagagagatc cctaaactca   1320
gaatcagctc ttttcgcaat gtaaacctat agaagtgaaa aacgggctca ccatgattga   1380
aaacaaatag gagacagagt tcagattgct cagaacccag gagatttcca gggacagccc   1440
agggctgctg gtgcttctgt aaggccatcg caagcttcag gttggcccag cgccccctcc   1500
cacagccttg ctccctccca gcccagag ctatataaac tcagctctcc agagcacagg   1560
ccagatctct tcctggacgg agctcagggc tgaaggaatt cgatggggac cgaaaagctt   1620
gtccaccatg gtgcccaaga agaagaggaa agtctccaac ctgctgactg tgcaccaaaa   1680
cctgcctgcc ctccctgtgg atgccacctc tgatgaagtc aggaagaacc tgatggacat   1740
gttcagggac aggcaggcct tctctgaaca cacctggaag atgctcctgt ctgtgtgcag   1800
atcctgggct gcctggtgca agctgaacaa caggaaatgg ttccctgctg aacctgagga   1860
tgtgagggac tacctcctgt acctgcaagc cagaggcctg gctgtgaaga ccatccaaca   1920
gcacctgggc cagctcaaca tgctgcacag gagatctggc ctgcctcgcc cttctgactc   1980
caatgctgtg tccctggtga tgaggagaat cagaaaggag aatgtggatg ctggggagag   2040
agccaagcag gccctggcct ttgaacgcac tgactttgac caagtcagat ccctgatgga   2100
gaactctgac agatgccagg acatcaggaa cctggccttc ctgggcattg cctacaacac   2160
cctgctgcgc attgccgaaa ttgccagaat cagagtgaag gacatctccc gcaccgatgg   2220
tgggagaatg ctgatccaca ttggcaggac caagaccctg gtgtccacag ctggtgtgga   2280
gaaggccctg tccctggggg ttaccaagct ggtggagaga tggatctctg tgtctggtgt   2340
ggctgatgac cccaacaact acctgttctg ccgggtcaga aagaatggtg tggctgcccc   2400
ttctgccacc tcccaactgt ccacccgggc cctggaaggg atctttgagg ccacccaccg   2460
cctgatctat ggtgccaagg atgactctgg gcagagatac ctggcctggt ctggccactc   2520
tgccagagtg ggtgctgcca gggacatggc cagggctggt gtgtccatcc ctgaaatcat   2580
gcaggctggt ggctggacca atgtgaacat tgtgatgaac tacatcagaa acctggactc   2640
tgagactggg gccatggtga ggctgctcga ggatggggac tgaaaggatc cacaaacacc   2700
attgtcacac tccagtatac acaaacacca ttgtcacact ccagatatca caaacaccat   2760
tgtcacactc cagaattcgg atccagacat gataagatac attgatgagt ttggacaaac   2820
cacaactaga atgcagtgaa aaaaatgctt tatttgtgaa atttgtgatg ctattgcttt   2880
```

```
atttgtaacc attataagct gcaataaaca agttaacaac acaattgca ttcattttat    2940 gtttcaggtt caggggagg tgtgggaggt tttttaaagc aagtaaaacc tctacaaatg    3000
tggtatggct gattatgatc cggctgcctc gcgcgtttcg gtgatgacgg tgaaaacctc    3060
tgacacatgc agctcccgga gacggtcaca gcttgtctgt aagcggatgc cgggagcaga    3120
caagcccgtc agggcgcgtc agcgggtgtt ggcgggtgtc ggggcgcagc catgaggtcg    3180
accgtagata agtagcatgg cgggttaatc attaactaca aggaacccct agtgatggag    3240
ttggccactc cctctctgcg cgctcgctcg ctcactgagg ccgggcgacc aaaggtcgcc    3300
cgacgcccgg gctttgcccg gcggcctca gtgagcgagc gagcgcgcca gctgaagcta     3360
tcagatctgc cggtctccct atagtgagtc gtattaattt cgataagcca ggttaacctg    3420
cattaatgaa tcggccaacg cgcggggaga ggcggtttgc gtattgggcg ctcttccgct    3480
tcctcgctca ctgactcgct gcgctcggtc gttcggctgc ggcgagcggt atcagctcac    3540
tcaaaggcgg taatacggtt atccacagaa tcagggata acgcaggaaa gaacatgtga     3600
gcaaaaggcc agcaaaaggc caggaaccgt aaaaaggccg cgttgctggc gttttccat     3660 aggctccgcc cccctgacga gcatcacaaa aatcgacgct caagtcagag gtggcgaaac    3720
ccgacaggac tataaagata ccaggcgttt ccccctggaa gctccctcgt gcgctctcct    3780
gttccgaccc tgccgcttac cggatacctg tccgcctttc tcccttcggg aagcgtggcg    3840 cttctctcata gctcacgctg taggtatctc agttcggtgt aggtcgttcg ctccaagctg    3900
ggctgtgtgc acgaaccccc cgttcagccc gaccgctgcg ccttatccgg taactatcgt    3960
cttgagtcca acccggtaag acacgactta tcgccactgg cagcagccac tggtaacagg    4020
attagcagag cgaggtatgt aggcggtgct acagagttct tgaagtggtg gcctaactac    4080
ggctacacta agaacagt atttggtatc tgcgctctgc tgaagccagt taccttcgga     4140 aaagagttg gtagctcttg atccggcaaa caaaccaccg ctggtagcgg tggttttttt    4200
gtttgcaagc agcagattac gcgcagaaaa aaggatctc aagaagatcc tttgatcttt     4260
tctacggggt ctgacgctca gtggaacgaa aactcacgtt aagggatttt ggtcatgaga    4320
ttatcaaaaa ggatcttcac ctagatcctt ttaaattaaa aatgaagttt taaatcaatc    4380
taaagtatat atgagtaaac ttggtctgac agttaccaat gcttaatcag tgaggcacct    4440
atctcagcga tctgtctatt tcgttcatcc atagttgcct gactccccgt cgtgtagata    4500
actacgatac gggagggctt accatctggc cccagtgctg caatgatacc gcgagaccca    4560
cgctcaccgg ctccagattt atcagcaata aaccagccag ccggaagggc cgagcgcaga    4620
agtggtcctg caactttatc cgcctccatc cagtctatta attgttgccg ggaagctaga    4680
gtaagtagtt cgccagttaa tagtttgcgc aacgttgttg ccattgctac aggcatcgtg    4740
gtgtcacgct cgtcgtttgg tatggcttca ttcagctccg gttcccaacg atcaaggcga    4800
gttacatgat cccccatgtt gtgcaaaaaa gcggttagct ccttcggtcc tccgatcgtt    4860
gtcagaagta agttggccgc agtgttatca ctcatggtta tggcagcact gcataattct    4920
cttactgtca tgccatccgt aagatgcttt tctgtgactg gtgagtactc aaccaagtca    4980
ttctgagaat agtgtatgcg gcgaccgagt tgctcttgcc cggcgtcaat acgggataat    5040
accgcgccac atagcagaac tttaaaagtg ctcatcattg gaaaacgttc ttcggggcga    5100
aaactctcaa ggatcttacc gctgttgaga tccagttcga tgtaacccac tcgtgcaccc    5160
aactgatctt cagcatcttt tactttcacc agcgtttctg ggtgagcaaa aacaggaagg    5220
caaaatgccg caaaaaaggg aataagggcg acacggaaat gttgaatact catactcttc    5280
```

| cttttttcaat attattgaag catttatcag ggttattgtc tcatgagcgg atacatattt | 5340 |
| gaatgtattt agaaaaataa acaaataggg gttccgcgca catttccccg aaaagtgcca | 5400 |
| cctgacgtct aagaaaccat tattatcatg acattaacct ataaaaatag gcgtatcacg | 5460 |
| aggccctttc gtctcgcgcg tttcggtgat gacggtgaaa acctctgaca catgcagctc | 5520 |
| ccggagacgg tcacagcttg tctgtaagcg gatgccggga gcagacaagc ccgtcagggc | 5580 |
| gcgtcagcgg gtgttggcgg gtgtcggggc tggcttaact atgcggcatc agagcagatt | 5640 |
| gtactgagag tgcaccatat ggacatattg tcgttagaac gcggctacaa ttaatacata | 5700 |
| accttatgta tcatacacat acgatttagg tgacactata | 5740 |

```
<210> SEQ ID NO 6
<211> LENGTH: 1395
<212> TYPE: DNA
<213> ORGANISM: Mus musculus

<400> SEQUENCE: 6
```

| gacctctgta ggctggctgg tgatactcaa ttttatttca tgtatacaca acattttaaa | 60 |
| gatggaaatt agtacatgat tcttgattta aattcttttca agctaacaat ctttttttttt | 120 |
| tttttaaagt ggcctcagtc aaagacacta aagatcaccg agtcttgcat agagtttcca | 180 |
| tttacaggac tagagaaagc tagtggagac acagatcggg tgcggaggta gtgagaagca | 240 |
| cttttcctaa gaaggtgcag ggttgactcc aaggcttggc tgggttataa gagttacatg | 300 |
| tattatttat tctatatgta agcaactttt gagctcatgt gccatggcaa cctatggacc | 360 |
| gcatgttaat atagaagcat tttaaaatta gtgatacaat caagaccaag gcatcctgc | 420 |
| ttatggtttg tgtgcacagg cttacagagt gcagagtccg cgaggagtcc cagggactgc | 480 |
| tggagtttga ggttggtttc acagtggtga gtaagcgtgg cagtgtaatg acctcatggt | 540 |
| ctcccgaggc cagataacag agaactgcct ataaatcagc atgccgcggc tagagagaaa | 600 |
| cggccctgtt tctcagacac actatctctc ttcagctaca taatgaacca tttcttctc | 660 |
| agtaatgact tacatctctg ggtcagactt tgcagccctg gaaagtcgga cttcatttc | 720 |
| atgatttccg tcatcttccc gactggtagg aaaattgcag gggtcagtag tgtcagcata | 780 |
| gtttcacaga gctgaagaga aagggccctg tgtggagagc acttttgat gagagccccg | 840 |
| gaagagagtg tgcccttccg gggatttttt tcccagtctc ttctacaact tcagctagcc | 900 |
| aattgagggg catgtgtctc ttccacataa gctgtggaaa tcacacttta aatgcattgt | 960 |
| acatctatcc aggatttggg ttaaatgccc ctgtgatttc tcttctccgt gttctgctgt | 1020 |
| ggagtgattt aagtgcaatc agatcaaacc aggaaagtaa ctgagctcag agacacagag | 1080 |
| tgtggtggca gagacagaag gcagagagat ccctaaactc agaatcagct cttttcgcaa | 1140 |
| tgtaaaccta tagaagtgaa aaacgggctc accatgattg aaaacaaata ggagacagag | 1200 |
| ttcagattgc tcagaaccca ggagatttcc agggacagcc cagggctgct ggtgcttctg | 1260 |
| taaggccatc gcaagcttca ggttggccca gcgccccctc ccacagcctt gctccctccc | 1320 |
| acagcccaga gctatataaa ctcagctctc cagagcacag gccagatctc ttcctggacg | 1380 |
| gagctcaggg ctgaa | 1395 |

```
<210> SEQ ID NO 7
<211> LENGTH: 4683
<212> TYPE: DNA
<213> ORGANISM: adeno-associated virus 6
```

<400> SEQUENCE: 7

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagcgcca tgccggggtt ttacgagatt gtgattaagg tccccagcga     360
ccttgacgag catctgcccg gcatttctga cagctttgtg aactgggtgg ccagaaagga     420
atgggagttg ccgccagatt ctgacatgga tctgaatctg attgagcagg caccctgac      480
cgtggccgag aagctgcagc gcgacttcct ggtccagtgg cgccgcgtga gtaaggcccc     540
ggaggccctc ttctttgttc agttcgagaa gggcgagtcc tacttccacc tccatattct     600
ggtggagacc acgggggtca atccatggt  gctgggccgc ttcctgagtc agattaggga     660
caagctggtg cagaccatct accgcgggat cgagccgacc ctgcccaact ggttcgcggt     720
gaccaagacg cgtaatggcg ccggagggg  gaacaaggtg gtggacgagt gctacatccc     780
caactacctc ctgcccaaga ctcagcccga gctgcagtgg gcgtggacta acatggagga     840
gtatataagc gcgtgtttaa acctggccga gcgcaaacgg ctcgtggcgc acgacctgac     900
ccacgtcagc cagacccagg agcagaacaa ggagaatctg aacccccaatt ctgacgcgcc    960
tgtcatccgg tcaaaaacct ccgcacgcta catggagctg gtcgggtggc tggtggaccg    1020
gggcatcacc tccgagaagc agtggatcca ggaggaccag gcctcgtaca tctccttcaa    1080
cgccgcctcc aactcgcggt cccagatcaa ggccgctctg acaatgccgg caagatcat     1140
ggcgctgacc aaatccgcgc ccgactacct ggtaggcccc gctccgcccg ccgacattaa    1200
aaccaaccgc atttaccgca tcctggagct gaacggctac gaccctgcct acgccggctc    1260
cgtcttctc  ggctgggccc agaaaaggtt cggaaaacgc aacaccatct ggctgtttgg    1320
gccggccacc acgggcaaga ccaacatcgc ggaagccatc gcccacgccg tgcccttcta    1380
cggctgcgtc aactgaacca atgagaactt tcccttcaac gattgcgtcg acaagatggt    1440
gatctggtgg gaggagggca agatgacggc caaggtcgtg gagtccgcca aggccattct    1500
cggcggcagc aaggtgcgcg tggaccaaaa gtgcaagtcg tccgcccaga tcgatcccac    1560
ccccgtgatc gtcacctcca acaccaacat gtgcgccgtg attgacggga acagcaccac    1620
cttcgagcac cagcagccgt tgcaggaccg gatgttcaaa tttgaactca cccgccgtct    1680
ggagcatgac tttggcaagg tgacaaagca ggaagtcaaa gagttcttcc gctgggcgca    1740
ggatcacgtg accgaggtgg cgcatgagtt ctacgtcaga aagggtggag ccaacaagag    1800
acccgccccc gatgacgcgg ataaaagcga gcccaagcgg gcctgcccct cagtcgcgga    1860
tccatcgacg tcagacgcgg aaggagctcc ggtggacttt gccgacaggt accaaaaacaa   1920
atgttctcgt cacgcgggca tgcttcagat gctgtttccc tgcaaaacat gcgagagaat    1980
gaatcagaat ttcaacattt gcttcacgca cgggaccaga gactgttcag aatgtttccc    2040
cggcgtgtca gaatctcaac cggtcgtcag aaagaggacg tatcggaaac tctgtgccat    2100
tcatcatctg ctggggcggg ctcccgagat tgcttgctcg gcctgcgatc tggtcaacgt    2160
ggatctggat gactgtgttt ctgagcaata aatgacttaa accaggtatg gctgccgatg    2220
gttatcttcc agattggctc gaggacaacc tctctgaggg cattcgcgag tggtgggact    2280
tgaaacctgg agccccgaaa cccaaagcca accagcaaaa gcaggacgac ggccggggtc    2340
```

```
tggtgcttcc tggctacaag tacctcggac ccttcaacgg actgacaag ggggagcccg    2400 tcaacgcggc ggatgcagcg gccctcgagc acgacaaggc ctacgaccag cagctcaaag    2460
cgggtgacaa tccgtacctg cggtataacc acgccgacgc cgagtttcag gagcgtctgc    2520
aagaagatac gtcttttggg ggcaacctcg ggcgagcagt cttccaggcc aagaagaggg    2580
ttctcgaacc ttttggtctg gttgaggaag gtgctaagac ggctcctgga agaaacgtc     2640 cggtagagca gtcgccacaa gagccagact cctcctcggg cattggcaag acaggccagc    2700
agcccgctaa aaagagactc aattttggtc agactggcga ctcagagtca gtccccgacc    2760
cacaacctct cggagaacct ccagcaaccc ccgctgctgt gggacctact acaatggctt    2820
caggcggtgg cgcaccaatg gcagacaata cgaaggcgc cgacggagtg ggtaatgcct     2880
caggaaattg gcattgcgat tccacatggc tgggcgacga gtcatcacc accagcaccc     2940 gaacatgggc cttgcccacc tataacaacc acctctacaa gcaaatctcc agtgcttcaa    3000
cgggggccag caacgacaac cactacttcg gctacagcac cccctggggg tattttgatt    3060
tcaacagatt ccactgccat ttctcaccac gtgactggca gcgactcatc aacaacaatt    3120
ggggattccg gccaagagag ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tccttttact gcctggaata tttcccatcg cagatgctga    3420
gaacgggcaa taactttacc ttcagctaca ccttcgagga cgtgccttc cacagcagct     3480 acgcgcacag ccagagcctg gaccggctga tgaatcctct catcgaccag tacctgtatt    3540
acctgaacag aactcagaat cagtccggaa gtgcccaaaa caaggacttg ctgtttagcc    3600
gggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataacctt aatgggcgtg aatctataat caaccctggc actgctatgg    3780
cctcacacaa agacgacaaa gacaagttct ttcccatgag cggtgtcatg attttggaa     3840 aggagagcgc cggagcttca aacactgcat tggacaatgt catgatcaca gacgaagagg    3900
aaatcaaagc cactaacccc gtggccaccg aaagattggg gactgtggca gtcaatctcc    3960
agagcagcag cacagaccct gcgaccggag atgtgcatgt tatgggagcc ttacctggaa    4020
tggtgtggca agacagagac gtatacctgc agggtcctat ttgggccaaa attcctcaca    4080
cggatggaca cttccacccg tctcctctca tgggcggctt tggacttaag caccgcctc     4140 ctcagatcct catcaaaac acgcctgttc ctgcgaatcc tccggcagag ttttcggcta    4200
caaagtttgc ttcattcatc acccagtatt ccacaggaca agtgagcgtg gagattgaat    4260
gggagctgca gaaagaaaac agcaaacgct ggaatcccga agtgcagtat acatctaact    4320
atgcaaaatc tgccaacgtt gatttcactg tggacaacaa tggactttat actgagcctc    4380
gccccattgg cacccgttac ctcacccgtc cctgtaatt gtgtgttaat caataaaccg     4440
gttaattcgt gtcagttgaa ctttggtctc atgtcgttat tatcttatct ggtcaccata    4500
gcaaccggtt acacattaac tgcttagttg cgcttcgcga ataccctag tgatggagtt     4560 gcccactccc tctatgcgcg ctcgctcgct cggtggggcc ggcagagcag agctctgccg    4620
tctgcggacc tttggtccgc aggccccacc gagcgagcga gcgcgcatag agggagtggg    4680
```

-continued

```
caa                                                                    4683

<210> SEQ ID NO 8
<211> LENGTH: 24
<212> TYPE: DNA
<213> ORGANISM: Mus musculus

<400> SEQUENCE: 8
tccgtgttct gctgtggagt gatt                                               24

<210> SEQ ID NO 9
<211> LENGTH: 24
<212> TYPE: DNA
<213> ORGANISM: Mus musculus

<400> SEQUENCE: 9
tagggatctc tctgccttct gtct                                               24
```

COMPOSITIONS AND METHODS FOR ADENO-ASSOCIATED VIRUS MEDIATED GENE EXPRESSION IN MYOFIBROBLAST-LIKE CELLS

CROSS REFERENCE TO RELATED APPLICATIONS

This application is a national stage filing of International Application No. PCT/US2017/020113, filed Mar. 1, 2017, which is entitled to priority pursuant to 35 U.S.C. § 119(e) to U.S. provisional patent application No. 62/301,985, filed on Mar. 1, 2016 the disclosures of which are incorporated by reference in their entirety herein.

BACKGROUND

Adeno-associated virus (AAV) has been used to program gene expression in a variety of tissues, including heart, liver, skeletal muscle, brain, kidney and lung.[1,2] AAV9, in particular, provides highly efficient transduction in cardiac muscle.[3,4] However, it has not previously been shown to transduce fibroblasts in vivo, including cardiac fibroblasts.

Studies by Zak[5] and Nag[6] demonstrated that fibroblasts account for over half of the cardiac cell population in adult rats, although more recent studies have shown that this fraction is lower in mice.[7] While cardiac fibroblasts are normally quiescent in the heart, after injury they differentiate into myofibroblasts, which are integral to the post-myocardial infarction (MI) wound healing process.[8,9] After MI, myofibroblasts infiltrate the infarct zone, where they contribute to scar formation through collagen deposition and the secretion of cytokines, matrix metalloproteinases, and growth factors.[7,10] While this normal healing response is crucial to prevent cardiac rupture, it generates non-contractile scar instead of regenerating viable myocardium. As a result, infarct-targeted therapies are needed to reprogram the post-infarct healing process away from scar formation and towards cardiac regeneration.[7,11,12] Previous studies have targeted gene therapy to cardiomyocytes,[11] but the ability to modulate myofibroblast behavior would open new avenues of therapy to treat LV remodeling in patients recovering from MI.

Several serotypes of AAV have been used to transduce fibroblasts in vitro. Studies using AAV6, -8 and -9 in cultures of human corneal fibroblasts have demonstrated 25-50 fold greater transgene expression using AAV6 as compared to the other two serotypes.[13] However, despite this success in cell culture, AAV has not been shown to efficiently transduce fibroblasts, cardiac or otherwise, in vivo. Because a variety of AAV serotypes transduce cardiomyocytes after systemic administration,[2,14] any therapy aimed at cardiac fibroblasts would benefit from a promoter that minimizes transcription of exogenous genes in cardiomyocytes to avoid off-target effects. Lindsley et al. dissected a 3.9 kilobase promoter responsible for controlling the transcription of periostin, an epithelial ligand and matricellular protein commonly expressed by fibroblasts.[9,15,16]

There is a long felt need in the art for compositions and methods useful for treating myocardial infarction and similar cardiac injuries, diseases, and disorders. The present invention satisfies these needs.

SUMMARY OF THE INVENTION

Although AAV has been used previously to direct gene transfer to a variety of tissues, it has not been shown to effectively target fibroblasts in vivo, including cardiac fibroblasts. The present application discloses that systemic injection of a recombinant AAV vector comprising a promoter targets gene expression to a myofibroblast-like lineage of cell in the heart. Unexpectedly, recombinant AAV9 provided expression in a greater number of cells than did AAV6. Previous work indicated that AAV6 is the vector of choice (Ellis et al., 2013, Virology Journal 10:74).

The present application also discloses the preparation and use of AAV expression cassettes using a modified periostin promoter that successfully drives gene expression in cardiac myofibroblast-like cells. The present application is the first to identify and disclose the unexpected result of AAV9-mediated expression of genes in a myofibroblast-like lineage of heart cells. The present invention therefore encompasses compositions and methods useful for treating myocardial infarction and using gene therapy to treat subjects surviving myocardial infarction.

The present application discloses compositions and methods for preparing and using AAV vectors that are useful for targeting cells and inducing gene expression. In one aspect, the targeted cells are cardiac fibroblasts. In one aspect, the cells are cardiac myofibroblasts or myofibroblast-like cells that express one or more myofibroblast markers. Therefore, the present invention provides compositions and methods for selective gene expression in cardiac myofibroblast-like cells.

The compositions and methods of the invention are useful for efficiently targeting cardiac myofibroblasts following a cardiac injury, disease, or disorder.

The present invention encompasses a system for targeting gene expression to myofibroblast-like cells. In one aspect, the system is a recombinant AAV vector comprising at least one promoter. In one aspect it also comprises at least one gene to be expressed in the target cell. In one aspect, the cells are cardiac myofibroblast-like cells. In one aspect, the system is useful for genetically reprogramming cardiac regeneration. In one aspect the regeneration is after myocardial infarction. In one aspect, the regeneration begins shortly after myocardial infarction. In one aspect, the system is useful for reducing LV remodeling.

In one embodiment, the periostin promoter AAV vector induces gene expression in vivo. In one aspect, the periostin promoter mediates gene expression in the infarct zone of a heart. In one aspect, the periostin promoter mediates gene expression in the border zone of an infarcted heart.

In one embodiment, the promoter used does not transcribe exogenous genes in cardiomyocytes.

In one embodiment, a promoter of the invention minimizes exogenous gene expression in cardiomyocytes.

In one embodiment, a promoter of the invention is useful for minimizing endogenous gene expression in cardiomyocytes. In one embodiment, the promoter useful for minimizing endogenous gene expression in cardiomyocytes is a second promoter. When treating, for example, wound healing following myocardial infarction, a recombinant AAV vector of the invention can be administered at varying times to either stimulate or inhibit certain functions. That is, the recombinant AAV vector can be engineered by varying the promoter and/or therapeutic genes of the vector to address the particular stated of healing and whether cells such as cardiomyocytes or myofibroblasts need to have certain genes stimulated or suppressed. This can be coupled with co-administration of additional therapeutic agents. Additionally, with each administration a different iteration of the recombinant AAV vector can be used depending on the cell or gene to be regulated at that time.

A recombinant AAV vector of the invention may comprise other types of genes or sequences including, but not limited to, siRNA, shRNA, miRNA, and antagomirs.

In one embodiment, the promoter is used to express one or more antagomirs to coordinate the de-repression of a gene network. In one embodiment, the promoter is used to minimize endogenous gene expression in cardiomyocytes using one or more siRNAs, shRNAs, miRNAs, antagomirs, etc. directed against one or more cardiomyocyte genes of interest. In one aspect, a second promoter is used for siRNAs, shRNAs, miRNAs, antagomirs, etc. directed against one or more cardiomyocyte genes of interest.

The present invention encompasses the use of other promoters that will work in a manner similar to periostin in the same AAV in that fibroblasts or myofibroblasts are preferentially targeted over cardiomyocytes, particularly in terms of induced gene expression.

The present invention provides compositions and methods useful for treating a cardiac ischemic reperfusion injury or other cardiac injury, disease, or disorder. The method comprises administering to a subject in need thereof a pharmaceutical composition comprising an effective amount of a recombinant AAV comprising a regulatory element active in cardiac myofibroblasts. In one aspect, the regulatory element comprises at least one promoter element and optionally at least one enhancer element. In one aspect, the promoter minimizes exogenous gene expression in cardiomyocytes or does not transcribe exogenous genes in cardiomyocytes. In one aspect, the recombinant AAV vector comprises one or more genes operably linked to a promoter element. In one aspect, the promoter is a periostin promoter. In one aspect, the periostin promoter is a mammalian promoter. In one aspect, the periostin promoter is a human periostin promoter.

In one embodiment, the present invention provides a series of strategies to enhance wound healing. In one aspect, a series of injections of recombinant AAV vectors can be used. In one aspect, additional therapeutic agents are administered. Depending on the stage of the injury or of the wound healing process, the recombinant AAV can be varied, such as by using different therapeutic genes in the vector, by the used of additional growth factors, cytokines, drugs, etc., or by the use of inhibitors of specific genes or proteins.

In one embodiment, a recombinant AAV vector of the invention is administered to a subject after myocardial infarction in the subject.

In one embodiment, a recombinant AAV vector of the invention is administered after reperfusion occurs.

In one embodiment, a recombinant AAV vector of the invention is administered along with an additional therapeutic agent. In one aspect, the additional therapeutic agent is a biomolecule and in another aspect it is a drug. In one aspect, a biomolecule and a drug are co-administered with the recombinant AAV vector of the invention.

One of ordinary skill in the art will appreciate that depending on factors such as the age, sex, health, of the subject or the particular injury or disease being prevented or treated that the recombinant AAV vector can be administered in varying quantities, at different times, and various means. In one aspect, a recombinant AAV vector of the invention can be administered systemically, intravenously, by intracoronary infusion, locally, topically, or by direct injection into myocardium.

In one embodiment, the AAV is AAV6, AAV8, or AAV9. In one aspect, AAV6 consists of SEQ ID NO:7. In one aspect, AAV8 consists of SEQ ID NO:2. In one aspect, AAV9 consists of SEQ ID NO:1. In one aspect, the invention comprises the use of any AAV that can be used as a recombinant vector achieve the selective results disclosed herein for targeting gene expression to cardiac myofibroblasts but not other cardiac cells, including cardiomyocytes. In one aspect, the rAAV of the invention minimizes exogenous gene expression in cardiomyocytes or does not transcribe exogenous genes in cardiomyocytes.

In one embodiment a useful promoter/enhancer of the invention is the 1395 bp (SEQ ID NO:6), which is a combination of promoter and enhancer. In one aspect, the promoter/enhancer is an effective fragment of homolog of SEQ ID NO:6.

Plasmids useful for the practice of the invention include, but are not limited to, those described and used herein such as those having SEQ ID NOs:3, 4, and 5. These plasmids comprise, for examples, useful promoters and enhancers.

In one aspect, the regulatory element of the recombinant AAV vector increases expression of the therapeutic gene in the targeted tissue. In one aspect, the regulatory element comprises at least one enhancer element and at least one promoter element. In one aspect, the regulatory element comprises at least one promoter element. In one aspect, the regulatory element comprises one enhancer element and one promoter element. In one aspect, the regulatory element is one promoter element.

In one aspect, a gene or therapeutic gene or sequence of the invention is a structural gene. In one aspect, a structural gene's transcription is under the control of a promoter, which is operably linked thereto.

In one embodiment, the AAV vector comprises at least one therapeutic gene operably linked to at least one promoter element, or active fragments, modifications, or homologs thereof. In one aspect, it is useful for targeting and transducing cardiac myofibroblasts.

In one embodiment, the recombinant AAV vector comprises at least one therapeutic gene operably linked to at least one promoter element, or active fragments, modifications, or homologs thereof.

In one embodiment, the recombinant AAV vector comprises at least one reporter gene operably linked to at least one promoter element, or active fragments, modifications, or homologs thereof. In one aspect, the recombinant AAV vector also comprises a therapeutic gene.

In one aspect, a vector of the invention preferentially targets an infarct area. In one aspect, the infarct area is the infarct border zone. In one aspect, myofibroblasts in an infarct border zone are preferentially targeted over similar cells not in the infarct border zone.

In one aspect, a vector of the invention preferentially targets an ischemic region.

In one aspect, the ischemic region is an infarct border zone.

In one aspect, the treatment of the invention enhances wound healing.

In one embodiment, an AAV vector of the invention is administered to a subject with a cardiac injury, disease, or disorder. In one aspect, the injury, disease, or disorder is selected from the group consisting of myocardial infarction, reperfusion injury, heart failure, and peripheral artery disease.

In one embodiment, the invention provides a method of treating a cardiac injury, disease, or disorder by administering to a subject in need thereof a pharmaceutical composition comprising a pharmaceutically-acceptable carrier and an effective amount of a recombinant AAV vector of the invention. In one aspect, the pharmaceutical composition is administered systemically, intravenously, by intracoronary infusion, locally, or by direct injection into myocardium.

A treatment of the invention can be administered at varied times after an injury or diagnosis of a disease or disorder. For example, treatment can be administered at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, and 95 hours. A dose can also be applied more than once. Treatments can also be administered at later times to enhance various aspects of the wound healing process. In one aspect, the recombinant AAV vector of the invention is modified during each administration to recapitulate cardiac development. That is, the components can be modified based on the stage of the healing process in which the recombinant AAV vector is being administered.

In one embodiment, the compositions and methods of the invention are useful for transdifferentiating myofibroblasts into cardiomyocytes.

In one embodiment, the method induces differentiation of cardiac myofibroblasts into cardiac myocytes.

The present invention provides cardiac myofibroblasts transduced with a recombinant AAV vector of the invention.

The present invention further encompasses isolation and use of cardiac fibroblasts and cardiac myofibroblasts (or myofibroblast-like cells) in order to transduce them in vitro or to isolate cells that have already been transduced.

The present invention provides recombinant cardiac myocytes transdifferentiated from cardiac myofibroblasts transduced by a recombinant AAV of the invention.

SUMMARY OF SEQUENCES OF THE INVENTION

Sequence Names—
SEQ ID NO:1—Adeno-associated virus 9 (AAV9) nucleic acid sequence; GenBank Accession No. AX753250.1, 4385 bp
SEQ ID NO:2—AAV8 nucleic acid sequence; GenBank Accession No. NC_00626.1, 4393 bp
SEQ ID NO:3—pAPLuc-miR122×3, 6354 bp—it comprises the pAcTnTLuc-miR122×3 plasmid modified by cutting out cTnT promoter between XbaI and NcoI sites and inserting the Periostin promoter from pAPeGFP after cutting it out with XbaI and EcoRI and using a linker oligo to ligate the EcoRI site to the NcoI site, destroying the EcoRI site; Mouse Periostin Enhancer: 200-1098 (includes 804 bp enhancer); Periostin Minimal Promoter: 1105-1595 (includes 423 bp minimal promoter); PeriLinker used for periostin promoter insertion: 1602-1614; Luciferase from PGL3 enhancer Promega: 1617-3268; miR122 Sponge sites: 3307-3386; SV40 polyA: 3399-3639; AAV-2 ITR from psub201: 14-199, 3801-3968

SEQ ID NO:4—pAPeGFP, 5353 bp: Modified from pAcTNTeGFP by removal of cTNT promoter from XbaI/EcoRI sites and replacement with a modified periostin promoter based on the 1200 bp enhancer+minimal promoter from Lindsley et al. 2008; Periostin Enhancer: 200-1098 (includes 804 bp enhancer); Periostin Minimal Promoter: 1105-1595 (includes 423 bp minimal promoter); EGFP from peGFP-N1 (HindIII-Not1 786 bp fragment): 1646-2365; SV40 polyA: 2398-2638; AAV-2 ITR from psub201: 14-199, 2800-2967

SEQ ID NO:5—pAPiCre-miR122×3, 5740 bp: Modified from pAcTNTiCre by removal of cTNT promoter from XbaI/HindIII sites and replacement with a modified periostin promoter based on the 1200 bp enhancer+minimal promoter from Lindsley et al 2008; Periostin Enhancer: 200-1098 (includes 804 bp enhancer); Periostin Minimal Promoter: 1105-1595 (includes 423 bp minimal promoter); PeriLinker used for periostin promoter insertion: 1602-1614; iCre gene (including Kozak sequence): 1628-2683; iCre Linker sequence including translation termination codon: 2667-2686; miR122 Sponge Sites: 2693-2772; SV40 polyA: 2785-3025; AAV-2 ITR from psub201: 14-199, 3187-3354; Note that there is an additional XHOI site toward the end of the plasmid SEQ ID NO:6—1395 bp promoter/enhancer of SEQ ID NOs:3, 4, and 5 (position 200 to 1595 of each—comprising the 804 bp enhancer and the 243 bp minimal promoter)

SEQ ID NO:7—AAV6 nucleic acid sequence, 4683 bp; NCBI Accession Number AF028704.1

SEQ ID NO:8—5'-TCCGTGTTCTGCTGTGGAGTGATT-3' (forward) primer for amplifying periostin SEQ ID NO:9—5'-TAGGGATCTCTCTGCCTTCTGTCT-3' (reverse) primer for amplifying periostin Sequences—

```
(AAV9 nucleic acid sequence)-
                                                           SEQ ID NO: 1
cagagagggagtggccaactccatcactaggggtaatcgcgaagcgcctcccacgctgccgcgtcagcgctgacgtagatt acgtcataggggagtggtcctgtattagctgtcacgtgagtgcttttgcgacattttgcgacaccacatggccatttgaggtatat atggccgagtgagcgagcaggatctccattttgaccgcgaaatttgaacgagcagcagccatgccgggcttctacgagattgt gatcaaggtgccgagcgacctggacgagcacctgccgggcatttctgactcttttgtgaactgggtggccgagaaggaatgg gagctgccccggattctgacatggatcggaatctgatcgagcaggcacccctgaccgtggccgagaagctgcagcgcga cttcctggtccaatggccgccgcgtgagtaaggccccggaggccctcttctttgttcagttcgagaagggcgagagctactttca cctgcacgttctggtcgagaccacgggggtcaagtccatggtgctaggccgcttcctgagtcagattcgggagaagctggtc cagaccatctaccgcgggatcgagccgaccctgcccaactggttcgcggtgaccaagacgcgtaatggcgccggcgggg ggaacaaggtggtggacgagtgctacatccccaactacctcctgcccaagactcagcccgagctgcagtgggcgtggacta acatggaggagtatataagcgcgtgcttgaacctggccgagcgcaaacggctcgtggcgcagcacctgacccacgtcagcc agacgcaggagcagaacaaggagaatctgaaccccaattctgacgcgcccgtgatcaggtcaaaaacctccgcgcgctac atggagctggtcgggtggctggtggaccggggcatcacctccgagaagcagtggatccaggaggaccaggcctcgtacat
```

-continued

```
ctccttcaacgccgcctccaactcgcggtcccagatcaaggccgcgctggacaatgccggcaagatcatggcgctgaccaa atccgcgcccgactacctggtaggcccttcacttccggtggacattacgcagaaccgcatctaccgcatcctgcagctcaacg gctacgaccctgcctacgccggctccgtctttctcggctgggcacaaaagaagttcgggaaacgcaacaccatctggctgttt gggccggccaccacgggaaagaccaacatcgcagaagccattgcccacgccgtgcccttctacggctgcgtcaactggac caatgagaactttcccttcaacgattgcgtcgacaagatggtgatctggtgggaggagggcaagatgacggccaaggtcgtg gagtccgccaaggccattctcggcggcagcaaggtgcgcgtggaccaaaagtgcaagtcgtccgcccagatcgaccccac tcccgtgatcgtcacctccaacaccaacatgtgcgccgtgattgacgggaacagcaccaccttcgagcaccagcagcctctc caggaccggatgtttaagttcgaactcacccgccgtctggagcacgactttggcaaggtgacaaagcaggaagtcaaagagt tcttccgctgggccagtgatcacgtgaccgaggtggcgcatgagttttacgtcagaaagggcggagccagcaaaagacccg cccccgatgacgcggataaaagcgagcccaagcgggcctgcccctcagtcgcggatccatcgacgtcagacgcggaagg agctccggtggactttgccgacaggtaccaaaacaaatgttctcgtcacgcgggcatgcttcagatgctgcttccctgcaaaac gtgcgagagaatgaatcagaatttcaacatttgcttcacacacggggtcagagactgctcagagtgtttcccgcgtgtcaga atctcaaccggtcgtcagaaagaggacgtatcggaaactctgtgcgattcatcatctgctgggcgggctcccgagattgcttg ctcggcctgcgatctggtcaacgtggacctggatgactgtgtttctgagcaataaatgacttaaaccaggtatggctgccgatg gttatcttccagattggctcgaggacaacctctctgagggcattcgcgagtggtgggcgctgaaacctggagccccgaagcc caaagccaaccagcaaaagcaggacgacggccggggtctggtgcttcctggctacaagtacctcggacccttcaacggact cgacaaggggagcccgtcaacgcggcggacgcagcggccctcgagcacggcaaggcctacgaccagcagctgcagg cgggtgacaatccgtacctgcggtataaccacgccgacgccgagtttcaggagcgtctgcaagaagatacgtcttttgggg caacctcgggcgagcagtcttccaggccaagaagcgggttctcgaacctctcggtctggttgaggaaggcgctaagacggc tcctggaaagaagagaccggtagagccatcacccagcgttctccagactcctctacgggcatcggcaagaaaggccaaca gcccgccagaaaaagactcaattttggtcagactggcgactcagagtcagttccagacccctcaacctctcggagaacctccag cagcgccctctggtgtgggacctaatacaatggctgcaggcggtggcgcaccaatggcagacaataacgaaggcgccgac ggagtgggtaattcctcgggaaattggcattgcgattccacatggctgggggacagagtcatcaccaccagcacccgaacct gggcattgcccacctacaacaaccacctctacaagcaaatctccaatggaacatcgggaggaagcaccaacgacaacacct actttggctacagcacccccctgggggtattttgacttcaacagattccactgccacttctccaccacgtgactggcagcgactcat caacaacaactggggattccggccaaagagactcaacttcaagctgttcaacatccaggtcaaggaggttacgacgaacgaa ggcaccaagaccatcgccaataaccttaccagcaccgtccaggtctttacggactcggagtaccagctaccgtacgtcctagg ctctgcccaccaaggatgcctgccaccgtttcctgcagacgtcttcatggttcctcagtacggctacctgacgctcaacaatgg aagtcaagcgttaggacgttcttctttctactgtctggaatacttcccttctcagatgctgagaaccggcaacaactttcagttcag ctacactttcgaggacgtgcctttccacagcagctacgcacacagccagagtctagatcgactgatgaacccctcatcgacc agtacctatactacctggtcagaacacagacaactggaactgggggaactcaaactttggcattcagccaagcaggccctag ctcaatggccaatcaggctagaaactgggtacccgggccttgctaccgtcagcagcgcgtctccacaaccaccaaccaaaat aacaacagcaacttgcgtggacgggagctgctaaattcaagctgaacgggagagactcgctaatgaatcctggcgtggctat ggcatcgcacaaagacgacgaggaccgcttctttccatcaagtggcgttctcatatttggcaagcaaggagccgggaacgat ggagtcgactacagccaggtgctgattacagatgaggaagaaattaaagccaccaaccctgtagccacagaggaatacgga gcagtggccatcaacaaccaggccgctaacacgcaggcgcaaactggacttgtgcataaccagggagttattcctggtatgg tctggcagaaccgggacgtgtacctgcagggcccatttgggctaaaatacctcacacagatggcaacttcacccgtctcctc tgatgggtggatttggactgaaacacccacctccacagattctaattaaaaatacaccagtgccggcagatcctcctcttacctttc aatcaagccaagctgaactctttcatcacgcagtacagcacgggacaagtcagcgtggaaatcgagtgggagctgcagaaa gaaaacagcaagcgctggaatccagagatccagtatacttcaaactactacaaatctacaaatgtggactttgctgtcaatacca
```

-continued aaggtgtttactctgagcctcgcccattggtactcgttacctcacccgtaatttgtaattgcctgttaatcaataaaccggttaattc gtttcagttgaactttggtctctgcg (AAV8 nucleic acid sequence)-

SEQ ID NO: 2 cagagagggagtggccaactccatcactaggggtagcgcgaagcgcctcccacgctgccgcgtcagcgctgacgtaaatta cgtcatagggagtggtcctgtattagctgtcacgtgagtgcttttgcggcattttgcgacaccacgtggccatttgaggtatata tggccgagtgagcgagcaggatctccattttgaccgcgaaatttgaacgagcagcagccatgccgggcttctacgagatcgt gatcaaggtgccgagcgacctggacgagcacctgccgggcatttctgactcgtttgtgaactgggtggccgagaaggaatg ggagctgcccccggattctgacatggatcggaatctgatcgagcaggcacccctgaccgtggccgagaagctgcagcgcg acttcctggtccaatggcgccgcgtgagtaaggccccggaggccctcttctttgttcagttcgagaagggcgagagctactttc acctgcacgttctggtcgagaccacggggtcaagtccatggtgctaggccgcttcctgagtcagattcgggaaaagcttggt ccagaccatctacccgcggggtcgagccccaccttgcccaactggttcgcggtgaccaaagacgcggtaatggcgccggc gggggggaacaaggtggtggacgagtgctacatccccaactacctcctgcccaagactcagcccgagctgcagtgggcgt ggactaacatggaggagtatataagcgcgtgcttgaacctggccgagcgcaaacggctcgtggcgcagcacctgacccac gtcagccagacgcaggagcagaacaaggagaatctgaaccccaattctgacgcgcccgtgatcaggtcaaaaacctccgc gcgctatatggagctggtcgggtggctggtggaccggggcatcacctccgagaagcagtggatccaggaggaccaggcct cgtacatctccttcaacgccgcctccaactcgcggtcccagatcaaggccgcgctggacaatgccggcaagatcatggcgct gaccaaatccgcgcccgactacctggtggggcctcgctgcccgcggacattacccagaaccgcatctaccgcatcctcgc tctcaacggctacgaccctgcctacgccggctccgtctttctcggctgggctcagaaaaagttcgggaaacgcaacaccatct ggctgtttggaccgccaccaccggcaagaccaacattgcggaagccatcgcccacgccgtgcccttctacggctgcgtca actggaccaatgagaactttccccttcaatgattgcgtcgacaagatggtgatctggtgggaggagggcaagatgacggccaa ggtcgtggagtccgccaaggccattctcggcggcagcaaggtgcgcgtgaccaaaagtgcaagtcgtccgcccagatcg accccacccccgtgatcgtcacctccaacaccaacatgtgcgccgtgattgacgggaacagcaccaccttcgagcaccagc agcctctccaggaccggatgtttaagttcgaactcacccgccgtctggagcacgactttggcaaggtgacaaagcaggaagt caaagagttcttccgctgggccagtgatcacgtgaccgaggtggcgcatgagttttacgtcagaaagggcggagccagcaa aagacccgcccccgatgacgcggataaaaagcgagcccaagcgggcctgcccctcagtcgcggatccatcgacgtcagac gcggaaggagctccggtggactttgccgacaggtaccaaaacaaatgttctcgtcacgcgggcatgcttcagatgctgtttcc ctgcaaaacgtgcgagagaatgaatcagaatttcaacatttgcttcacacacgggtcagagactgctcagagtgtttccccgg cgtgtcagaatctcaaccggtcgtcagaaagaggacgtatcggaaactctgtgcgattcatcatctgctgggcgggctcccg agattgcttgctcggcctgcgatctggtcaacgtggacctggatgactgtgtttctgagcaataaatgacttaaaccaggtatgg ctgccgatggttatcttccagattggctcgaggacaacctctctgagggcattcgcgagtggtgggcgctgaaacctggagcc ccgaagcccaaagccaaccagcaaaagcaggacgacggccggggtctggtgcttcctggctacaagtacctcggacccttc aacggactcgacaaggggagcccgtcaacgcggcggacgcagcggccctcgagcacgacaaggcctacgaccagca gctgcaggcgggtgacaatccgtacctgcggtataaccacgccgacgccgagtttcaggagcgtctgcaagaagatacgtct tttgggggcaacctcggcgagcagtcttccaggccaagaagcgggttctcgaacctctcggtctggttgaggaaggcgcta agacggctcctggaaagaagagaccggtagagccatcaccccagcgttctccagactcctctacgggcatcggcaagaaag gccaacagcccgccagaaaagactcaattttggtcagactggcgactcagagtcagttccagaccctcaacctctcggaga acctccagcagcgccctctggtgtgggacctaatacaatggctgcaggcggtggcgcaccaatggcagacaataacgaagg cgccgacggagtgggtagttcctcgggaaattggcattgcgattccacatggctgggcgacagagtcatcaccaccagcacc cgaacctgggccctgcccacctacaacaaccacctctacaagcaaatctccaacgggacatcgggaggagccaccaacga caacacctacttcggctacagcaccccctgggggtattttgactttaacagattccactgccacttttcaccacgtgactggcag cgactcatcaacaacaactggggattccggcccaagagactcagcttcaagctcttcaacatccaggtcaaggaggtcacgc -continued agaatgaaggcaccaagaccatcgccaataacctcaccagcaccatccaggtgtttacggactcggagtaccagctgccgta cgttctcggctctgcccaccagggctgcctgcctccgttcccggcggacgtgttcatgattccccagtacggctacctaacact caacaacggtagtcaggccgtgggacgctcctccttctactgcctggaatactttccttcgcagatgctgagaaccggcaaca acttccagtttacttacaccttcgaggacgtgcctttccacagcagctacgcccacagccagagcttggaccggctgatgaatc ctctgattgaccagtacctgtactacttgtctcggactcaaacaacaggaggcacggcaaatacgcagactctgggcttcagcc aaggtgggcctaatacaatggccaatcaggcaaagaactggctgccaggaccctgttaccgccaacaacgcgtctcaacga caaccgggcaaaacaacaatagcaactttgcctggactgctgggaccaaataccatctgaatggaagaaattcattggctaat cctggcatcgctatggcaacacacaaagacgacgaggagcgttttttcccagtaacgggatcctgattttggcaaacaaaat gctgccagagacaatgcggattacagcgatgtcatgctcaccagcgaggaagaaatcaaaaccactaaccctgtggctacag aggaatacggtatcgtggcagataacttgcagcagcaaaacacggctcctcaaattggaactgtcaacagccaggggcctt acccggtatggtctggcagaaccgggacgtgtacctgcagggtcccatctgggccaagattcctcacacggacggcaacttc cacccgtctccgctgatgggcggctttggcctgaaacatcctccgcctcagatcctgatcaagaacacgcctgtacctgcgga tcctccgaccaccttcaaccagtcaaagctgaactctttcatcacgcaatacagcaccggacaggtcagcgtggaaattgaatg ggagctgcagaaggaaaacagcaagcgctggaaccccgagatccagtacacctccaactactacaaatctacaagtgtgg actttgctgttaatacagaaggcgtgtactctgaaccccgcccattggcacccgttacctcacccgtaatctgtaattgcctgtta atcaataaaccggttgattcgtttcagttgaactttggtctctgcg (pAPLuc-miR122x3)-

SEQ ID NO: 3 gaactcgatcgagcagctgcgcgctcgctcgctcactgaggccgcccgggcaaagcccgggcgtcgggcgacctttggtc gcccggcctcagtgagcgagcgagcgcgcagagagggagtggccaactccatcactaggggttccttgtagttaatgattaa cccgccatgctacttatctacgtagccatgctctagagacctctgtaggctggctggtgatactcaattttatttcatgtatacacaa cattttaaagatggaaattagtacatgattcttgatttaaattcttcaagctaacaatctttttttttttttttaaagtggcctcagtcaaag acactaaagatcaccgagtcttgcatagagttttccatttacaggactagagaaagctagtggagacacagatcgggtgcggag gtagtgagaagcacttttcctaagaaggtgcagggttgactccaaggcttggctgggttataagagttacatgtattatttattctat atgtaagcaacttttgagctcatgtgccatggcaacctatggaccgcatgttaatatagaagcattttaaaattagtgatacaatc aagaccaagggcatcctgcttatggtttgtgtgcacaggcttacagagtgcagagtccgcgaggagtcccagggactgctgg agtttgaggttggtttcacagtggtgagtaagcgtggcagtgtaatgacctcatggtctcccgaggccagataacagagaactg cctataaatcagcatgccgcggctagagagaaacggccctgtttctcagacacactatctctcttcagctacataatgaaccattt ctttctcagtaatgacttacatctctgggtcagactttgcagccctggaaagtcggacttcattttcatgatttccgtcatcttcccga ctggtaggaaaattgcaggggtcagtagtgtcagcatagtttcacagagctgaagagaaagggccctgtgtggagagcgact tttgatgagagccccggaagagagtgtgcccttccggggatttttttcccagtctcttctacaacttcagctagccaattgagggg catgtgtctcttccacataagctgtggaaatcacactttaaatgcattgtacatctatccaggatttgggttaaatgcccctgtgattt ctcttctccgtgttctgctgtggagtgatttaagtgcaatcagatcaaaccaggaaagtaactgagctcagagacacagagtgtg gtggcagagacagaaggcagagagatccctaaactcagaatcagctcttttcgcaatgtaaacctatagaagtgaaaaacgg gctcaccatgattgaaaacaaataggagacagagttcagattgctcagaacccaggagatttccagggacagcccagggctg ctggtgcttctgtaaggccatcgcaagcttcaggttgggccagcgccccctcccacagccttgctccctcccacagcccagag ctatataaactcagctctccagagcacaggccagatctcttcctggacggagctcagggctgaaggaattggatggggaccg aaccatggaagacgccaaaaacataaagaaaggcccggcgccattctatccgctggaagatggaaccgctggagagcaac tgcataaggctatgaagagatacgccctggttcctggaacaattgcttttacagatgcacatatcgaggtggacatcacttacgc tgagtacttcgaaatgtccgttcggttggcagaagctatgaaacgatatgggctgaatacaaatcacagaatcgtcgtatgcagt gaaaactctcttcaattctttatgccggtgttgggcgcgttatttatcggagttgcagttgcgcccgcgaacgacatttataatgaa -continued cgtgaattgctcaacagtatgggcatttcgcagcctaccgtggtgttcgtttccaaaaaggggttgcaaaaaattttgaacgtgc aaaaaaagctcccaatcatccaaaaaattattatcatggattctaaaacggattaccagggatttcagtcgatgtacacgttcgtc acatctcatctacctcccggttttaatgaatacgattttgtgccagagtccttcgatagggacaagacaattgcactgatcatgaac tcctctggatctactggtctgcctaaaggtgtcgctctgcctcatagaactgcctgcgtgagattctcgcatgccagagatcctat ttttggcaatcaaatcattccggatactgcgattttaagtgttgttccattccatcacggttttggaatgtttactacactcggatattg atatgtggatttcgagtcgtcttaatgtatagatttgaagaagagctgtttctgaggagccttcaggattacaagattcaaagtgcg ctgctggtgccaaccctattctccttcttcgccaaaagcactctgattgacaaatacgatttatctaatttacacgaaattgcttctg gtggcgctcccctctctaaggaagtcggggaagcggttgccaagaggttccatctgccaggtatcaggcaaggatatgggct cactgagactacatcagctattctgattacacccgaggggatgataaaccgggcgcggtcggtaaagttgttccattttttgaa gcgaaggttgtggatctggataccggaaaacgctgggcgttaatcaaagaggcgaactgtgtgtgagaggtcctatgattat gtccggttatgtaaacaatccggaagcgaccaacgccttgattgacaaggatggatggctacattctggagacatagcttactg ggacgaagacgaacacttcttcatcgttgaccgcctgaagtctctgattaagtacaaaggctatcaggtggctcccgctgaatt ggaatccatcttgctccaacaccccaacatcttcgacgcaggtgtcgcaggtcttcccgacgatgacgccggtgaacttcccg ccgccgttgttgttttggagcacggaaagacgatgacggaaaaagagatcgtggattacgtcgccagtcaagtaacaaccgc gaaaaagttgcgcggaggagttgtgtttgtggacgaagtaccgaaaggtcttaccggaaaactcgacgcaagaaaaatcaga gagatcctcataaaggccaagaagggcggaaagatcgccgtgtaattctagcggccgctcgaggccggcaaggccggatc cacaaacaccattgtcacactccagtatacacaaacaccattgtcacactccagatatcacaaacaccattgtcacactccaga attcggatccagacatgataagatacattgatgagtttggacaaaccacaactagaatgcagtgaaaaaatgctttatttgtgaa atttgtgatgctattgctttatttgtaaccattataagctgcaataaacaagttaacaacaacaattgcattcattttatgtttcaggttc aggggggaggtgtgggaggttttttaaagcaagtaaaacctctacaaatgtggtatggctgattatgatccggctgcctcgcgcg tttcggtgatgacggtgaaaacctctgacacatgcagctcccggagacggtcacagcttgtctgtaagcggatgccgggagc agacaagcccgtcagggcgcgtcagcgggtgttggcgggtgtcggggcgcagccatgaggtcgaccgtagataagtagca tggcgggttaatcattaactacaaggaaccccctagtgatggagttggccactccctctctgcgcgctcgctcgctcactgaggc cgggcgaccaaaggtcgcccgacgcccgggctttgcccgggcggcctcagtgagcgagcgagcgcgccagctgaagct atcagatctgccggtctccctatagtgagtcgtattaatttcgataagccaggttaacctgcattaatgaatcggccaacgcgcg gggagaggcggtttgcgtattgggcgctcttccgcttcctcgctcactgactcgctgcgctcggtcgttcggctgcggcgag cggtatcagctcactcaaaggcggtaatacggttatccacagaatcaggggataacgcaggaaagaacatgtgagcaaaag gccagcaaaaggccaggaaccgtaaaaaggccgcgttgctggcgtttttccataggctccgcccccctgacgagcatcaca aaaatcgacgctcaagtcagaggtggcgaaacccgacaggactataaagataccaggcgtttccccctggaagctccc tcgtgcgctctcctgttccgaccctgccgcttaccggatacctgtccgcctttctcccttcgggaagcgtggcgctttctcatagc tcacgctgtaggtatctcagttcggtgtaggtcgttcgctccaagctgggctgtgtgcacgaaccccccgttcagcccgaccgc tgcgccttatccggtaactatcgtcttgagtccaacccggtaagacacgacttatcgccactggcagcagccactggtaacag gattagcagagcgaggtatgtaggcggtgctacagagttcttgaagtggtggcctaactacggctacactagaagaacagtat ttggtatctgcgctctgctgaagccagttaccttcggaaaaagagttggtagctcttgatccggcaaacaaaccaccgctggta gcggtggtttttttgtttgcaagcagcagattacgcgcagaaaaaaaggatctcaagaagatcctttgatcttttctacggggtct gacgctcagtggaacgaaaactcacgttaagggattttggtcatgagattatcaaaaaggatcttcacctagatccttttaaatta aaaatgaagttttaaatcaatctaaagtatatatgagtaaacttggtctgacagttaccaatgcttaatcagtgaggcacctatctca gcgatctgtctatttcgttcatccatagttgcctgactccccgtcgtgtagataactacgatacgggagggcttaccatctggccc cagtgctgcaatgataccgcgagacccacgctcaccggctccagatttatcagcaataaaccagccagccggaagggccga gcgcagaagtggtcctgcaactttatccgcctccatccagtctattaattgttgccgggaagctagagtaagtagttcgccagtta atagtttgcgcaacgttgttgccattgctacaggcatcgtggtgtcacgctcgtcgtttggtatggcttcattcagctccggttccc -continued aacgatcaaggcgagttacatgatcccccatgttgtgcaaaaaagcggttagctccttcggtcctccgatcgttgtcagaagtaa
gttggccgcagtgttatcactcatggttatggcagcactgcataattctcttactgtcatgccatccgtaagatgcttttctgtgact
ggtgagtactcaaccaagtcattctgagaatagtgtatgcggcgaccgagttgctcttgcccggcgtcaatacgggataatacc
gcgccacatagcagaactttaaaagtgctcatcattggaaaacgttcttcggggcgaaaactctcaaggatcttaccgctgttga
gatccagttcgatgtaacccactcgtgcacccaactgatcttcagcatcttttactttcaccagcgtttctgggtgagcaaaaaca
ggaaggcaaaatgccgcaaaaaagggaataagggcgacacggaaatgttgaatactcatactcttccttttcaatattattgaa
gcatttatcagggttattgtctcatgagcggatacatatttgaatgtatttagaaaaataaacaaataggggttccgcgcacatttc
cccgaaaagtgccacctgacgtctaagaaaccattattatcatgacattaacctataaaaataggcgtatcacgaggccctttcg
tctcgcgcgtttcggtgatgacggtgaaaacctctgacacatgcagctcccggagacggtcacagcttgtctgtaagcggatg
ccgggagcagacaagcccgtcagggcgcgtcagcgggtgttggcgggtgtcggggctggcttaactatgcggcatcagag
cagattgtactgagagtgcaccatatggacatattgtcgttagaacgcggctacaattaatacataaccttatgtatcatacacata
cgatttaggtgacactata (pAPeGFP)-

SEQ ID NO: 4 gaactcgatcgagcagctgcgcgctcgctcgctcactgaggccgcccgggcaaagcccgggcgtcgggcgacctttggtc
gcccggcctcagtgagcgagcgagcgcgcagagagggagtggccaactccatcactagggttccttgtagttaatgattaa
cccgccatgctacttatctacgtagccatgctctagagacctctgtaggctggctggtgatactcaatttattcatgtatacaca
cattttaaagatggaaattagtacatgattcttgatttaaattctttcaagctaacaatcttttttttttttaaagtggcctcagtcaaag
acactaaagatcaccgagtcttgcatagagtttccatttacaggactagagaaagctagtggagacacagatcgggtgcggag
gtagtgagaagcacttttcctaagaaggtgcagggttgactccaaggcttggctgggttataagagttacatgtattatttattctat
atgtaagcaacttttgagctcatgtgccatggcaacctatggaccgcatgttaatatagaagcattttaaaattagtgatacaatc
aagaccaagggcatcctgcttatggtttgtgtgcacaggcttacagagtgcagagtccgcgaggagtcccagggactgctgg
agtttgaggttggtttcacagtggtgagtaagcgtggcagtgtaatgacctcatggtctcccgaggccagataacagagaactg
cctataaatcagcatgccgcggctagagagaaacggccctgtttctcagacacactatctctcttcagctacataatgaaccattt
ctttctcagtaatgacttacatctctgggtcagactttgcagccctggaaagtcggacttcattttcatgatttccgtcatcttcccga
ctggtaggaaaattgcaggggtcagtagtgtcagcatagtttcacagagctgaagagaaagggccctgtgtggagagcg
acttttgatgagagccccggaagagagtgtgcccttccggggattttttcccagtctcttctacaacttcagctagccaattgag
gggcatgtgtctcttccacataagctgtggaaatcacactttaaatgcattgtacatctatccaggatttgggttaaatgccctgt
gatttctcttctccgtgttctgctgtggagtgatttaagtgcaatcagatcaaaccaggaaagtaactgagctcagagacacaga
gtgtggtggcagagacagaaggcagagagatccctaaactcagaatcagctcttttcgcaatgtaaacctatagaagtgaaaa
acgggctcaccatgattgaaaacaaataggagacagagttcagattgctcagaacccaggagatttccagggacagcccag
ggctgctggtgcttctgtaaggccatcgcaagcttcaggttggcccagcgccccctcccacagccttgctccctcccacagcc
cagagctatataaactcagctctccagagcacaggccagatctcttcctggacggagctcagggctgaaggaattctgcagtc
gacggtaccgcgggcccgggatccaccggtcgccaccatggtgagcaagggcgaggagctgttcaccggggtggtgccc
atcctggtcgagctggacggcgacgtaaacggccacaagttcagcgtgtccggcgagggcgagggcgatgccacctacgg
caagctgaccctgaagttcatctgcaccaccggcaagctgcccgtgccctggcccaccctcgtgaccaccctgacctacggc
gtgcagtgcttcagccgctaccccgaccacatgaagcagcacgacttcttcaagtccgccatgcccgaaggctacgtccagg
agcgcaccatcttcttcaaggacgacggcaactacaagacccgcgccgaggtgaagttcgagggcgacaccctggtgaac
cgcatcgagctgaagggcatcgacttcaaggaggacggcaacatcctggggcacaagctggagtacaactacaacagcca
caacgtctatatcatggccgacaagcagaagaacggcatcaaggtgaacttcaagatccgccacaacatcgaggacggcag
cgtgcagctcgccgaccactaccagcagaacacccccatcggcgacggccccgtgctgctgcccgacaaccactacctga -continued

```
gcacccagtccgccctgagcaaagaccccaacgagaagcgcgatcacatggtcctgctggagttcgtgaccgccgccggg atcactctcggcatggacgagctgtacaagtaaagcggccgctcgaggccggcaaggccggatccagacatgataagatac attgatgagtttggacaaaccacaactagaatgcagtgaaaaaaatgctttatttgtgaaatttgtgatgctattgctttatttgtaac cattataagctgcaataaacaagttaacaacaacaattgcattcattttatgtttcaggttcaggggggaggtgtgggaggttttttaa agcaagtaaaacctctacaaatgtggtatggctgattatgatccggctgcctcgcgcgtttcggtgatgacggtgaaaacctctg acacatgcagctcccggagacggtcacagcttgtctgtaagcggatgccgggagcagacaagcccgtcagggcgcgtcag cgggtgttggcgggtgtcggggcgcagccatgaggtcgaccgtagataagtagcatggcgggttaatcattaactacaagga acccctagtgatggagttggccactccctctctgcgcgctcgctcgctcactgaggccgggcgaccaaaggtcgcccgacg cccgggctttgcccgggcggcctcagtgagcgagcgagcgcgccagctgaagctatcagatctgccggtctccctatagtg agtcgtattaatttcgataagccaggttaacctgcattaatgaatcggccaacgcgcggggagaggcggtttgcgtattgggcg ctcttccgcttcctcgctcactgactcgctgcgctcggtcgttcggctgcggcgagcggtatcagctcactcaaaggcggtaat acggttatccacagaatcaggggataacgcaggaaagaacatgtgagcaaaaggccagcaaaaggccaggaaccgtaaa aaggccgcgttgctggcgtttttccataggctccgcccccctgacgagcatcacaaaaatcgacgctcaagtcagaggtggc gaaacccgacaggactataaagataccaggcgtttccccctggaagctccctcgtgcgctctcctgttccgaccctgccgctta ccggatacctgtccgcctttctcccttcgggaagcgtggcgctttctcatagctcacgctgtaggtatctcagttcggtgtaggtc gttcgctccaagctgggctgtgtgcacgaaccccccgttcagcccgaccgctgcgccttatccggtaactatcgtcttgagtcc aacccggtaagacacgacttatcgccactggcagcagccactggtaacaggattagcagagcgaggtatgtaggcggtgct acagagttcttgaagtggtggcctaactacggctacactagaagaacagtatttggtatctgcgctctgctgaagccagttacctt cggaaaaagagttggtagctcttgatccggcaaacaaaccaccgctggtagcggtggtttttttgtttgcaagcagcagattac gcgcagaaaaaaaggatctcaagaagatcctttgatcttttctacggggtctgacgctcagtggaacgaaaactcacgttaagg gattttggtcatgagattatcaaaaaggatcttcacctagatccttttaaattaaaaatgaagttttaaatcaatctaaagtatatatga gtaaacttggtctgacagttaccaatgcttaatcagtgaggcacctatctcagcgatctgtctatttcgttcatccatagttgcctga ctccccgtcgtgtagataactacgatacgggagggcttaccatctggccccagtgctgcaatgataccgcgagacccacgctc accggctccagatttatcagcaataaaccagccagccggaagggccgagcgcagaagtggtcctgcaactttatccgcctcc atccagtctattaattgttgccgggaagctagagtaagtagttcgccagttaatagtttgcgcaacgttgttgccattgctacaggc atcgtggtgtcacgctcgtcgtttggtatggcttcattcagctccggttcccaacgatcaaggcgagttacatgatcccccatgtt gtgcaaaaaagcggttagctccttcggtcctccgatcgttgtcagaagtaagttggccgcagtgttatcactcatggttatggca gcactgcataattctcttactgtcatgccatccgtaagatgcttttctgtgactggtgagtactcaaccaagtcattctgagaatagt gtatgcggcgaccgagttgctcttgcccggcgtcaatacgggataataccgcgccacatagcagaactttaaaagtgctcatc attggaaaacgttcttcggggcgaaaactctcaaggatcttaccgctgttgagatccagttcgatgtaacccactcgtgcaccca actgatcttcagcatcttttactttcaccagcgtttctgggtgagcaaaaacaggaaggcaaaatgccgcaaaaaagggaataa gggcgacacggaaatgttgaatactcatactcttcctttttcaatattattgaagcatttatcagggttattgtctcatgagcggatac atatttgaatgtatttagaaaaataaacaaataggggttccgcgcacatttccccgaaaagtgccacctgacgtctaagaaacca ttattatcatgacattaacctataaaaataggcgtatcacgaggccctttcgtctcgcgcgtttcggtgatgacggtgaaaacctct gacacatgcagctcccggagacggtcacagcttgtctgtaagcggatgccgggagcagacaagcccgtcagggcgcgtca gcgggtgttggcgggtgtcggggctggcttaactatgcggcatcagagcagattgtactgagagtgcaccatatggacatatt gtcgttagaacgcggctacaattaatacataaccttatgtatcatacacatacgatttaggtgacactata (pAPiCre-miR122x3)-
```

SEQ ID NO: 5

```
gaactcgatcgagcagctgcgcgctcgctcgctcactgaggccgcccgggcaaagcccgggcgtcgggcgacctttggtc gcccggcctcagtgagcgagcgagcgcgcagagagggagtggccaactccatcactaggggtccttgtagttaatgattaa cccgccatgctacttatctacgtagccatgctctagagacctctgtaggctggctggtgatactcaatttttatttcatgtatacacaa
```

-continued

```
cattttaaagatggaaattagtacatgattcttgatttaaattctttcaagctaacaatctttttttttttttaaagtggcctcagtcaaag acactaaagatcaccgagtcttgcatagagtttccatttacaggactagagaaagctagtggagacacagatcgggtgcggag gtagtgagaagcacttttcctaagaaggtgcagggttgactccaaggcttggctgggttataagagttacatgtattatttattctat atgtaagcaacttttgagctcatgtgccatggcaacctatggaccgcatgttaatatagaagcattttaaaattagtgatacaatca agaccaagggcatcctgcttatggtttgtgtgcacaggcttacagagtgcagagtccgcgaggagtcccagggactgctgga gtttgaggttggtttcacagtggtgagtaagcgtggcagtgtaatgacctcatggtctcccgaggccagataacagagaactgc ctataaatcagcatgccgcggctagagagaaacggccctgtttctcagacacactatctctcttcagctacataatgaaccatttc tttctcagtaatgacttacatctctgggtcagactttgcagccctggaaagtcggacttcattttcatgatttccgtcatcttcccgac tggtaggaaaattgcaggggtcagtagtgtcagcatagtttcacagagctgaagagaaagggccctgtgtggagagcgacttt tgatgagagccccggaagagagtgtgcccttccggggatttttttcccagtctcttctacaacttcagctagccaattgaggggc atgtgtctcttccacataagctgtggaaatcacactttaaatgcattgtacatctatccaggatttgggttaaatgccctgtgatttc tcttctccgtgttctgctgtggagtgatttaagtgcaatcagatcaaaccaggaaagtaactgagctcagagacacagagtgtgg tggcagagacagaaggcagagagatccctaaaactcagaatcagctcttttcgcaatgtaaacctatagaagtgaaaaacggg ctcaccatgattgaaaacaaataggagacagagttcagattgctcagaacccaggagatttccagggacagcccagggctgc tggtgcttctgtaaggccatcgcaagcttcaggttggcccagcgcccctcccacagccttgctccctcccacagcccagagc tatataaactcagctctccagagcacaggccagatctcttcctggacggagctcagggctgaaggaattcgatggggaccga aaagcttgtccaccatggtgcccaagaagaagaggaaagtctccaacctgctgactgtgcaccaaaacctgcctgccctccct gtggatgccacctctgatgaagtcaggaagaacctgatggacatgttcagggacaggcaggccttctctgaacacacctgga agatgctcctgtctgtgtgcagatcctgggctgcctggtgcaagctgaacaacaggaaatggttccctgctgaacctgaggat gtgagggactacctcctgtacctgcaagccagaggcctggctgtgaagaccatccaacagcacctgggccagctcaacatg ctgcacaggagatctggcctgcctcgcccttctgactccaatgctgtgtccctggtgatgaggagaatcagaaaggagaatgt ggatgctggggagagagccaagcaggccctggccttttgaacgcactgactttgaccaagtcagatccctgatggagaactct gacagatgccaggacatcaggaacctggccttcctgggcattgcctacaacaccctgctgcgcattgccgaaattgccagaat cagagtgaaggacatctcccgcaccgatggtgggagaatgctgatccacattggcaggaccaagaccctggtgtccacagc tggtgtggagaaggccctgtccctgggggttaccaagctggtggagagatggatctctgtgtctggtgtggctgatgaccccca acaactacctgttctgccgggtcagaaagaatggtgtggctgccccttctgccacctcccaactgtccacccgggccctggaa gggatctttgaggccacccaccgcctgatctatggtgccaaggatgactctgggcagagatacctggcctggtctggccactc tgccagagtgggtgctgccagggacatggccagggctggtgtgtccatccctgaaatcatgcaggctggtggctggaccaat gtgaacattgtgatgaactacatcagaaacctggactctgagactggggccatggtgaggctgctcgaggatggggactgaa aggatccacaaacaccattgtcacactccagtatacacaaacaccattgtcacactccagatatcacaaacaccattgtcacact ccagaattcggatccagacatgataagatacattgatgagtttggacaaaccacaactagaatgcagtgaaaaaaatgctttatt tgtgaaatttgtgatgctattgctttatttgtaaccattataagctgcaataaacaagttaacaacaacaattgcattcattttatgtttc aggttcaggggaggtgtgggaggttttttaaagcaagtaaaacctctacaaatgtggtatggctgattatgatccggctgcctc gcgcgtttcggtgatgacggtgaaaacctctgacacatgcagctcccggagacggtcacagcttgtctgtaagcggatgccg ggagcagacaagcccgtcagggcgcgtcagcgggtgttggcgggtgtcggggcgcagccatgagctcgaccgtagataa gtagcatggcgggttaatcattaactacaaggaacccctagtgatggagttggccactccctctctgcgcgctcgctcgctcac tgaggccgggcgaccaaaggtcgcccgacgcccgggctttgcccgggcggcctcagtgagcgagcgagcgcgccagct gaagctatcagatctgccggtctccctatagtgagtcgtattaatttcgataagccaggttaacctgcattaatgaatcggccaac gcgcggggagaggcggtttgcgtattgggcgctcttccgcttcctcgctcactgactcgctgcgctcggtcgttcggctgcgg cgagcggtatcagctcactcaaaggcggtaatacggttatccacagaatcaggggataacgcaggaaagaacatgtgagca
```

-continued

```
aaaggccagcaaaaggccaggaaccgtaaaaaggccgcgttgctggcgttttttccataggctccgccccctgacgagcat cacaaaaatcgacgctcaagtcagaggtggcgaaacccgacaggactataaagataccaggcgtttccccctggaagctcc ctcgtgcgctctcctgttccgaccctgccgcttaccggatacctgtccgcctttctcccttcgggaagcgtggcgctttctcatag ctcacgctgtaggtatctcagttcggtgtaggtcgttcgctccaagctgggctgtgtgcacgaaccccccgttcagcccgaccg ctgcgccttatccggtaactatcgtcttgagtccaacccggtaagacacgacttatcgccactggcagcagccactggtaacag gattagcagagcgaggtatgtaggcggtgctacagagttcttgaagtggtggcctaactacggctacactagaagaacagtat ttggtatctgcgctctgctgaagccagttaccttcggaaaaagagttggtagctcttgatccggcaaacaaaccaccgctggta gcggtggtttttttgtttgcaagcagcagattacgcgcagaaaaaaaggatctcaagaagatcctttgatcttttctacggggtct gacgctcagtggaacgaaaactcacgttaagggattttggtcatgagattatcaaaaaggatcttcacctagatccttttaaatta aaaatgaagttttaaatcaatctaaagtatatatgagtaaacttggtctgacagttaccaatgcttaatcagtgaggcacctatctca gcgatctgtctatttcgttcatccatagttgcctgactccccgtcgtgtagataactacgatacgggagggcttaccatctggccc cagtgctgcaatgataccgcgagacccacgctcaccggctccagatttatcagcaataaaccagccagccggaagggccga gcgcagaagtggtcctgcaactttatccgcctccatccagtctattaattgttgccgggaagctagagtaagtagttcgccagtta atagtttgcgcaacgttgttgccattgctacaggcatcgtggtgtcacgctcgtcgtttggtatggcttcattcagctccggttccc aacgatcaaggcgagttacatgatcccccatgttgtgcaaaaaagcggttagctccttcggtcctccgatcgttgtcagaagtaa gttggccgcagtgttatcactcatggttatggcagcactgcataattctcttactgtcatgccatccgtaagatgcttttctgtgact ggtgagtactcaaccaagtcattctgagaatagtgtatgcggcgaccgagttgctcttgcccggcgtcaatacgggataatacc gcgccacatagcagaactttaaaagtgctcatcattggaaaacgttcttcggggcgaaaactctcaaggatcttaccgctgttga gatccagttcgatgtaacccactcgtgcacccaactgatcttcagcatcttttactttcaccagcgtttctgggtgagcaaaaaca ggaaggcaaaatgccgcaaaaaagggaataagggcgacacggaaatgttgaatactcatactcttcctttttcaatattattgaa gcatttatcagggttattgtctcatgagcggatacatatttgaatgtatttagaaaaataaacaaataggggttccgcgcacatttc cccgaaaagtgccacctgacgtctaagaaaccattattatcatgacattaacctataaaaataggcgtatcacgaggccctttcg tctcgcgcgtttcggtgatgacggtgaaaacctctgacacatgcagctcccggagacggtcacagcttgtctgtaagcggatg ccgggagcagacaagcccgtcagggcgcgtcagcgggtgttggcgggtgtcggggctggcttaactatgcggcatcagag cagattgtactgagagtgcaccatatggacatattgtcgttagaacgcggctacaattaatacataaccttatgtatcatacacata cgatttaggtgacactata
```

(1395 bp promoter/enhancer of SEQ ID NOs: 3, 4, and 5)-

SEQ ID NO: 6

```
gacctctgtaggctggctggtgatactcaattttatttcatgtatacacaacattttaaagatggaaattagtacatgattcttgattta aattctttcaagctaacaatctttttttttttttttaaagtggcctcagtcaaagacactaaagatcaccgagtcttgcatagagtttcca tttacaggactagagaaagctagtggagacacagatcgggtgcggaggtagtgagaagcacttttcctaagaaggtgcaggg ttgactccaaggcttggctgggttataagagttacatgtattatttattctatatgtaagcaacttttgagctcatgtgccatggcaac ctatggaccgcatgttaatatagaagcattttaaaattagtgatacaatcaagaccaagggcatcctgcttatggtttgtgtgcaca ggcttacagagtgcagagtccgcgaggagtcccagggactgctggagtttgaggttggtttcacagtggtgagtaagcgtgg cagtgtaatgacctcatggtctcccgaggccagataacagagaactgcctataaatcagcatgccgcggctagagagaaacg gccctgtttctcagacacactatctctcttcagctacataatgaaccatttctttctcagtaatgacttacatctctgggtcagactttg cagccctggaaagtcggacttcattttcatgatttccgtcatcttcccgactggtaggaaaattgcagggggtcagtagtgtcagc atagtttcacagagctgaagagaaagggccctgtgtggagagcgacttttgatgagagccccggaagagagtgtgcccttcc ggggattttttttcccagtctcttctacaacttcagctagccaattgagggggcatgtgtctcttccacataagctgtggaaatcacac tttaaatgcattgtacatctatccaggatttgggttaaatgcccctgtgatttctcttctccgtgttctgctgtggagtgatttaagtgc aatcagatcaaaccaggaaagtaactgagctcagagacacagagtgtggtggcagagacagaaggcagagagatccctaa actcagaatcagctcttttcgcaatgtaaacctatagaagtgaaaaacgggctcaccatgattgaaaacaaataggagacaga
```

-continued gttcagattgctcagaacccaggagatttccagggacagcccagggctgctggtgcttctgtaaggccatcgcaagcttcagg ttggcccagcgccccctcccacagccttgctccctcccacagcccagagctatataaactcagctctccagagcacaggcca gatctcttcctggacggagctcagggctgaa (AAV6 nucleic acid sequence)-

SEQ ID NO: 7 ttggccactccctctctgcgcgctcgctcgctcactgaggccgggcgaccaaaggtcgcccgacgcccgggctttgcccgg gcggcctcagtgagcgagcgagcgcgcagagagggagtggccaactccatcactaggggttcctggagggtggagtcg tgacgtgaattacgtcatagggttagggaggtcctgtattagaggtcacgtgagtgttttgcgacattttgcgacaccatgtggtc acgctgggtatttaagcccgagtgagcacgcagggtctccatttgaagcgggaggtttgaacgcgcagcgccatgccggg gttttacgagattgtgattaaggtccccagcgaccttgacgagcatctgccccggcatttctgacagctttgtgaactgggtggcc gagaaggaatgggagttgccgccagattctgacatggatctgaatctgattgagcaggcaccctgaccgtggccgagaag ctgcagcgcgacttcctggtccagtggcgccgcgtgagtaaggccccggaggccctcttctttgttcagttcgagaagggcg agtcctacttccacctccatattctggtggagaccacgggggtcaaatccatggtgctgggccgcttcctgagtcagattaggg acaagctggtgcagaccatctaccgcgggatcgagccgaccctgcccaactggttcgcggtgaccaagacgcgtaatggcg ccggaggggggaacaaggtggtggacgagtgctacatccccaactacctcctgcccaagactcagcccgagctgcagtgg gcgtggactaacatggaggagtatataagcgcgtgtttaaacctggccgagcgcaaacggctcgtggcgcacgacctgacc cacgtcagccagacccaggagcagaacaaggagaatctgaaccccaattctgacgcgcctgtcatccggtcaaaaacctcc gcacgctacatggagctggtcgggtggctggtggaccggggcatcacctccgagaagcagtggatccaggaggaccagg cctcgtacatctccttcaacgccgcctccaactcgcggtcccagatcaaggcgctctggacaatgccggcaagatcatggc gctgaccaaatccgcgcccgactacctggtaggcccgctccgcccgccgacattaaaaccaaccgcatttaccgcatcctg gagctgaacggctacgaccctgcctacgccggctccgtctttctcggctgggcccagaaaaggttcggaaaacgcaacacc atctggctgtttgggccggccaccacgggcaagaccaacatcgcggaagccatcgcccacgccgtgccctcctacggctgc gtcaactggaccaatgagaactttccttcaacgattgcgtcgacaagatggtgatctggtgggaggagggcaagatgacgg ccaaggtcgtggagtccgccaaggccattctcggcggcagcaaggtgcgcgtggaccaaaagtgcaagtcgtccgcccag atcgatcccaccccgtgatcgtcacctccaacaccaacatgtgcgccgtgattgacgggaacagcaccaccttcgagcacc agcagccgttgcaggaccggatgttcaaatttgaactcacccgccgtctggagcatgactttggcaaggtgacaaagcagga agtcaaagagttcttccgctgggcgcaggatcacgtgaccgaggtggcgcatgagttctacgtcagaaagggtggagccaa caagagacccgcccccgatgacgcgggataaaagcgagcccaagcgggcctgcccctcagtcgcggatccatcgacgtca gacgcggaaggagctccggtggactttgccgacaggtaccaaaacaaatgttctcgtcacgcgggcatgcttcagatgctgtt tccctgcaaaacatgcgagagaatgaatcagaatttcaacatttgcttcacgcacgggaccagagactgttcagaatgtttcccc ggcgtgtcagaatctcaaccggtcgtcagaaagaggacgtatcggaaactctgtgccattcatcatctgctgggcgggctcc cgagattgcttgctcggcctgcgatctggtcaacgtggatctggatgactgtgtttctgagcaataaatgacttaaaccaggtatg gctgccgatggttatcttccagattggctcgaggacaacctctctgagggcattcgcgagtggtgggacttgaaacctggagc cccgaaacccaaagccaaccagcaaaagcaggacgacggccgggtctggtgcttcctggctacaagtacctcggaccctt caacggactcgacaaggggagcccgtcaacgcggcggatgcagcggccctcgagcacgacaaggcctacgaccagca gctcaaagcgggtgacaatccgtacctgcggtataaccacgccgacgccgagtttcaggagcgtctgcaagaagatacgtct tttgggggcaacctcgggcgagcagtcttccaggccaagaagagggttctcgaaccttttggtctggttgaggaaggtgctaa gacggctcctggaaagaaacgtccggtagagcagtcgccacaagagccagactcctcctcgggcattggcaagacaggcc agcagcccgctaaaaagagactcaattttggtcagactggcgactcagagtcagtccccgacccacaacctctcggagaacc tccagcaaccccgctgctgtgggacctactacaatggcttcaggcggtggcgcaccaatggcagacaataacgaaggcgc cgacggagtgggtaatgcctcaggaaattggcattgcgattccacatggctgggcgacagagtcatcaccaccagcacccg -continued

```
aacatgggccttgcccacctataacaaccacctctacaagcaaatctccagtgcttcaacgggggccagcaacgacaaccac tacttcggctacagcaccccctgggggtattttgatttcaacagattccactgccatttctccaccacgtgactggcagcgactcat caacaacaattggggattccggcccaagagactcaacttcaagctcttcaacatccaagtcaaggaggtcacgacgaatgatg gcgtcacgaccatcgctaataaccttaccagcacggttcaagtcttctcggactcggagtaccagttgccgtacgtcctcggct ctgcgcaccagggctgcctccctccgttcccggcggacgtgttcatgattccgcagtacggctacctaacgctcaacaatggc agccaggcagtgggacggtcatcctttttactgcctggaatatttcccatcgcagatgctgagaacgggcaataactttaccttca gctacaccttcgaggacgtgcctttccacagcagctacgcgcacagccagagcctggaccggctgatgaatcctctcatcga ccagtacctgtattacctgaacagaactcagaatcagtccggaagtgcccaaaacaaggacttgctgtttagccgggggtctc cagctggcatgtctgttcagcccaaaaactggctacctggaccctgttaccggcagcagcgcgtttctaaaacaaaaacagac aacaacaacagcaactttacctggactggtgcttcaaaatataaccttaatgggcgtgaatctataatcaaccctggcactgctat ggcctcacacaaagacgacaaagacaagttctttcccatgagcggtgtcatgattttttggaaaggagagcgccggagcttcaa acactgcattggacaatgtcatgatcacagacgaagaggaaatcaaagccactaaccccgtggccaccgaaagatttgggac tgtggcagtcaatctccagagcagcagcacagaccctgcgaccggagatgtgcatgttatgggagccttacctggaatggtgt ggcaagacagagacgtatacctgcagggtcctatttgggccaaaattcctcacacggatggacactttcacccgtctcctctca tgggcggctttggacttaagcacccgcctcctcagatcctcatcaaaaacacgcctgttcctgcgaatcctccggcagagttttc ggctacaaagtttgcttcattcatcacccagtattccacaggacaagtgagcgtggagattgaatgggagctgcagaaagaaa acagcaaacgctggaatcccgaagtgcagtatacatctaactatgcaaaatctgccaacgttgatttcactgtggacaacaatg gactttatactgagcctcgccccattggcacccgttacctcacccgtccctgtaattgtgtgttaatcaataaaccggttaattcg tgtcagttgaactttggtctcatgtcgttattatcttatctggtcaccatagcaaccggttacacattaactgcttagttgcgcttcgc gaataccccctagtgatggagttgcccactccctctatgcgcgctcgctcgctcggtggggccggcagagcagagctctgccg tctgcggacctttggtccgcaggcccaccgagcgagcgagcgcgcatagagggagtgggcaa
```

(forward primer for amplifying periostin)-

SEQ ID NO: 8 tccgtgttctgctgtggagtgatt (reverse primer for amplifying periostin)-

SEQ ID NO: 9 tagggatctctctgccttctgtct

Other useful sequences include the cap sequences of the useful AAV serotype vectors of the invention. For example, the cap sequence of AAV9 comprises nucleotide residues 2116-4329 of SEQ ID NO:1. Therefore, the invention encompasses the use of nucleotide residues 2116-4329 of SEQ ID NO:1 as the base for a recombinant AAV9 vector of the invention.

The present invention encompasses the use of human sequences as well as sequences from other species where their use produces the effects described herein.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGURE LEGENDS

FIG. 1A-E. AAV expression cassettes containing a modified periostin promoter and transgenic mouse strains. A modified periostin promoter was constructed by PCR amplification of regions surrounding the 804 bp enhancer and 423 bp minimal periostin promoter as described by Lindsley et al. These were cloned into plasmids containing: (A) a GFP reporter, pAPGFP; (B) a Cre recombinase gene, codon optimized for eukaryotic expression and with target sequences for miRNA-122 inserted into the 3' untranslated region to prevent transgene expression in the liver, pAPiCre-miR122; and (C) a luciferase reporter containing miRNA-122 target sites in the 3' untranslated region of luciferase, pAPLuc-miR122. All expression cassettes contained an SV40 polyadenylation signal. In addition, two transgenic mouse lines were used to test AAV carrying pAPiCre-miR122. When Cre is expressed in these strains it recognizes the LoxP sites flanking a transcriptional stop sequence and removes the stop sequence, allowing expression of the reporter gene. (D) B6.Cg-Gt(ROSA) 26Sor$^{tm6(CAG-ZsGreen1)Hze}$/J mice, abbreviated Flox-GFP and on a C57Bl/6 background, express ZsGreen1, an enhanced green fluorescent protein, from the CMV enhanced chicken beta-actin promoter (CAG). (E) FVB.129S6(B6)-Gt(ROSA)26Sor$^{tm1(Luc)Kae1}$/J mice, abbreviated Flox-Luc and on an FVB background, express luciferase under control of the ROSA26 promoter.

Figures 2A, 2B:
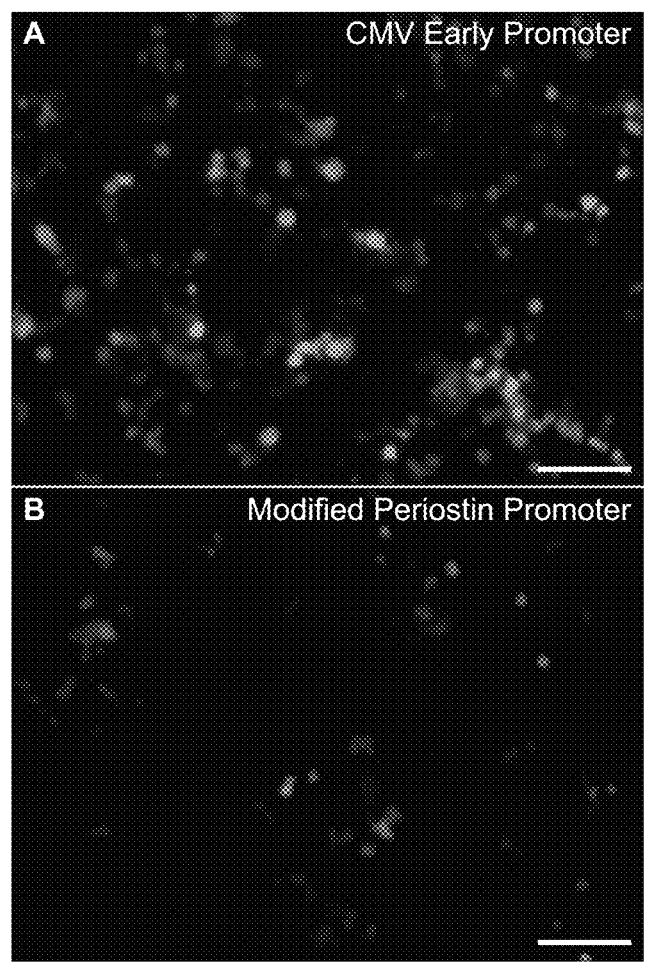

FIG. 2A-B. In vitro expression of GFP from the periostin promoter. The ability of the modified periostin promoter to program expression was analyzed in vitro by transfecting AAV-293 cells via the calcium phosphate method with a plasmid expressing (A) GFP from the CMV early promoter or (B) pAPGFP, using the modified periostin promoter. Cells were monitored until day 3 and photographed by fluorescence microscopy to confirm GFP expression. Scale bars equal 50 microns.

FIG. 3A-D. AAV-mediated expression of Cre from the periostin promoter programs robust cardiac GFP expression in mice after MI but not in non-infarcted mice, and unexpectedly AAV9 activates expression in more cells than AAV6. (A) GFP expression in an 8-week old non-infarcted Flox-GFP mouse 4 weeks after injection with $1\times10^{11}$ vg AAV6-pAPiCre. A typical 6 µm short-axis section from this mouse had 0-2 GFP-positive cells, compared to (B) a representative 9-week old mouse (n=3) injected with the same AAV vector 2 days after reperfused MI, which shows numerous GFP-positive cells the infarct (top two-thirds of the field-of-view) and border (bottom third of the field-of-view) zones 9 days after ischemic injury. Scale bars=50 microns. (C) Mosaic micrograph of a cardiac section from a representative (n=3) mouse treated with AAV6-pAPiCre shows a lower cellular hit-rate compared to (D) a representative (n=3) 13-week old mouse treated with AAV9-pAPiCre-miR122. Infarct zones (devoid of autofluorescence) are outlined with fine white lines. Scale bars=0.5 mm.

FIG. 4A-B. Mice treated with AAV9 two days after MI show higher luciferase expression than mice that receive AAV at reperfusion. 10-12 week old Flox-Luc mice were injected at reperfusion (n=2) or at day 2 (n=3) after reperfused MI with $1.5\times10^{11}$ vg AAV9 carrying pAPiCre-miR122 and imaged at days 7 and 9 post-MI. (A) Bioluminescence images from day 7 post-injection showing mice injected at reperfusion (two on left) and at day 2 post-MI (three on right). (B) Quantification of bioluminescence intensity shows that mice injected at 2 days post-MI (D2) have approximately 2-fold greater expression than mice injected at reperfusion (D0; p=0.083 by Kruskal-Wallis analysis).

FIG. 5A-F. Cre-mediated gene expression in the infarct zone on days 5, 9, and 21 post-MI. To track Cre-mediated GFP-positive cells over time, 12-13 week old Flox-GFP mice were injected 2 days post-MI with $1\times10^{11}$ vg AAV9 carrying pAPiCre-miR122. Cre-mediated GFP expression was analyzed on (A-B) day 5 (n=3), (C-D) day 9 (n=3), and (E-F) day 21 (n=2) post-MI. The low-power short-axis micrographs at left show the entire extent of the left ventricle with infarct zones outlined in white, while the high-power micrographs at right show magnifications of the areas indicated by white rectangles. On day 5 post-MI, GFP-positive cells appear to be localized primarily to the periphery of the infarct zone, while by day 9 more GFP-positive cells are visible, and more cells have localized to the infarct zone (FIG. 5C-D). Day 21 (FIGS. 5E-F) shows the greatest number of cells, with a pattern similar to day 9. Scale bars=0.5 mm for (A), (C) and (E) and 100 microns for (B), (D) and (F).

FIG. 6A-C. Periostin mediates long-term gene expression in the infarct and border zones after reperfused MI. $3\times10^{11}$ vg AAV9-pAPLuc-miR122 were injected into 15 week old C57Bl/6 mice two days after reperfused MI. Mice were subjected to bioluminescence imaging on days 8, 19, 26, 33, 47, and 62 post-injection, and showed increasing cardiac gene expression for two out of three mice from (A) day 8 to (B) day 47, with a decline in expression in all groups by day 62, as shown in (C).

FIG. 7A-F. GFP-positive cells in the infarct and border zones express myofibroblast markers. Short-axis cardiac sections showing infarct zones from Flox-GFP mice treated with AAV9 were analyzed via immunofluorescence 5, 9 and 21 days after MI. At day 21 post-MI, (A) the majority (58±3%, or $3.9\pm0.7\times10^4$ cells/mm$^3$ of infarct tissue) of GFP-positive cells (green) also expressed Myosin IIb (red); while few GFP-positive cells expressed the myofibroblast markers (B) DDR2 (red; 6±1% co-localization, or $2.4\pm0.3\times10^3$ cells/mm$^3$ of infarct tissue) or (C) α-smooth muscle actin (α-SMA, red; 1±1% co-localization, or $7.8\pm4.5\times10^2$ cells/mm$^3$ of infarct tissue). (D) Occasional GFP-positive cells ($1.2\pm0.2\times10^3$ cells/mm$^3$ of infarct tissue; red and blue boxes) were detected in the infarct (pictured here) and border zones that lacked the spindle-shaped morphology characteristic of myofibroblasts and failed to stain with antibodies against prototypical myofibroblast markers. (E) and (F) show magnified views of the red and blue boxes, respectively, from 7D. This subpopulation of GFP cells was identified as cardiomyocyte-like by virtue of the distinct sarcomeric pattern displayed throughout their cytoplasm. Scale bars=100 microns in (A)-(D); 25 microns in (E)-(F).

FIG. 8A-F (also referred to as Supplementary Figure and Supplementary FIG. 1A-F). Short-axis cardiac sections from Flox-GFP mice injected 2 days post-MI with 1×1011 vg AAV9 carrying pAPiCre-miR122 and analyzed by immunofluorescence 21 days after MI showing: (A) overlay of GFP-positive cells in the infarct zone with DAPI stain to detect nuclei. (B) A 4× magnification of the region indicated by the white box in Panel A, where the combination of DAPI and GFP yield aqua nuclei in the GFP-positive cells. (C) Overlay of GFP-positive cells with an antibody against PECAM, a marker for endothelial cells, in the infarct (between the dotted white lines) and border zones. (D) A 4× magnification of the region indicated by the white box in Panel C. Note that the vessel in the middle of the image stains positive for PECAM, and that there is little or no overlap of GFP-positive cells with PECAM. (E) Overlay of GFP-positive cells with myoglobin, a marker for cardiomyocytes, in the infarct (between the dotted white lines) and border zones. (F) A 4× magnification of the region indicated by the white box in Panel E. Note that one GFP-positive cell co-stains for myoglobin, with striations slightly visible (arrow). All scale bars=100 microns. (A and B) DAPI. (C and D) PECAM. (E and F) Myoglobin.

DETAILED DESCRIPTION

Abbreviations and Acronyms

AAV—adeno-associated viral/virus
Ant—anterior
bp—base pair
CHO—Chinese hamster ovary
CMV—cytomegalovirus
cTnT—cardiac troponin-T
eGFP—enhanced green fluorescent protein
ECL—*Erythrina cristagalli* lectin (also used for the abbreviation of enhanced chemiluminescence
EcSOD—extracellular superoxide dismutase
EDV—end-diastole
EF—ejection fraction
eGFP—enhanced green fluorescent protein
ESV—end-systole
FSG—fish skin gelatin
GA—gastrocnemius muscle
Gd-DTPA—gadolinium diethylenetriamine pentaacetic acid
GFP—green fluorescent protein HLI—hindlimb ischemia
I—ischemic
IM—intramuscular
Inf—inferior
IR—ischemia reperfusion
ITR—inverted terminal repeat
IV—intravenous
IVIS—in vivo bioluminescence imaging
LAD—left anterior descending coronary artery (in humans also referred to as anterior interventricular artery)
Lat—lateral
LGE—late gadolinium enhanced
LV—left ventricle
LVEDV—left ventricular end-diastolic volume
LVESV—left ventricular end-systolic volume
MAL I—*Maackia amurensis* lectin
MCK—muscle creatine kinase
MI—myocardial infarction
miR—micro-RNA (also referred to as miRNA)
miRNA—micro-RNA (also referred to as miR)
NAD—neuraminidase
NI—non-ischemic
nt—nucleotide
PAD—peripheral arterial disease
rAAV—recombinant AAV
Sep—septal
SMemb—embryonic form of smooth muscle myosin heavy chain
ssDNA—single-stranded DNA
TA—tibialis anterior
TNT—troponin T
vg—vector genome or viral genome Definitions In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue", and may refer to a free amino acid and to an amino acid residue of a peptide. It will be apparent from the context in which the term is used whether it refers to a free amino acid or a residue of a peptide.

Amino acids have the following general structure:

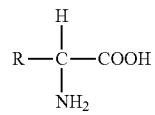

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog", or "analogue" of a chemical compound is a compound that, by way of example, resembles another in structure but is not necessarily an isomer (e.g., 5-fluorouracil is an analog of thymine).

The term "antagomir" refers to a small RNA or DNA (or chimeric) molecule to antagonize endogenous small RNA regulators like microRNA (miRNA). These antagonists bear complementary nucleotide sequences for the most part, which means that antagomirs should hybridize to the mature microRNA (miRNA). They prevent other molecules from binding to a desired site on an mRNA molecule and are used to silence endogenous microRNA (miR). Antagomirs are therefore designed to block biological activity of these post-transcriptional molecular switches. Like the preferred target ligands (microRNA, miRNA), antagomirs have to cross membranes to enter a cell. Antagomirs also known as anti-miRs or blockmirs.

An "antagonist" is a composition of matter which when administered to a mammal such as a human, inhibits a biological activity attributable to the level or presence of a compound or molecule of interest in the subject.

The term "antibody", as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain", as used herein, refers to the larger of the two types of polypeptide chains present in all antibody molecules.

An "antibody light chain", as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "associated with ischemia" as used herein means that an injury, disease, or disorder that is being treated or which is being prevented either develops as a result of ischemia or ischemia develops as a result of the injury disease or disorder, i.e., the two are closely linked.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner", as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, CSF, blood, serum, plasma, gastric aspirates, throat swabs, skin, hair, tissue, blood, plasma, serum, cells, sweat and urine.

"Blood components" refers to main/important components such as red cells, white cells, platelets, and plasma and to other components that can be derived such as serum.

As used herein, the term "carrier molecule" refers to any molecule that is chemically conjugated to the antigen of interest that enables an immune response resulting in antibodies specific to the native antigen.

A "chamber", as used herein, refers to something to which a solution can be added, such as a tube or well of a multiwell plate, etc.

As used herein, the term "chemically conjugated", or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound", as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

As used in the specification and the appended claims, the terms "for example", "for instance," "such as", "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

The term "growth factor" as used herein means a bioactive molecule that promotes the proliferation of a cell or tissue. Growth factors useful in the present invention include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue.

TGF, for example, may promote growth and/or differentiation of a cell or tissue. Note that many factors are pleiotropic in their activity and the activity can vary depending on things such as the cell type being contacted, the state of proliferation or differentiation of the cell, etc.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "improved blood flow," as used herein, refers to increased blood flow in a subject being treated according to the methods of the invention compared with the flow in a subject with an otherwise identical injury or condition not being treated according to the methods of the invention. Improved flow is determined by methods such as those described herein and can include less stasis, less sludging, or a combination of both, in the subject being treated compared with the untreated subject.

The term "inhibit", as used herein, refers to the ability of a vector, transgene, or compound of the invention to reduce or impede a described function. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

The term "inhibit a complex", as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, systemic, enteral, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

The term "injury" refers to any physical damage to the body caused by violence, accident, trauma, or fracture, etc., as well as damage by surgery.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "ischemia" as used herein refers to a local anemia due to mechanical obstruction of the blood supply, which gives rise to inadequate circulation of the blood to an organ, tissue, or region of an organ or tissue.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Left ventricle remodeling associated with an injury, disease, or disorder" means change or repair in the left ventricle of the heart. In lower animals with different chambers the remodeling may be in a different chamber.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, or be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

MicroRNAs are generally about 16-25 nucleotides in length. In one aspect, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "modulate", as used herein, refers to changing the level of an activity, function, or process. The term "modulate" encompasses both inhibiting and stimulating an activity, function, or process.

The term "muscle-specific" is used, where appropriate, interchangeably with "tissue-specific" or "tissue-preferential" and refers to the capability of regulatory elements, such as promoters and enhancers, to drive expression of transgenes exclusively or preferentially in muscle tissue or muscle cells regardless of their source.

The term "myocyte", as used herein, refers a cell that has been differentiated from a progenitor myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil).

As used herein, the term "nucleic acid" encompasses RNA as well as single and double-stranded DNA and cDNA. Furthermore, the terms, "nucleic acid", "DNA", "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "per application" as used herein refers to administration of a compositions, drug, or compound to a subject.

The term "pharmaceutical composition" shall mean a composition comprising at least one active ingredient, whereby the composition is amenable to investigation for a specified, efficacious outcome in a mammal (for example, without limitation, a human) Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease, or is done before a specific surgical procedure, etc.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell". A gene which is expressed in a recombinant host cell wherein the gene comprises a recombinant polynucleotide produces a "recombinant polypeptide".

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

A "recombinant adeno-associated viral (AAV) vector comprising a regulatory element active in myofibroblasts" refers to an AAV that has been constructed to comprise a new regulatory element to drive expression or tissue-specific expression in myofibroblasts of a gene of choice or interest.

As described herein such a constructed vector may also contain at least one promoter and optionally at least one enhancer as part of the regulatory element and the recombinant vector may further comprise additional nucleic acid sequences, including those for other genes, including therapeutic genes of interest.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample", as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytic ally cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%.

The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of analysis, diagnosis, or treatment is an animal. Such animals include mammals, preferably a human.

As used herein, a "subject in need thereof" is a patient, animal, mammal, or human who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO$_4$, 1 mM EDTA at 50° C. with washing in 2× standard saline citrate (SSC), 0.1% SDS at 50° C.; preferably in 7% (SDS), 0.5 M NaPO$_4$, 1 mM EDTA at 50° C. with washing in 1×SSC, 0.1% SDS at 50° C.;

preferably 7% SDS, 0.5 M NaPO$_4$, 1 mM EDTA at 50° C. with washing in 0.5×SSC, 0.1% SDS at 50° C.; and more preferably in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide that has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "topical application", as used herein, refers to administration to a surface, such as the skin. This term is used interchangeably with "cutaneous application" in the case of skin. A "topical application" is a "direct application".

The term "transfection" is used interchangeably with the terms "gene transfer", transformation," and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

The term "transgene" is used interchangeably with "inserted gene," or "expressed gene" and, where appropriate, "gene". "Transgene" refers to a polynucleotide that, when introduced into a cell, is capable of being transcribed under appropriate conditions so as to confer a beneficial property to the cell such as, for example, expression of a therapeutically useful protein. It is an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

Where appropriate, the term "transgene" should be understood to include a combination of a coding sequence and optional non-coding regulatory sequences, such as a polyadenylation signal, a promoter, an enhancer, a repressor, etc.

The term to "treat", as used herein, means reducing the frequency with which symptoms are experienced by a patient or subject or administering an agent or compound to reduce the frequency with which symptoms are experienced. As used herein, the term "treating" can include prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat", as used herein, means reducing the frequency with which symptoms are experienced by a patient or subject or administering an agent or compound to reduce the frequency with which symptoms are experienced.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear, break, or rupture to a tissue or cell layer. A wound may occur by any physical insult, including a surgical procedure or as a result of a disease, disorder condition.

EMBODIMENTS

In one embodiment, the present invention provides for efficiently transducing cardiac myofibroblasts in vivo using a recombinant AAV. In one embodiment, the present invention provides for efficiently transducing cardiac fibroblasts by AAV. In one aspect, the present invention provides compositions and methods for inducing cardiac fibroblasts to differentiate into myofibroblast-like cells. In one aspect, the method is not efficient in transducing cardiomyocytes.

The present invention provides compositions and methods useful for increasing myofibroblast activity to treat cardiac injuries, diseases, or disorders. In one aspect, the injury is myocardial infarction.

In one embodiment, the compositions and methods of the invention are useful for transdifferentiating myofibroblasts into cardiomyocytes. In one aspect, the compositions and methods of the invention are useful for transdifferentiating myofibroblasts into cardiomyocytes after an injury. In one aspect, the injury is myocardial infarction. In one aspect, the AAV is administered after a myocardial infarction has occurred.

In one aspect, the subject animal is a mammal. In one aspect, the mammal is a human. The compositions and methods of the invention can be used on many types of animals, including livestock, pets, birds, cats, dogs, reptiles, and amphibians, including animals in zoos.

Some useful adeno-associated viruses include, but are not limited to:

AAV9—NCBI Accession number AX753250;
AAV8—NCBI Accession number NC_006261; and
AAV6—NCBI Accession Number AF028704.1.

Although AAVs such as AAV9 and AAV8 may target some tissues with higher specificity than other tissues, the use of tissue or cell specific enhancers and promoters as part of the vector can help to ensure that the genes of interest are expressed in the desired cell or tissue.

In one aspect, the AAV9 cap sequence can be used in combination with elements from other AAV serotypes.

In one embodiment, the present invention encompasses the use of AAV8 and AAV8 capsids and other AAV serotype vectors and their capsids for targeting cardiac myofibroblasts. In one aspect, they are used shortly after a myocardial infarction, for example, within hours of the infarction. This includes administration at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, and 95 hours after the infarction. Administration can also be done at about 1, 2, 3, 4, 5, 6, or 7 days after the injury or pursuant to a disease or disorder. They can be administered subsequent to other cardiac injuries as well.

The natural tissue tropism of the various AAV serotypes can be exploited to favor gene delivery to one organ over another. This tropism is based on the viral capsids recognizing specific viral receptors expressed on specific cell types, thus allowing a degree of cell specific targeting within a given organ. Cell-specific expression may be further aided by the use of tissue-specific promoters conferring gene expression restricted to a specific cell type. This is desirable for gene therapy applications targeting organ specific diseases, as this will help avoid any possible harmful side effects due to gene expression in off target organs.

It can be seen that various types of modifications can be made to a useful nucleic acid of the invention and that the modifications can be used in various combinations.

The invention further provides cells transfected with the nucleic acid containing an enhancer/promoter combination of the invention.

Promoters may be coupled with other regulatory sequences/elements which, when bound to appropriate intracellular regulatory factors, enhance ("enhancers") or repress ("repressors") promoter-dependent transcription. A promoter, enhancer, or repressor, is said to be "operably linked" to a transgene when such element(s) control(s) or affect(s) transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, and other expression control elements, or any combination of such elements.

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis as the correct site. In contrast, the upstream promoter elements determine the rate at which transcription is initiated. These elements can act regardless of their orientation, but they must be located within 100 to 200 bp upstream of the TATA box.

The human periostin (POSTN) gene has Gene ID 10631 at the NCBI website. Its HGNC ID is 16953 and its chromosomal location is 13q13.3 (see GenBank Accession No. NC_000013, *Homo sapiens* chromosome 13, GRCh38.p7 Primary Assembly (114364328 bp DNA, linear). The *Homo sapiens* osf-2 mRNA comprising 3077 bp is GenBank Accession No. D13665. The mouse periostin gene has Gene ID 50706.

Enhancer elements can stimulate transcription up to 1000-fold from linked homologous or heterologous promoters. Enhancer elements often remain active even if their orientation is reversed (Li et al., J. Biol. Chem. 1990, 266: 6562-6570). Furthermore, unlike promoter elements, enhancers can be active when placed downstream from the transcription initiation site, e.g., within an intron, or even at a considerable distance from the promoter (Yutzey et al., Mol. and Cell. Bio. 1989, 9:1397-1405).

It is known in the art that some variation in this distance can be accommodated without loss of promoter function. Similarly, the positioning of regulatory elements with respect to the transgene may vary significantly without loss of function. Multiple copies of regulatory elements can act in concert. Typically, an expression vector comprises one or more enhancer sequences followed by, in the 5' to 3' direction, a promoter sequence, all operably linked to a transgene followed by a polyadenylation sequence.

The present invention further relies on the fact that many enhancers of cellular genes work exclusively in a particular tissue or cell type. In addition, some enhancers become active only under specific conditions that are generated by the presence of an inducer such as a hormone or metal ion. Because of these differences in the specificities of cellular enhancers, the choice of promoter and enhancer elements to be incorporated into a eukaryotic expression vector is determined by the cell type(s) in which the recombinant gene is to be expressed.

In one aspect, the regulatory elements of the invention may be heterologous with regard to each other or to a transgene, that is, they may be from different species. Furthermore, they may be from species other than the host, or they also may be derived from the same species but from different genes, or they may be derived from a single gene.

The present invention further includes the use of combinations of elements to form, for example, chimeric regulatory elements. The present invention is directed to recombinant transgenes which comprise one or more of the tissue-specific regulatory elements described herein. The chimeric tissue-specific regulatory elements of the invention drive transgene expression in muscle cells. In one aspect the muscle cell is a skeletal muscle cell. In one aspect, the muscle cell is a cardiomyocyte. The transgenes may be inserted in recombinant viral or non-viral vectors for targeting expression of the associated coding DNA sequences in muscle. In one aspect, the viral vector is an AAV.

In one embodiment, the invention further includes vectors comprising a regulatory element of the invention. In general, there are no known limitations on the use of the regulatory elements of the invention in any vector. A regulatory element comprises a promoter element and optionally an enhancer element.

The present invention is also directed to recombinant transgenes which comprise one or more operably linked tissue-specific regulatory elements of the invention.

In the present invention, the therapeutic transgene may comprise a DNA sequence encoding proteins involved in metabolic diseases, or disorders and diseases of muscle system, muscle wasting, or muscle repair. Vectors of the invention may include a transgene containing a sequence coding for a therapeutic polypeptide. For gene therapy, such a transgene is selected based upon a desired therapeutic outcome. It may encode, for example, antibodies, hormones, enzymes, receptors, or other proteins of interest or their fragments, such as, for example, TGF-beta receptor, glucagon-like peptide 1, dystrophin, leptin, insulin, pre-proinsulin, follistatin, PTH, FSH, IGF, EGF, TGF-beta, bone morphogenetic proteins, other tissue growth and regulatory factors, growth hormones, and blood coagulation factors.

The invention encompasses methods of transfecting the tissue where such methods utilize the vectors of the invention. It will be understood that vectors of the invention are not limited by the type of the transfection agent in which to be administered to a subject or by the method of administration. Transfection agents may contain compounds that reduce the electrostatic charge of the cell surface and the polynucleotide itself, or increase the permeability of the cell wall. Examples include cationic liposomes, calcium phosphate, polylysine, vascular endothelial growth factor (VEGF), etc. Hypertonic solutions containing, for example, NaCl, sugars, or polyols, can also be used to increase the extracellular osmotic pressure thereby increasing transfection efficiency. Transfection agents may also include enzymes such as proteases and lipases, mild detergents and other compounds that increase permeability of cell membranes. The methods of the invention are not limited to any particular composition of the transfection agent and can be practiced with any suitable agent so long as it is not toxic to the subject or its toxicity is within acceptable limits.

The invention further provides methods for determining magnitude of expression and AAV genome copy number. Such methods are useful for verification of the targeted cell or tissue of interest being transduced and how much of the AAV vector is present, as well as how much the gene of interest or therapeutic gene is being expressed.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double, stranded DNA, supercoiled DNA and/or triple-helical DNA; Z-DNA; miRNA, siRNA, antagomirs, and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

In one aspect, antagonists of signal transduction or expression of certain genes are used. In one aspect, the antagonist is an antisense oligonucleotide or an antagomir.

The invention provides vectors comprising a regulatory element of the invention. In some embodiments, a regulatory element of the invention is incorporated into a viral vector such as one derived from adenoviruses, adeno-associated viruses (AAV), or retroviruses, including lentiviruses such as the human immunodeficiency (HIV) virus. In one embodiment, the AAV is AAV8 or AAV9. The invention also encompasses methods of transfecting cardiac tissue where such methods utilize the vectors of the invention.

The invention further provides cells transfected with the nucleic acid containing an enhancer/promoter combination of the invention.

It will be understood that the regulatory elements of the invention are not limited to specific sequences referred to in the specification but also encompass their structural and functional analogs/homologues and functional fragments thereof. Such analogs may contain truncations, deletions, insertions, as well as substitutions of one or more nucleotides introduced either by directed or by random mutagenesis. Truncations may be introduced to delete one or more binding sites for known transcriptional repressors. Additionally, such sequences may be derived from sequences naturally found in nature that exhibit a high degree of identity to the sequences in the invention. In one aspect, a nucleic acid of 20 nt or more will be considered to have high degree of identity to a promoter/enhancer sequence of the invention if it hybridizes to such promoter/enhancer sequence under stringent conditions. Alternatively, a nucleic acid will be considered to have a high degree of identity to a promoter/enhancer sequence of the invention if it comprises a contiguous sequence of at least 20 nt, which has percent identity of at least 60%, 65%, 70%, 75%, 80%, 85%, 90%, 95%, or more as determined by standard alignment algorithms such as, for example, Basic Local Alignment Tool (BLAST) described in Altschul et al., J. Mol. Biol. 1990, 215: 403-410, the algorithm of Needleman et al., J. Mol. Biol. 1970, 48: 444-453, or the algorithm of Meyers et al., Comput. Appl. Biosci. 1988, 4: 11-17. Non-limiting examples of analogs, e.g., homologous promoter sequences and homologous enhancer sequences derived from various species, are described in the present application.

In one embodiment, the invention further includes vectors comprising a regulatory element of the invention. In general, there are no known limitations on the use of the regulatory elements of the invention in any vector. A regulatory element comprises a promoter element and optionally an enhancer element. In one embodiment, the AAV vectors of the invention may further contain a nucleic acid sequence encoding a therapeutic gene or protein. In one aspect, the vector of the invention is useful with any promoter or therapeutic gene in the cells as used.

AAV Background

In recent years, a variety of new AAV serotypes have been isolated that exhibit a wide range of tissue tropisms and provide for efficient transduction and long-term gene expression. In particular, serotypes AAV6, AAV8, and AAV9 transduce cardiomyocytes preferentially following systemic administration and provide uniform gene delivery throughout the myocardium. The most widely studied serotype, AAV2, has a prolonged lag phase of 4-6 weeks before reaching maximum gene expression in the heart. On the other hand, the more recently discovered AAV serotypes provide for an earlier onset of gene expression, approaching steady state levels within 2-3 weeks. However, the onset of gene expression provided by the newer serotypes of AAV still lags behind that achieved by adenoviral vectors. Thus, AAV2 vectors have typically been employed in preemptive gene therapy applications for MI and LV remodeling, with the AAV vector being administered several weeks before the induction of ischemia/reperfusion injury. Recently, AAV2 was directly injected into the myocardium shortly after IR to evaluate the ability of therapeutic gene delivery to preserve cardiac function in a porcine model. These studies showed that, despite the expected lag phase before gene expression, direct injection of AAV2 vectors could modulate the LV remodeling process in large animals, and could help preserve LV function. Although these studies are encouraging, delivering therapeutic genes by systemic administration would offer greater clinical relevance. However, due to the delayed onset of gene expression from conventional AAV vectors in normal myocardium, there are no reports, to date, on the use of AAV vectors to deliver gene therapy to the heart by systemic administration after ischemia and reperfusion.

AAV has a linear single-stranded DNA (ssDNA) genome of approximately 4.7-kilobases (kb), with two 145 nucleotide-long inverted terminal repeats (ITR) at the termini. The virus does not encode a polymerase and therefore relies on cellular polymerases for genome replication. The ITRs flank the two viral genes—rep (replication) and cap (capsid), encoding non-structural and structural proteins, respectively. Given the fact that the AAV ITRs contain all cis-acting elements involved in genome rescue, replication and packaging, and the fact that the AAV ITRs are segregated from the viral encoding regions, i.e., Rep and Cap gene regions, recombinant AAV vector design can follow the whole gene—removal or "gutless" vector design rationale, as in the retrovirus system. In other words, the cis-acting viral DNA elements involved in genome amplification and packaging are in linkage with the heterologous sequences of interest, whereas the region(s) encoding trans-acting viral factors involved in genome replication and virion assembly are provided in trans. Typically, rAAV particles are generated by transfecting producer cells with a plasmid (AAV cis-plasmid) containing a cloned recombinant AAV genome composed of foreign DNA flanked by the 145 nucleotide-long AAV ITRs, and a separate construct expressing in trans the viral rep and cap genes. The adenovirus helper factors, such as E1A, E1B, E2A, E4ORF6 and VA RNAs, would be provided by either adenovirus infection or transfecting into production cells a third plasmid that provides these adenovirus helper factors. Given that HEK293 cells, a commonly used AAV production cells, already contains the E1A/E1b gene, so the helper factors need to be provided are E2A, E4ORF6 and VA RNAs.

Here, only a subset of the AAV sequences were used (the VP1 CDS).

Though AAV2 is the most extensively studied serotype, and significant processes have been made about its production, for some tissues and cell types, it has low transduction efficiency. Therefore, an important area in the development of AAV as a vector concerns the engineering of altered cell tropisms to narrow or broaden rAAV2-mediated gene delivery and to increase infection efficiency. Between various AAV serotypes, the difference in transducing efficiencies could be caused by difference of their respective receptor content on target cells. A strategy to alter rAAV tropism exploits the natural capsid diversity of other serotypes, by packaging recombinant AAV2 genomes into capsids derived from other AAV isolates.

The commonly used approach employs hybrid trans-complementing constructs that encode rep from AAV2 whereas cap is derived from the other serotype displaying the cell tropism of choice. For instance, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulted rAAV is called rAAV2/5, in which the genome is based on recombinant AAV2, while the capsid is based on AAV5. It is assumed the cell or tissue-tropism displayed by this AAV2/5 hybrid virus should be the same as that of AAV5.

In one embodiment, a recombinant AAV vector of the invention is useful for targeting cardiac tissue preferentially over other tissues. In one embodiment, a recombinant AAV vector of the invention is useful for increasing expression of a gene of interest preferentially in cardiac myofibroblasts. The compositions and methods disclosed herein encompass targeting and transducing cardiac myofibroblasts with an AAV vector. The method comprises administering to a subject a pharmaceutical composition comprising an effective amount of a recombinant adeno-associated viral (AAV) vector comprising a regulatory element. The regulatory element comprises at least one promoter element and optionally at least one enhancer element. An enhancer and promoter are operably linked. The recombinant AAV vector also may optionally comprise at least one gene operably linked to a promoter element. The AAV may comprise the entire AAV genome, or a homolog or fragment thereof, such as the capsid of the particular AAV. However, it should be noted that the entire AAV genome may not be useful in some situations because of a need to make the vector replication-deficient and/or to insert genes of interest such as therapeutic genes.

The regulatory elements and the gene of interest may also be substituted with active fragments, modifications, or homologs thereof. In one aspect, the recombinant AAV vector preferentially targets skeletal muscle.

A composition of the invention may comprise additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes, or other agents may be used as adjunct therapies.

The present invention further encompasses kits comprising at least one recombinant AAV vector of the invention, an applicator, and an instructional material for the use thereof.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

Summary

We PCR-amplified regions corresponding to an enhancer and minimal promoter and combined them to create a 1395 bp periostin mini-promoter to meet the packaging limit of AAV vectors. Without wishing to be bound by any particular theory, it was hypothesized that a combination of the periostin promoter and AAV-mediated gene delivery could provide efficient expression to cardiac myofibroblasts, but not cardiomyocytes.

We tested the ability of the periostin promoter to drive Cre recombinase expression in two different strains of reporter mice that express GFP or luciferase after Cre-mediated recombination. The Cre reporter system is well suited for validating the periostin vector construct in vivo because a short duration of Cre expression can activate long-term reporter gene expression and provide for lineage tracking after differentiation or proliferation. While very infrequent Cre-mediated reporter gene expression was detected in the heart after AAV6 delivery to healthy, non-infarcted mice, robust GFP expression was seen in a potentially novel cardiac myofibroblast-like lineage when the vector was injected two-days after reperfused MI, with occasional GFP expression observed in borderzone cardiomyocyte-like cells. We then compared cellular "hit-rate" between the AAV6 and -9 capsids, and found that AAV9 activated reporter gene expression in a greater number of cells than AAV6. Cre-mediated luciferase gene expression was also found to be approximately two-fold higher after AAV9 delivery two days post-MI compared to delivery at reperfusion.

Immunofluorescence analysis of Cre-activated GFP-positive cells revealed that the majority of transduced cells expressed the myofibroblast marker myosin IIb. However, the GFP-positive cells expressed characteristic myofibroblast markers such as α-smooth muscle actin and DDR2 at much lower frequencies. Finally, the ability of the periostin promoter to provide long-term expression of luciferase in C57Bl/6 mice was examined, and robust cardiac gene expression was found to persist through 62 days post-MI (the length of the study). This work describes a system with the ability to target gene expression to a large population of myofibroblast-like cells involved in the cardiac wound healing process. This system has the potential to provide a robust platform for genetically reprogramming cardiac regeneration early after MI, which in turn might ultimately be used to reduce LV remodeling and improve clinical outcomes in the setting of ischemic heart disease.

The draft manuscript upon which this application is based has now published as Piras et al., "Systemic injection of AAV9 carrying a periostin promoter targets gene expression to a myofibroblast-like lineage in mouse hearts after reperfused myocardial infarction", Gene Therapy, 2016, 23:5: 469-478.

Materials and Methods

Plasmid Design:

Lindsley et al. described and analyzed elements of a 3.9 kilobase periostin promoter,[15] from which we amplified sequences containing an 804 bp enhancer and a 423 bp minimal promoter to create a shorter 1395 bp promoter that would fit in an AAV capsid and provide expression in cardiac fibroblasts, but not cardiomyocytes. PCR was performed with Phusion high-fidelity master mix (Thermo Scientific, Waltham, Mass.) to avoid errors in amplification. This small 1395 bp periostin promoter, which was found by Lindsley et al. to provide stronger expression than its full-length 3.9 kb wild-type counterpart, was inserted by quadruple ligation with a linker oligonucleotide in AAV plasmids carrying either a codon-optimized Cre recombinase gene,[39] or a GFP expression cassette. The new plasmids, pAPiCre and pAPGFP, were sequenced to confirm accurate amplification of the periostin promoter.

FIG. 5 of Lindsley et al.[15] provides details of the 804 bp enhancer and the 423 bp minimal promoter (see FIG. 5Biii). They define in the figure legend "nucleotide assignment given relative to the transcriptional start site (+1) of the mouse periostin promoter. Therefore, as used here: the 804 bp putative enhancer region from −2924 to −2119 bp minimal promoter; the 423 bp immediately upstream of the transcriptional start site (−423 to +1).

Figure 1A:
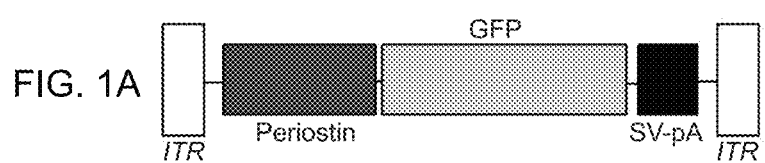
Figure 1B:
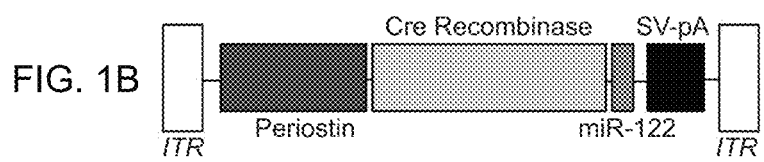
Figure 1C:
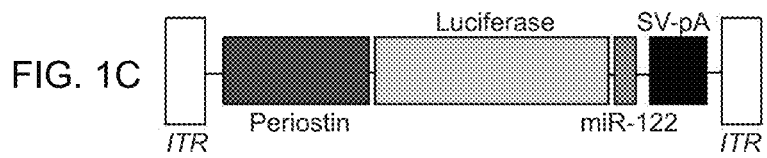

Experiments were carried out using the pAPiCre vector or a version of pAPiCre modified with three target sites for miRNA-122 (pAPiCre-miR122) to reduce off-target liver expression, as described previously.[40,41] The target sites were inserted into a BamHI site in the 3' untranslated region of Cre and confirmed to be in the correct orientation by restriction digestion and sequencing. These sites eliminated liver expression witnessed with the pAPiCre construct (data not shown). An additional plasmid containing the periostin promoter driving expression of firefly luciferase (pAPLuc-miR122) was constructed to test the ability of the periostin promoter to provide long-term gene expression in a longitudinal study. Expression cassettes used in this study are shown in FIG. 1A-C.

In Vitro Testing of pAPGFP:

To test the ability of the modified periostin promoter to drive transcription, AAV-293 cells were transfected via the calcium phosphate method with pAPGFP and compared to a plasmid expressing GFP from the cytomegalovirus (CMV) early promoter. Briefly, plasmid DNA was added to a mixture containing water and 500 mM $CaCl_2$ before mixing drop-wise with 2×HEPES-buffered saline. The transfection mixture was added to the cell media at $\frac{1}{10}^{th}$ the volume and cells were monitored until day 3 by fluorescence microscopy to confirm GFP expression.

AAV Vector Production:

Vector genomes were cross-packaged into AAV6 and -9 capsids via double or triple transfection of AAV-293 cells (Agilent Technologies Inc., Clara, Calif.), then purified by ammonium sulfate fractionation and iodixanol gradient centrifugation. Titers of the AAV vectors [viral genomes (vg)/ml] were determined by qPCR. The following primers were used for amplifying periostin: 5'-TCCGTGTTCTGCTGTG-GAGTGATT-3' (forward) and 5'-TAGGGATCTCTCTGC-CTTCTGTCT-3' (reverse). Known copy numbers ($10^5$-$10^9$) of plasmids carrying the corresponding expression cassettes were used to construct standard curves for quantification.

Also see French et al., U.S. Pat. Pub. No. 2013/0136729, published May 30, 2013 (U.S. patent application Ser. No. 13/673,351) for additional information on AAVs, particularly AAV8 and AAV9, the entirety of which is incorporated by reference herein.

Animal Procedures:

The animal protocol used in this study was approved by the University of Virginia Institutional Animal Care and Use Committee (Protocol Number: 2802) and strictly conformed to the "Guide for the Care and Use of Laboratory Animals" (NIH Publication 85-23, revised 1985). All mice were maintained on a 12/12 hr light/dark cycle at 24° C. and 60% humidity.

Figure 1D:
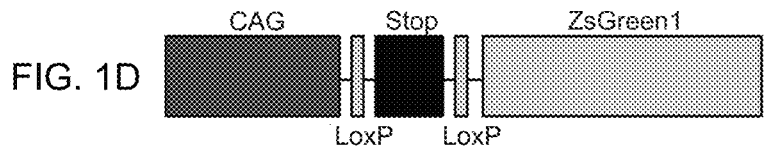
Figure 1E:
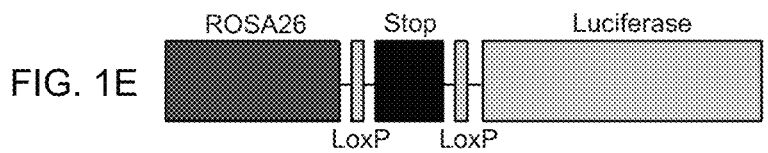

Two transgenic mouse lines were used in this study for in vivo testing of AAV carrying the periostin promoter driving Cre recombinase. FIG. 1D-E shows a summary of the transgenic expression cassettes in these mice. When Cre is expressed in these strains it recognizes LoxP sites flanking a transcriptional stop sequence between a promoter and a reporter gene and removes the stop sequence, allowing expression of the linked reporter gene. B6.Cg-Gt(ROSA) 26Sor$^{tm6(CAG-ZsGreen1)Hze}$/J (Flox-GFP) mice are on a C57Bl/6 background and express ZsGreen1, an enhanced green fluorescent protein, from the CMV-enhanced chicken beta-actin promoter (CAG) after Cre-mediated recombination.[42] FVB.129S6(B6)-Gt(ROSA)26Sor$^{tm1(Luc)Kae1}$/J (Flox-Luc) mice are on an FVB background and express luciferase under control of the ROSA26 promoter after Cre-mediated recombination.[43]

Most mice in this study were treated with AAV after reperfused myocardial infarction. Male and female mice from 8 to 15 weeks of age were anesthetized with sodium pentobarbital, placed in a supine position, and orally intubated. Core body temperature was monitored throughout the operation with a rectal thermocouple and a digital thermometer (Barnant Co, Barrington, Ill.) and maintained between 36.5-37.5° C. with a heating lamp. The heart was exposed by cutting the $3^{rd}$ and $4^{th}$ ribs with a cautery pen and the intercostal muscles with scissors. MI was induced by passing a 7-0 silk suture beneath the left anterior descending coronary artery (LAD) at the level of the lower left atrium and tying it over a piece of PE-50 tubing to achieve occlusion. Reperfusion was performed by untying the ligature and removing the tubing. Mice were injected with AAV at the time of reperfusion by intravenous injection via the jugular vein, or 2 days after MI via the tail vein. Additional groups of mice were also treated with vector 2 weeks before or in the absence of MI by tail vein injection. Mice received between $1×10^{11}$ to $3×10^{11}$ viral genomes for all studies.

Bioluminescence Imaging:

Luciferase expression was assessed in live Flox-Luc and C57Bl/6 mice using an in vivo bioluminescence imaging system (IVIS Spectrum, Caliper Life Sciences, Hopkinton, Mass.) as described previously.[11,44,45] Briefly, mice were anesthetized with isoflurane and injected with 150-300 μL of 30 mg/mL D-luciferin (Gold Biotechnologies, Inc., St. Louis, Mo.) intraperitoneally. Images were collected 10-30 minutes after substrate injection and light output was quantified using Living Image software (Caliper Life Sciences).

Tissue Analysis for Luciferase Activity:

Flox-Luc mice injected with AAV6 or -9 were euthanized on days 9-15 post-MI and their hearts were removed for analysis of luciferase activity. Luciferase activity was analyzed using the Promega (Madison, Wis.) luciferase assay kit, as described previously.[45,46] Briefly, hearts were homogenized in Promega reporter lysis buffer, incubated for 1 hour at 4° C. and centrifuged at 10,000×g for 10 minutes to collect protein extracts. A FLUOstar Optima microplate reader was used to assess relative light units per milligram of tissue.

Immunofluorescence and Image Acquisition and Analysis:

For fluorescence microscopy of Flox-GFP mice, hearts were excised 5, 9 or 21 days post-MI and fixed for one hour at room temperature in 4% PFA, rinsed in PBS, and incubated overnight at 4° C. in 30% sucrose in PBS before embedding in OCT. Six micron cryosections were cut perpendicular to the long-axis of the heart from each tissue and coverslipped using Prolong Gold anti-fade reagent with or without DAPI (Life Technologies Corp., Carlsbad, Calif.) to preserve GFP signal. The infarct zone in the short-axis sections was distinguished from viable myocardium by the low level of autofluorescence that is exhibited by viable cardiomyocytes.[47] Sections were also incubated with primary antibodies to identify markers of GFP-positive cells. Briefly, the staining protocol involved rinsing OCT from slides with PBS, and blocking with 0.5% fish skin gelatin (FSG) in PBS with 0.3 M glycine and 0.05% Tween-20 for one hour at room temperature. Primary antibodies for myosin IIb (8824; Cell Signaling Technology, Inc., Danvers, Mass.), DDR2 (sc-7555; Santa Cruz Biotechnology, Inc., Dallas, Tex.), α-smooth muscle actin (C6198; Sigma-Aldrich, St. Louis, Mo.), myoglobin (sc-25607; Santa Cruz), and PECAM (sc-1506; Santa Cruz) were incubated at dilutions ranging from 1:50 to 1:2000 for one hour at room temperature or overnight at 4° C. with 0.1% FSG in PBS. Secondary antibodies to the goat or rabbit primary antibodies labeled with Alexa Fluor 594 (Life Technologies Corp.) were incubated at dilutions of 1:100 for one hour at room temperature with 0.1% FSG in PBS. Images were acquired with an Olympus BX-41 Microscope (Olympus America, Inc., Center Valley, Pa.) with a Retiga-2000R camera (QImaging, Surrey, BC) using a FITC (41004, Chroma Technology Corp., Bellows Falls, Vt.) or Texas Red (41004, Chroma) filter set. Further imaging was performed using an Olympus IX81 inverted microscope with a 10× UPlanFLN 0.30 NA objective, Orca-AG CCD camera (Hamamatsu, Bridgewater, N.J.), automated stage (Prior Scientific, Rockland, Mass.), and IPLab software (Scanalytics, Fairfax, Va.).

Fluorescence micrographs were analyzed using ImageJ software. To determine the percentage of cells co-positive with GFP, pixel intensity thresholds were adjusted to eliminate background and the total number of GFP positive cells were counted in each image. The channel for the other markers were merged with GFP and cells with threshold intensities above background in both channels were determined to be co-positive. A total of 3 to 6 images were analyzed for each time point and each marker. Pixels were converted into microns to determine the cross-sectional area of each image, which was multiplied by the thickness of each section (i.e., 6 microns) to determine the volume. Cell counts are thus expressed in terms of cells per cubic millimeter of infarct tissue.

Statistical Analysis:

Data are expressed as mean±SEM where appropriate. Nonparametric Kruskal-Wallis analysis was used to assess significance. P<0.05 was considered significant in all comparisons.

Results

Periostin Provides GFP Expression after Transfection of 293 Cells:

The functionality of the modified periostin promoter was validated in vitro by transfecting AAV-293 cells via the calcium phosphate method with a plasmid containing an ITR-flanked expression cassette in which the modified periostin promoter drives the expression of GFP (pAPGFP: see FIG. 1 for a summary of all expression cassettes used) or a plasmid expressing GFP from the CMV early promoter. FIG. 2 shows the GFP fluorescence generated by cells transfected with the periostin promoter construct (FIG. 2A) or the CMV early promoter construct (FIG. 2B). Cells were monitored until day 3 and photographed by fluorescence microscopy to demonstrate that GFP expression from the modified periostin promoter compared favorably with the CMV early promoter.

AAV6-Mediated Expression of Cre from the Periostin Promoter Programs Robust Cardiac GFP Expression in Mice after MI but not in Normal Mice:

After confirming in vitro periostin-driven GFP expression, pAPiCre was cross-packaged into AAV6 for in vivo testing in normal (non-infarcted) mice. Two 4 week old Flox-GFP mice were injected via the tail vein with either $2.6 \times 10^{10}$ or $1 \times 10^{11}$ viral genomes. A control mouse received no injection. Successful expression of Cre recombinase was expected to result in GFP-positive cells. Mice were euthanized 4 weeks after injection and no GFP-positive cells were seen in the untreated control mouse or the mouse that received the low dose of AAV. In the mouse that received the higher dose, only a few GFP-positive cells were detected by fluorescence microscopy (i.e., typical 6 micron sections contained 0-2 GFP-positive cells, FIG. 3A).

Figures 3A, 3B, 3C, 3D:
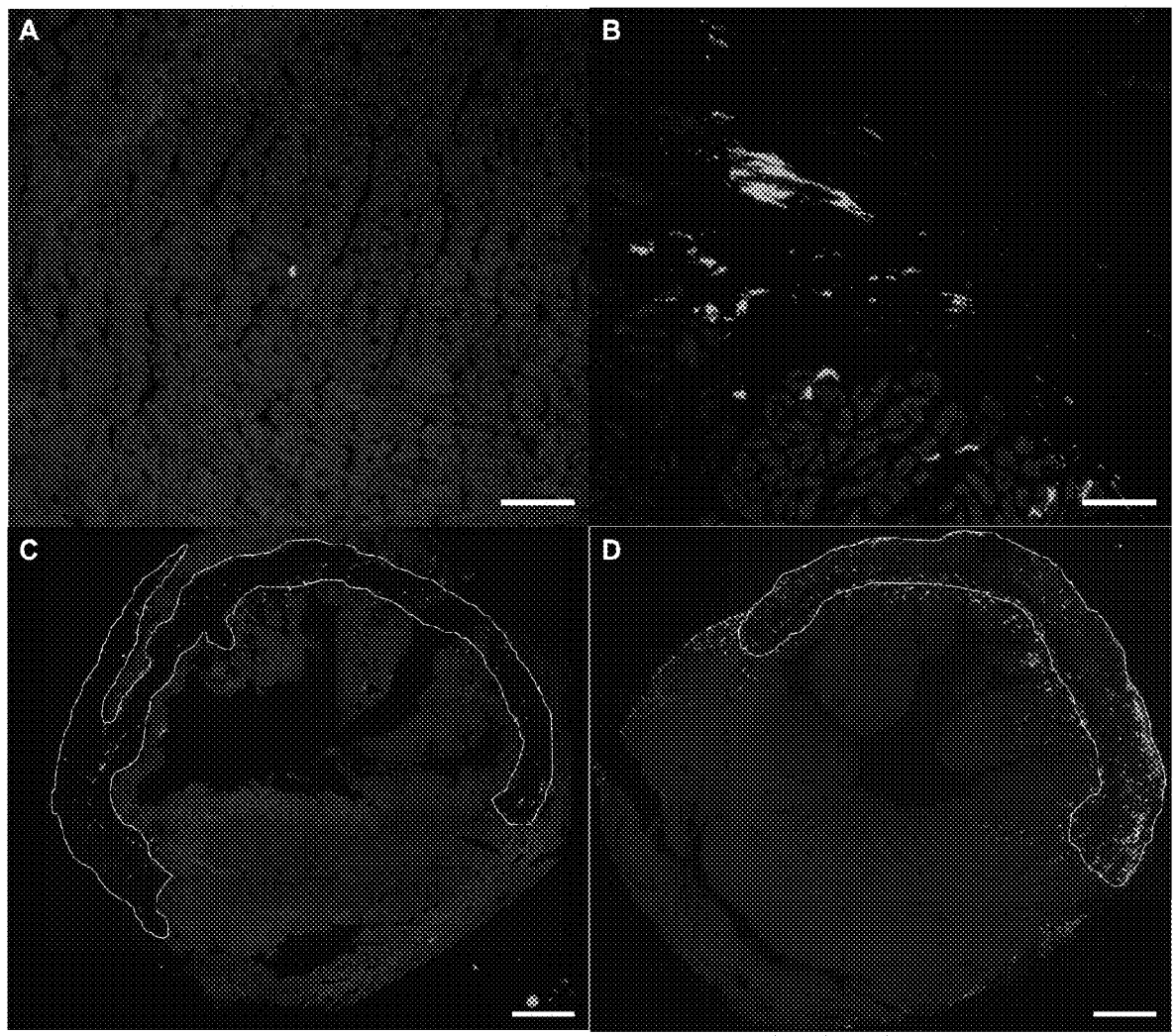

To examine whether AAV would more efficiently transduce cardiac myofibroblasts activated by ischemic injury as described previously,[9,16,17] AAV6 carrying pAPiCre was injected after reperfused MI. Three 8 week old male Flox-GFP mice were subjected to 60 minutes of coronary occlusion followed by reperfusion. A delay of two days after MI was selected to allow time for the cardiac wound healing response to initiate,[10,18] and then $1 \times 10^{11}$ vg of AAV6 carrying pAPiCre were injected into the tail vein of each mouse. One week later, the mice were euthanized and their hearts were collected for analysis by fluorescence microscopy. In contrast to the previous results obtained in non-infarcted mice, many GFP-positive cells were observed, both in the infarct and border zones of the heart (FIG. 3B). Little to no GFP expression was detected in the remote zone.

AAV9 Activates Expression in More Cells than AAV6 when Injected 2 Days Post-MI:

To compare the cellular hit-rate of AAV6 and AAV9, three 12 week old Flox-GFP mice were injected 2 days post-MI with $1 \times 10^{11}$ vg AAV9 carrying pAPiCre-miR122 (miR122 sites were incorporated to prevent liver expression, which was witnessed in early experiments with AAV6; data not shown). As before, hearts were harvested 7 days after viral delivery. FIG. 3C-D shows fluorescence micrograph mosaics of cardiac sections from mice injected with AAV6 carrying pAPiCre or AAV9 carrying pAPiCre-miR122. GFP-positive cells can be seen clearly in the infarct and border zones of each section and AAV9-treated mice had several-fold more GFP-positive cells compared to AAV6-treated mice.

Delivery of AAV9 Two Days after MI Activates Greater Luciferase Expression than AAV Delivery at Reperfusion:

10-12 week old Flox-Luc mice were injected with $1.5 \times 10^{11}$ vg AAV9 carrying pAPiCre-miR122 at reperfusion (n=2), or day 2 (n=3) after reperfused MI and imaged at days 5 and 7 post-injection. Bioluminescence imaging performed at both days 5 and 7 post-injection (FIG. 4A) indicated that mice injected at reperfusion had approximately 2-fold lower bioluminescence signal than mice injected 2 days post-MI (FIG. 4B, p=0.083 by Kruskal-Wallis analysis).

Periostin Mediates Long-Term Gene Expression in the Infarct and Border Zones:

To track Cre-mediated GFP expression over time, 12-13 week old Flox-GFP mice were injected 2 days post-MI with $1 \times 10^{11}$ vg AAV9 carrying pAPiCre-miR122. Cre-mediated GFP expression was analyzed on days 5 (n=3), 9 (n=3), and 21 (n=2) post-MI. FIG. 5 shows cardiac sections from the apexes of hearts from each time point, with infarct zone visible as a complete inner ring in each section, and no remote zone visible in the sections. On day 5 post-MI, GFP-positive cells appear to be localized primarily to the periphery of the infarct zone (FIG. 5A-B), while by day 9 more GFP-positive cells are visible, and more cells have localized to the infarct zone (FIG. 5C-D). Day 21 (FIGS. 5E-F) shows the greatest number of cells, with a pattern similar to day 9. Additional GFP-positive cells are located near the epicardial layer at each time point. More basal cardiac sections (similar to FIG. 3D) were also analyzed to confirm that the remote zone was largely free of GFP-positive cells at each time point (data not shown).

Next, to determine whether the periostin promoter was capable of providing long-term gene expression without the lineage-tracing ability of the Cre/lox system, pAPLuc-miR122 was packaged into AAV9 and $3 \times 10^{11}$ vg were injected into 15 week old C57Bl/6 mice two days after reperfused MI. Mice were subjected to bioluminescence imaging on days 8, 19, 26, 33, 47, and 62 post-injection. Imaging results from days 8 and 42 are shown in FIGS. 6A and B, respectively. Cardiac gene expression was found to increase through day 47 for two out of three mice, with a decline in expression by day 62 (FIG. 6C). Interestingly, while we previously reported that AAV9-mediated gene expression from the cardiomyocyte-specific cTnT promoter approaches a steady state maximum by 1-2 weeks after vector injection 2 days post-MI,[11] periostin-mediated luciferase expression declined sharply between 8 and 9 weeks post-injection under similar conditions: a time frame during which infarcts mature and myofibroblast activity subsides in this model system.

A final group of Flox-GFP mice were injected via tail vein three weeks prior to MI with $1\times10^{11}$ vg AAV9 carrying pAPiCre-miR122 to determine whether vector delivery before injury would lead to expression after injury comparable to the previous groups treated 2 days post-MI. Tissues were collected and analyzed for GFP expression three weeks post-MI. While Cre-mediated GFP-positive cells were visible, injection of AAV9 prior to MI led to a greatly diminished cellular hit-rate compared to mice treated post-MI, with fewer than 30 GFP-positive cells present in typical 6 μm sections (FIG. 8D (also referred to as Supplementary FIG. 1D).

Figure 7A:
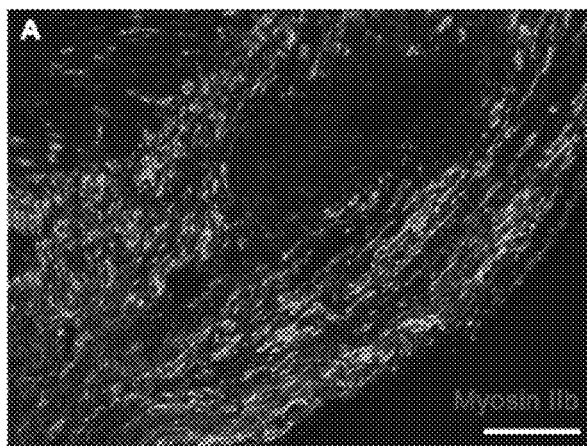
Figure 7B:
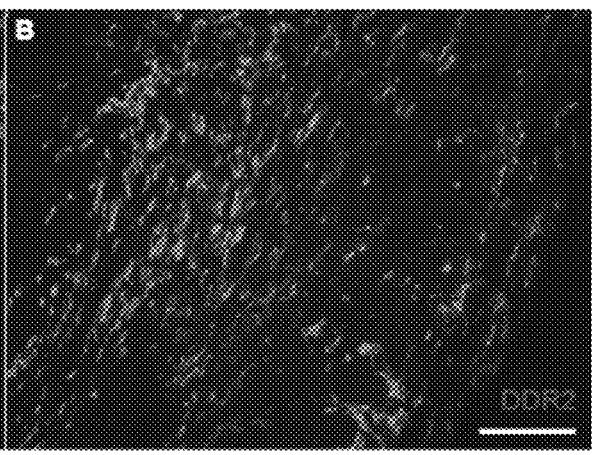
Figure 7C:
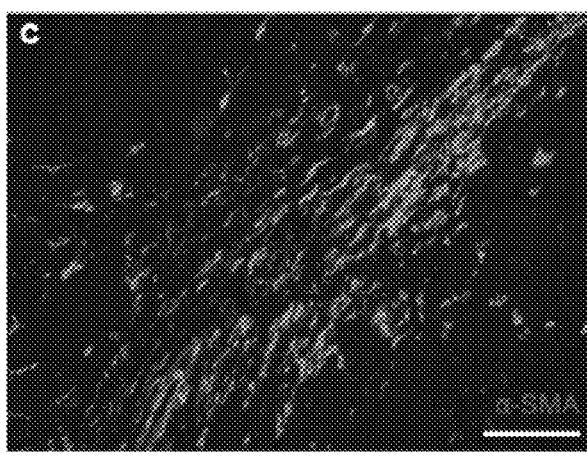

GFP-Positive Cells in the Infarct and Border Zones Express Myofibroblast Markers:

Cardiac sections from Flox-GFP mice treated with AAV9 were analyzed via immunofluorescence 5, 9, and 21 days after MI. The majority of GFP-positive cells expressed myosin IIb, the embryonic form of smooth muscle myosin heavy chain ($2.3\pm0.5\times10^4$ cells/mm$^3$ of infarct tissue, or $53\pm3\%$ at day 5; $1.4\pm0.3\times10^4$ cells/mm$^3$ of infarct tissue, or $43\pm7\%$ at day 9; and $3.9\pm0.7\times10^4$ cells/mm$^3$ of infarct tissue, or $58\pm3\%$ at day 21, FIG. 7A). Expression of myosin IIb has previously been demonstrated in the infarct and border zones after reperfused myocardial infarction and in cell culture as fibroblasts differentiate into myofibroblasts.[19-22] Therefore, myosin IIb has been considered to serve as a marker of fibroblast activation.[23] Interestingly, commonly utilized markers of cardiac fibroblasts such as α-smooth muscle actin and DDR2 showed decreasing co-localization to GFP cells over the course of the study (α-smooth muscle actin: $1.1\pm0.4\times10^4$ cells/mm$^3$ of infarct tissue, or $20\pm7\%$ at day 5; $6.9\pm0.3\times10^3$ cells/mm$^3$ of infarct tissue, or $17\pm7\%$ at day 9; and $7.8\pm4.5\times10^2$ cells/mm$^3$ of infarct tissue, or $1\pm1\%$ at day 21; DDR2: $5.4\pm2.1\times10^3$ cells/mm$^3$ of infarct tissue, or $16\pm5\%$ at day 5; $1.6\pm0.6\times10^3$ cells/mm$^3$ of infarct tissue, or $7\pm2\%$ at day 9; and $2.4\pm0.3\times10^3$ cells/mm$^3$ of infarct tissue, or $6\pm1\%$ at day 21) (FIG. 7B-C). Additional markers of fibroblasts including vimentin, periostin, and collagen types I and III provided inconclusive results due to high levels of non-specific staining in the myocardial infarct zone (data not shown). Additionally, a small subset of the GFP cells stained positive for the proliferation marker Ki-67 (data not shown).

Interestingly, we witnessed an average of $1.2\pm0.2\times10^3$ GFP-positive cardiomyocyte-like cells per cubic-millimeter of infarct tissue, and confined to the infarct borderzone, in tissues analyzed 9 days post-MI in mice treated with both AAV6 and AAV9. These cells were also present at day 21 post-MI (FIG. 7D), and contained striations characteristic of cardiomyocytes (FIGS. 7E-F) and expressed the cardiomyocyte marker myoglobin (see arrow in FIG. 8, also referred to as Supplementary FIG. 1). Additional markers for nuclei (DAPI) and endothelial cells (PECAM) are also shown in the data supplement. Note that no overlap was witnessed between GFP- and PECAM positive cells.

Discussion

The ability to provide transgene expression in cardiac myofibroblasts with adeno-associated virus would offer a variety of new opportunities for cardiac regeneration post-MI. Previous cardiac gene delivery studies employing AAV have generally reported the transduction of cardiomyocytes, which are essential for cardiac function and are most efficiently targeted in mice after systemic delivery by AAV9.[2,14] To our knowledge, no previous study has demonstrated that cardiac myofibroblasts can be efficiently transduced by AAV in vivo. Myofibroblasts are critical to the cardiac wound healing process initiated by MI because they infiltrate the infarct zone to mediate scar formation through collagen deposition and secretion of cytokines, matrix metalloproteinases, and growth factors. In addition, recent studies have shown that a cocktail of transcription factors or microRNAs can be used to transdifferentiate fibroblasts into cardiomyocytes.[24-27] The possibility of regenerating cardiomyocytes, a population of cells with very little proliferative potential or turnover, through the genetic reprogramming of other cell types has therefore become an intense area of research. Here we show, for the first time, efficient AAV-mediated transduction of, and sustained gene expression in, a potentially novel myofibroblast-like lineage abundant in the infarct and border zones (but rarely witnessed in the remote zone) after reperfused myocardial infarction.

In order to provide selective gene expression in this population, we cloned a modified periostin promoter based on previous work by Lindsley, et al.[15] Periostin is a predominantly extracellular protein found in fibroblasts and several other cell types.[9,28] It has been shown to be involved in embryonic development of the heart and is critical to repair after cardiac injury, e.g. after infarction and transverse aortic constriction.[9,16,17,29] Additionally, delivery of extracellular periostin has been reported to promote cardiac wound healing by coaxing cardiomyocytes back into the cell cycle.[30] The periostin promoter has also been used in lineage tracing of fibroblasts prior to and after MI,[31] and in myofibroblasts that were reprogrammed into cardiomyocytes after delivery of retrovirus carrying transcription factors promoting transdifferentiation.[26] Here, we have shown that a condensed 1395 bp periostin promoter is capable of driving GFP expression in 293 cells, as well as Cre recombinase and luciferase expression in vivo. Although common fibroblast markers such as α-smooth muscle actin and DDR2 were co-localized to GFP-positive cells at low frequency, the majority of the cells targeted in our in vivo study express myosin IIb (FIG. 7). Also known as the embryonic form of smooth muscle myosin heavy chain (SMemb), myosin IIb has previously been shown to be expressed by myofibroblasts after reperfused MI, and has been speculated to serve as a marker of fibroblast activation.[19,22,23]

Interestingly, when AAV was delivered to healthy Flox-GFP mice with non-infarcted hearts, very few GFP-positive cells were present compared to delivery after myocardial infarction. We initially hypothesized this was primarily a result of diminished activity of the periostin promoter in the absence of injury, which has been demonstrated by other groups.[7,16,31] However, when mice were treated 3 weeks before the onset of MI with AAV9 expressing Cre, few GFP-positive cells were present 3 weeks after MI, the same time point at which we witnessed robust GFP expression in cardiac myofibroblast-like cells from mice that were injected two days post-MI (FIG. 5E-F). One limitation of this study is that the mechanism(s) responsible for this dramatic difference in Cre-mediated GFP expression have yet to be determined. However, previous studies in conjunction with the above results indicate that a combination of two mechanisms are at play, namely the low abundance of cardiac myofibroblasts in the absence of cardiac injury, and an increase in AAV9 transduction efficiency after MI. In particular, a recent paper by Ruiz-Villalba et al. used lineage tracking to show that fibroblasts in the post-MI heart are primarily derived from epicardial mesenchymal cells.[32] They show a large increase in fibroblasts through activation and proliferation post-MI, compared to healthy control hearts, and show fibroblasts predominantly in the infarct zone with substantially fewer cells in the remote zone, as we demonstrate here. Furthermore, using AAV9 expressing GFP from a cardiac-specific promoter, our lab has shown that viable cardiomyocytes at the edge of the infarct are several orders of magnitude more susceptible to transduction than cardiomyocytes in areas remote to the ischemic region.[11] It is possible that cardiac fibroblasts in the ischemic region are likewise more susceptible to transduction, consistent with previous studies that have demonstrated increased AAV transduction in conjunction with altered activity of DNA-damage response proteins.[33-35] However, it would be more challenging to ascertain whether similar mechanisms govern Cre-mediated GFP expression given the extremely low frequency of GFP-positive cells detected in healthy mouse hearts under the conditions of this study.

Cre-mediated reporter gene expression was witnessed in Flox-GFP mice from day 5 through day 21 post-MI (FIG. 5), including prominent expression in the subepicardium. Subepicardial mesenchyme has been shown to give rise to fibroblasts and to regenerate cardiomyocytes after ischemia, albeit at extremely low frequency.[36] Additionally, Furtado et al. describe an upregulation of mesenchymal markers in an analysis of the cardiogenic transcription network in cardiac fibroblasts.[31] Importantly, Furtado et al. also show β-Gal+ fibroblasts at post-MI days 3, 7 and 14 in transgenic periostin-Cre mice that have a remarkably similar distribution to those we report here. This group also reported a homing of fibroblasts to the infarct zone between days 3 and 7, similar to the increase evident between days 5 and 9 in our study (FIGS. 5A and 5C). Furthermore, using a transgenic periostin-Cre/ZsGreen mouse strain, Furtado et al. documented cells in the infarct zone at 14 days post-MI with similar morphology to the GFP myofibroblasts described here. Another paper by Ruiz-Villalba et al., mentioned above, demonstrates homing of newly activated and proliferated fibroblasts into the infarct zone and, importantly, shows a large number of fibroblasts in the fully formed infarct scar at 30 days post-MI, consistent with our data showing an increase in expression up to (and beyond) this time point (FIG. 6).[32] Due to differences between mouse models (permanent ligation in Furtado et al. and Ruiz-Villalba et al. versus reperfused MI in our study) and gene expression techniques (transgenic mice versus AAV vectors) it is nevertheless possible that these two cell populations are non-identical.

In addition, direct expression of luciferase from the periostin promoter resulted in long-term gene expression which peaked between days 33 and 47 post-injection and declined by the end of the study at 62 days (FIG. 6). Myofibroblasts have been shown to remain in the human infarct scar for years after myocardial infarction,[37] long after the process of LV remodeling is complete. In mice, LV remodeling from a 60 minute occlusion is essentially complete within 28 days post-MI.[11,12,38] Therefore, it is possible to achieve gene expression in these myofibroblast-like cells for the majority of this therapeutic window and beyond.

Figure 7D:
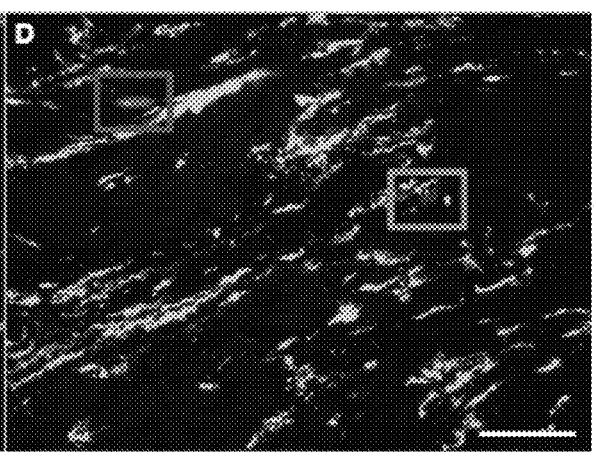
Figure 7E:
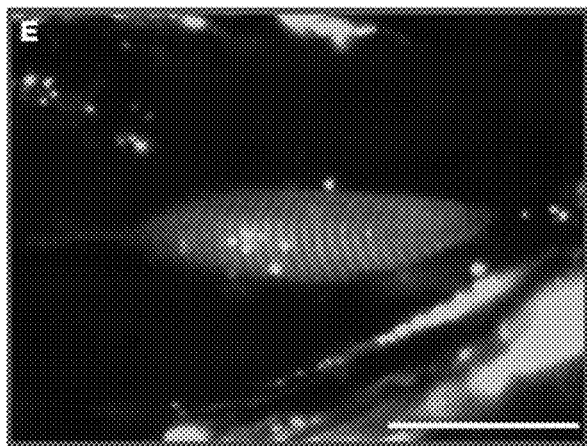
Figure 7F:
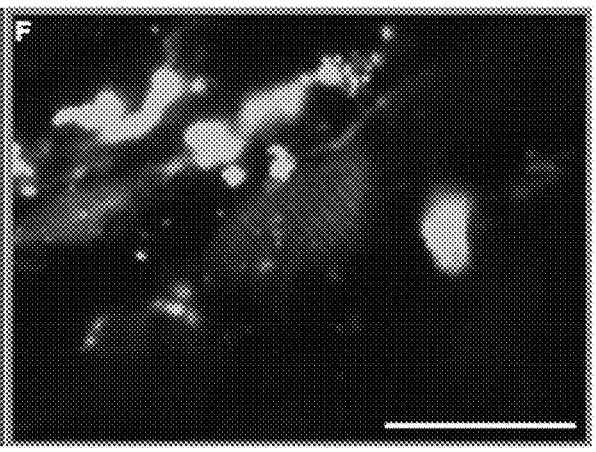
Figure 8A:
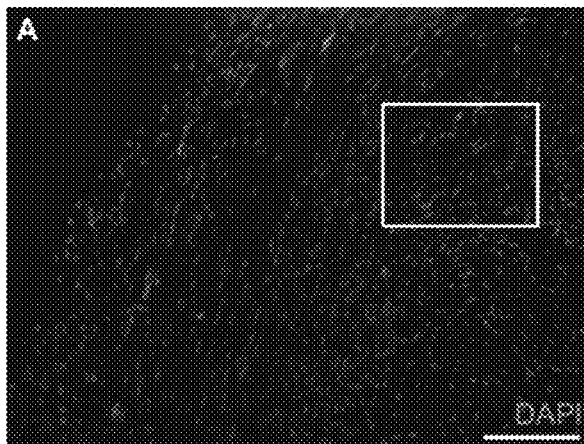
Figure 8B:
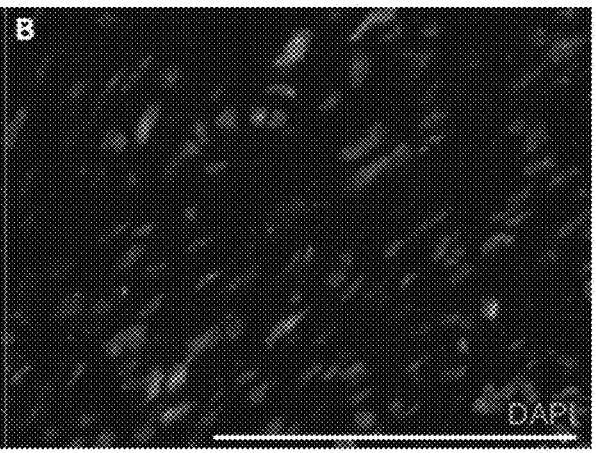
Figure 8C:
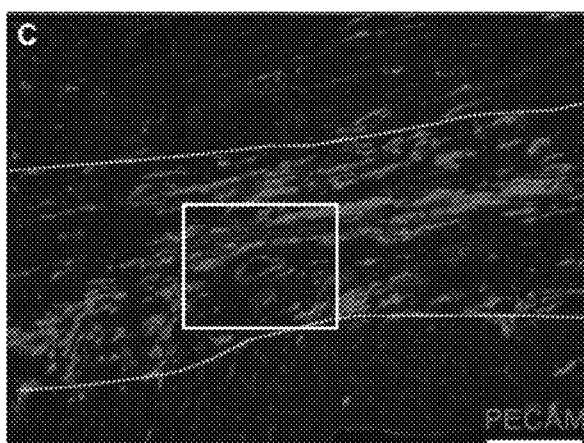
Figure 8D:
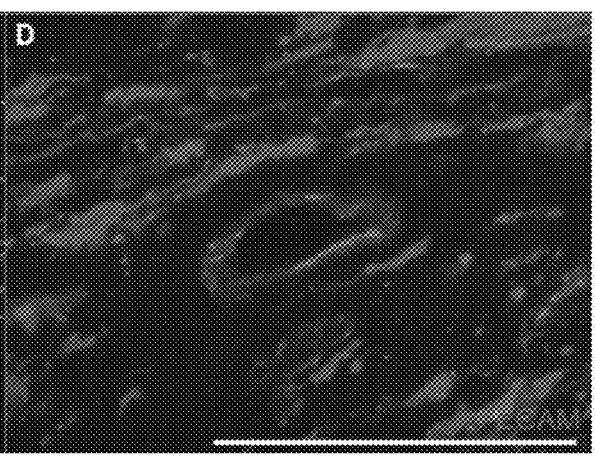
Figure 8E:
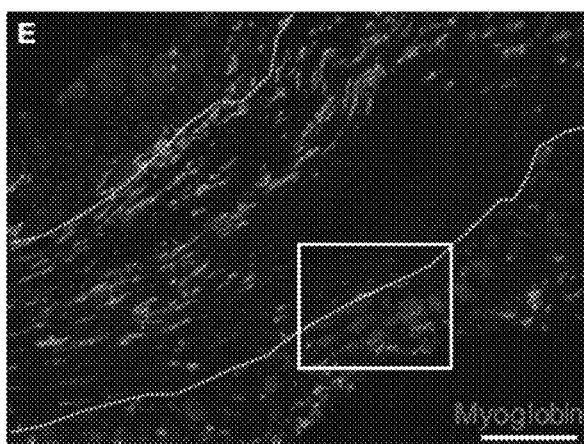
Figure 8F:
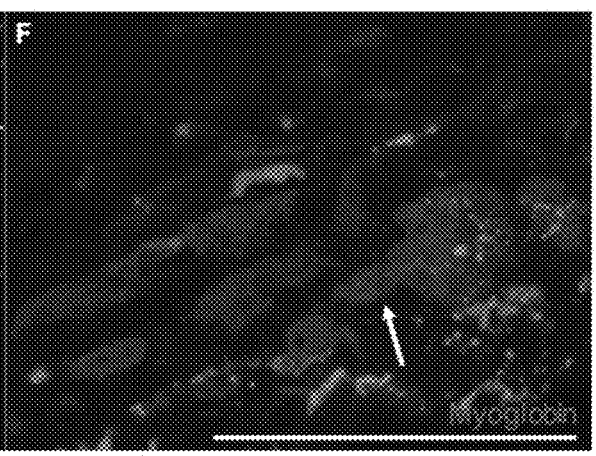

While in vivo expression is largely confined in the heart to the myofibroblast-like cells, we did witness Cre-mediated GFP expression in occasional cardiomyocyte-like cells in the infarct borderzone (FIG. 7D-F). Though periostin expression would have been required to activate expression in these cells, it is unknown whether they belong to a small population of cardiomyocytes that experience an upregulation of the periostin promoter at some point after MI, or whether they transdifferentiated from myofibroblasts that previously expressed periostin. If the AAV vectors were targeting pre-existing cardiomyocytes, one might expect to see more GFP cardiomyocytes in the remote zone and fewer GFP cardiomyocyte-like cells located immediately adjacent to GFP myofibroblast-like cells in the infarct zone. It will be important to address this question in future studies, since the approach used here may offer insight into the endogenous potential for myofibroblasts to transdifferentiate into cardiomyocytes in vivo post-MI.

This study demonstrates, for the first time, that AAV6 and -9 can target gene expression to a potentially novel myofibroblast-like lineage in the mouse heart after reperfused myocardial infarction. Using AAV9, we were able to obtain efficient expression after systemic delivery of vector 2 days post-MI, with gene expression persisting through 62 days after injection. Future studies can take advantage of a wide variety of genes to modulate the behavior of this cell population to promote cardiac regeneration while reducing scar formation after myocardial infarction. Additionally, AAV vectors carrying the periostin promoter can be constructed to express developmental transcription factors or microRNAs in order to transdifferentiate a potentially substantial population of these myofibroblast-like cells into cardiomyocytes for the purposes of cardiac regeneration. Furthermore, such myofibroblast-targeted therapies might be combined with AAV vectors that promote cell division in borderzone cardiomyocytes to create a two-pronged therapeutic approach for bioengineering the wound healing process initiated by MI. In the long-term, targeting gene therapies to these cells could be used to improve clinical outcomes after myocardial infarction.

Also see French et al., U.S. Pat. Pub. No. 2013/0136729, published May 30, 2013 (U.S. patent application Ser. No. 13/673,351) for additional information on AAVs, particularly AAV8 and AAV9, the entirety of which is incorporated by reference herein.

BIBLIOGRAPHY

1 Wu Z, Asokan A, Samulski R. Adeno-associated Virus Serotypes: Vector Toolkit for Human Gene Therapy. *Mol Ther* 2006; 14: 316-327.
2 Zincarelli C, Soltys S, Rengo G, Rabinowitz J E. Analysis of AAV Serotypes 1-9 Mediated Gene Expression and Tropism in Mice After Systemic Injection. *Mol Ther* 2008; 16: 1073-1080.
3 Prasad K-M R, Smith R S, Xu Y, French B A. A single direct injection into the left ventricular wall of an adeno-associated virus 9 (AAV9) vector expressing extracellular superoxide dismutase from the cardiac troponin-T promoter protects mice against myocardial infarction. *J Gene Med* 2011; 13: 333-341.
4 Inagaki K, Fuess S, Storm T A, Gibson G A, Mctiernan C F, Kay M A et al. Robust Systemic Transduction with AAV9 Vectors in Mice: Efficient Global Cardiac Gene Transfer Superior to That of AAV8. *Mol Ther* 2006; 14: 45-53.
5 Zak R. Development and proliferative capacity of cardiac muscle cells. *Circ Res* 1974; 35: suppl II:17-26.
6 Nag A. Study of non-muscle cells of the adult mammalian heart: a fine structural analysis and distribution. *Cytobios* 1980; 28: 41-61.
7 Souders C A, Bowers S L K, Baudino T A. Cardiac Fibroblast The Renaissance Cell. *Circ Res* 2009; 105: 1164-1176.
8 Banerjee I, Fuseler J W, Price R L, Borg T K, Baudino T A. Determination of cell types and numbers during cardiac development in the neonatal and adult rat and mouse. *Am J Physiol—Heart Circ Physiol* 2007; 293: H1883-H1891.

9. Snider P, Standley K N, Wang J, Azhar M, Doetschman T, Conway S J. Origin of Cardiac Fibroblasts and the Role of Periostin. *Circ Res* 2009; 105: 934-947.

10. Frangogiannis N G. Targeting the inflammatory response in healing myocardial infarcts. *Curr Med Chem* 2006; 13: 1877-1893.

11. Konkalmatt P R, Wang F, Piras B A, Xu Y, O'Connor D M, Beyers R J et al. Adeno-associated virus serotype 9 administered systemically after reperfusion preferentially targets cardiomyocytes in the infarct border zone with pharmacodynamics suitable for the attenuation of left ventricular remodeling. *J Gene Med* 2012; 14: 609-620.

12. Konkalmatt P R, Beyers R J, O'Connor D M, Xu Y, Seaman M E, French B A. Cardiac-Selective Expression of Extracellular Superoxide Dismutase After Systemic Injection of Adeno-Associated Virus 9 Protects the Heart Against Post-Myocardial Infarction Left Ventricular Remodeling. *Circ Cardiovasc Imaging* 2013; 6: 478-486.

13. Sharma A, Ghosh A, Hansen E T, Newman J M, Mohan R R. Transduction efficiency of AAV 2/6,2/8 and 2/9 vectors for delivering genes in human corneal fibroblasts. *Brain Res Bull* 2010; 81: 273-278.

14. Prasad K M R, Xu Y, Yang Z, Acton S T, French B A. Robust cardiomyocyte-specific gene expression following systemic injection of AAV: in vivo gene delivery follows a Poisson distribution. *Gene Ther* 2011; 18: 43-52.

15. Lindsley A, Snider P, Zhou H, Rogers R, Wang J, Olaopa M et al. Identification and characterization of a novel Schwann and outflow tract endocardial cushion lineage-restricted periostin enhancer. *Dev Biol* 2007; 307: 340-355.

16. Takeda N, Manabe I, Uchino Y, Eguchi K, Matsumoto S, Nishimura S et al. Cardiac fibroblasts are essential for the adaptive response of the murine heart to pressure overload. *J Clin Invest* 2010; 120: 254-265.

17. Shimazaki M, Nakamura K, Kii I, Kashima T, Amizuka N, Li M et al. Periostin is essential for cardiac healing after acute myocardial infarction. *J Exp Med* 2008; 205: 295-303.

18. French B A, Kramer C M. Mechanisms of postinfarct left ventricular remodeling. *Drug Discov Today Dis Mech* 2007; 4: 185-196.

19. Frangogiannis N G, Michael L H, Entman M L. Myofibroblasts in reperfused myocardial infarcts express the embryonic form of smooth muscle myosin heavy chain (SMemb). *Cardiovasc Res* 2000; 48: 89-100.

20. Freed D H, Cunnington R H, Dangerfield A L, Sutton J S, Dixon I M C. Emerging evidence for the role of cardiotrophin-1 in cardiac repair in the infarcted heart. *Cardiovasc Res* 2005; 65: 782-792.

21. Raizman J E, Komljenovic J, Chang R, Deng C, Bedosky K M, Rattan S G et al. The participation of the Na+-Ca2+ exchanger in primary cardiac myofibroblast migration, contraction, and proliferation. *J Cell Physiol* 2007; 213: 540-551.

22. Santiago J-J, Dangerfield A L, Rattan S G, Bathe K L, Cunnington R H, Raizman J E et al. Cardiac fibroblast to myofibroblast differentiation in vivo and in vitro: Expression of focal adhesion components in neonatal and adult rat ventricular myofibroblasts. *Dev Dyn* 2010; 239: 1573-1584.

23. Frangogiannis N G, Shimoni S, Chang S, Ren G, Dewald O, Gersch C et al. Active interstitial remodeling: an important process in the hibernating human myocardium. *J Am Coll Cardiol* 2002; 39: 1468-1474.

24. Ieda M, Fu J-D, Delgado-Olguin P, Vedantham V, Hayashi Y, Bruneau B G et al. Direct Reprogramming of Fibroblasts into Functional Cardiomyocytes by Defined Factors. *Cell* 2010; 142: 375-386.

25. Inagawa K, Miyamoto K, Yamakawa H, Muraoka N, Sadahiro T, Umei T et al. Induction of Cardiomyocyte-like Cells in Infarct Hearts by Gene Transfer of Gata4, Mef2c, and Tbx5. *Circ Res* 2012. doi:10.1161/CIRCRESAHA.112.271148.

26. Qian L, Huang Y, Spencer C I, Foley A, Vedantham V, Liu L et al. In vivo reprogramming of murine cardiac fibroblasts into induced cardiomyocytes. *Nature* 2012; 485: 593-598.

27. Jayawardena T M, Egemnazarov B, Finch E A, Zhang L, Payne J A, Pandya K et al. MicroRNA-Mediated In Vitro and In Vivo Direct Reprogramming of Cardiac Fibroblasts to Cardiomyocytes. *Circ Res* 2012; 110: 1465-1473.

28. Norris R A, Borg T K, Butcher J T, Baudino T A, Banerjee I, Markwald R R. Neonatal and Adult Cardiovascular Pathophysiological Remodeling and Repair. *Ann N Y Acad Sci* 2008; 1123: 30-40.

29. Oka T, Xu J, Kaiser R A, Melendez J, Hambleton M, Sargent M A et al. Genetic Manipulation of Periostin Expression Reveals a Role in Cardiac Hypertrophy and Ventricular Remodeling. *Circ Res* 2007; 101: 313-321.

30. Kuhn B, del Monte F, Hajjar R J, Chang Y-S, Lebeche D, Arab S et al. Periostin induces proliferation of differentiated cardiomyocytes and promotes cardiac repair. *Nat Med* 2007; 13: 962-969.

31. Furtado M B, Costa M W, Pranoto E A, Salimova E, Pinto A R, Lam N T et al. Cardiogenic Genes Expressed in Cardiac Fibroblasts Contribute to Heart Development and Repair. *Circ Res* 2014; 114: 1422-1434.

32. Ruiz-Villalba A, Simon A M, Pogontke C, Castillo M I, Abizanda G, Pelacho B et al. Interacting Resident Epicardium-Derived Fibroblasts and Recruited Bone Marrow Cells Form Myocardial Infarction Scar. *J Am Coll Cardiol* 2015; 65: 2057-2066.

33. Lovric J, Mano M, Zentilin L, Eulalio A, Zacchigna S, Giacca M. Terminal Differentiation of Cardiac and Skeletal Myocytes Induces Permissivity to AAV Transduction by Relieving Inhibition Imposed by DNA Damage Response Proteins. *Mol Ther* 2012; 20: 2087-2097.

34. Schwartz R A, Palacios J A, Cassell G D, Adam S, Giacca M, Weitzman M D. The Mre11/Rad50/Nbs1 Complex Limits Adeno-Associated Virus Transduction and Replication. *J Virol* 2007; 81: 12936-12945.

35. Cervelli T, Palacios J A, Zentilin L, Mano M, Schwartz R A, Weitzman M D et al. Processing of recombinant AAV genomes occurs in specific nuclear structures that overlap with foci of DNA-damage-response proteins. *J Cell Sci* 2008; 121: 349-357.

36. van Wijk B, Gunst Q D, Moorman A F, Van den Hoff M J. Cardiac regeneration from activated epicardium. *PloS One* 2012; 7: e44692.

37. Willems I E, Havenith M G, De Mey J G, Daemen M J. The alpha-smooth muscle actin-positive cells in healing human myocardial scars. *Am J Pathol* 1994; 145: 868-875.

38. Ross A, Yang Z, Ben S, Gilson W, Petersen W, Oshinski J et al. Serial MRI evaluation of cardiac structure and function in mice after reperfused myocardial infarction. *Magn Reson Med* 2002; 47: 1158-1168.

39 Shimshek D R, Kim J, Hubner M R, Spergel D J, Buchholz F, Casanova E et al. Codon-improved Cre recombinase (iCre) expression in the mouse. *genesis* 2002; 32: 19-26.

40 Geisler A, Jungmann A, Kurreck J, Poller W, Katus H A, Vetter R et al. microRNA122-regulated transgene expression increases specificity of cardiac gene transfer upon intravenous delivery of AAV9 vectors. *Gene Ther* 2010; 18: 199-209.

41 Qiao C, Yuan Z, Li J, He B, Zheng H, Mayer C et al. Liver-specific microRNA-122 target sequences incorporated in AAV vectors efficiently inhibits transgene expression in the liver. *Gene Ther* 2010; 18: 403-410.

42 Madisen L, Zwingman T A, Sunkin S M, Oh S W, Zariwala H A, Gu H et al. A robust and high-throughput Cre reporting and characterization system for the whole mouse brain. *Nat Neurosci* 2010; 13: 133-140.

43 Safran M, Kim W Y, Kung A L, Homer J W, DePinho R A, Kaelin W G Jr. Mouse reporter strain for noninvasive bioluminescent imaging of cells that have undergone Cre-mediated recombination. *Mol Imaging* 2003; 2: 297-302.

44 Wu J C, Inubushi M, Sundaresan G, Schelbert H R, Gambhir S S. Optical Imaging of Cardiac Reporter Gene Expression in Living Rats. *Circulation* 2002; 105: 1631-1634.

45 Prasad K-M R, Xu Y, Yang Z, Toufektsian M-C, Ben S S, French B A. Topoisomerase Inhibition Accelerates Gene Expression after Adeno-associated Virus-mediated Gene Transfer to the Mammalian Heart. *Mol Ther* 2007; 15: 764-771.

46 Manthorpe M, Cornefert-Jensen F, Hartikka J, Feigner J, Rundell A, Margalith M et al. Gene Therapy by Intramuscular Injection of Plasmid DNA: Studies on Firefly Luciferase Gene Expression in Mice. *Hum Gene Ther* 1993; 4: 419-431.

47 Carle, Birdsall N. Autofluorescence in the identification of myocardial infarcts. *Hum Pathol* 1981; 12: 643-646.

48 Ellis et al., 2013, *Virology J.*, 10:74.

49 French et al., U.S. Pat. Pub. No. 2013/0136729, published May 30, 2013.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A method of targeting gene expression to a cardiac myofibroblast following an injury in a subject or in a subject with a cardiac disease or disorder, said method comprising administering to said subject a pharmaceutical composition comprising a recombinant adeno-associated viral (AAV) vector comprising a recombinant AAV genome comprising a 1395 basepair (bp) periostin promoter consisting of the nucleic acid sequence of SEQ ID NO: 6 operably linked to at least one gene for which expression in the cardiac myofibroblast is desired, and a capsid of an AAV selected from the group consisting of AAV9, AAV8, and AAV6, wherein said recombinant AAV genome is present within said capsid.

2. The method of claim 1, wherein the AAV9 is encoded by a nucleic acid comprising SEQ ID NO:1, the AAV8 is encoded by a nucleic acid comprising SEQ ID NO:2, and the AAV6 is encoded by a nucleic acid comprising SEQ ID NO:7.

3. The method of claim 2, wherein said AAV is AAV9.

4. The method of claim 1, wherein said at least one gene is a therapeutic gene or a reporter gene.

5. The method of claim 1, wherein said injury, disease, or disorder is selected from the group consisting of myocardial infarction, reperfusion injury, heart failure, and peripheral artery disease.

6. The method of claim 5, wherein said injury is myocardial infarction.

7. The method of claim 1, wherein said recombinant AAV vector preferentially targets an ischemic region of the heart.

8. The method of claim 7, wherein said pharmaceutical composition is administered after reperfusion occurs.

9. The method of claim 1, wherein said pharmaceutical composition is administered systemically to said subject.

10. A recombinant AAV vector comprising
a recombinant AAV genome comprising a 1395 bp periostin promoter consisting of the nucleic acid sequence of SEQ ID NO:6; and
a capsid of an AAV selected from the group consisting of AAV9, AAV8, and AAV6,
wherein said recombinant AAV genome is present within said capsid.

11. The recombinant AAV vector of claim 10, wherein said recombinant AAV vector comprises at least one gene operably linked to said 1395 bp periostin promoter.

12. The recombinant AAV vector of claim 11, wherein said AAV is AAV9.

13. The recombinant AAV vector of claim 10, wherein the AAV9 is encoded by a nucleic acid comprising SEQ ID NO:1, the AAV8 is encoded by a nucleic acid comprising SEQ ID NO:2, and the AAV6 is encoded by a nucleic acid comprising SEQ ID NO:7.

14. A method of treating a cardiac injury, disease, or disorder, the method comprising administering to a subject in need thereof a pharmaceutical composition comprising an effective amount of a recombinant AAV vector of claim 11.

15. The method of claim 14, wherein said pharmaceutical composition is administered systemically, intravenously, by intracoronary infusion, locally, or by direct injection into myocardium.

16. The method of claim 14, wherein said method efficiently transduces cardiac myofibroblasts but not cardiac myocytes.

17. The method of claim 14, wherein said AAV is AAV9.

18. The method of claim 14, wherein said pharmaceutical composition is administered to said subject at a time after said injury selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, and 95 hours.

19. The method of claim 14, wherein said injury is myocardial infarction.

20. The method of claim 15, wherein said pharmaceutical composition is administered systemically to said subject in need thereof.

* * * * *